United States Patent
Karstens et al.

(10) Patent No.: US 9,095,583 B2
(45) Date of Patent: Aug. 4, 2015

(54) RORGAMMAT INHIBITORS

(75) Inventors: Willem Frederik Johan Karstens, Berghem (NL); Mario Van Der Stelt, Utrecht (NL); Jos Cals, Oss (NL); Rita Corte Real Goncalves Azevedo, 's-Hertogenbosch (NL); Kenneth Jay Barr, Boston, MA (US); Hongjun Zhang, Newton, MA (US); Richard Thomas Beresis, Shanghai (CN); Dongshan Zhang, Shanghai (CN); Xiaobang Duan, Shanghai (CN)

(73) Assignees: Merck Sharp & Dohme Corp., Rahway, NJ (US); Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 13/983,818

(22) PCT Filed: Feb. 10, 2012

(86) PCT No.: PCT/CN2012/071017
§ 371 (c)(1),
(2), (4) Date: Oct. 17, 2013

(87) PCT Pub. No.: WO2012/106995
PCT Pub. Date: Aug. 16, 2012

(65) Prior Publication Data
US 2014/0038942 A1     Feb. 6, 2014

(30) Foreign Application Priority Data
Feb. 11, 2011 (EP) .................................. 11154188

(51) Int. Cl.
| | | |
|---|---|---|
| C07D 401/10 | (2006.01) |
| A61K 31/4353 | (2006.01) |
| A61K 31/4439 | (2006.01) |
| C07D 231/56 | (2006.01) |
| C07D 401/06 | (2006.01) |
| C07D 401/12 | (2006.01) |
| C07D 403/10 | (2006.01) |
| C07D 409/14 | (2006.01) |
| C07D 413/12 | (2006.01) |
| C07D 413/14 | (2006.01) |
| C07D 471/04 | (2006.01) |
| A61K 31/416 | (2006.01) |
| A61K 31/4245 | (2006.01) |
| A61K 31/437 | (2006.01) |
| A61K 31/4709 | (2006.01) |
| A61K 45/06 | (2006.01) |

(52) U.S. Cl.
CPC ........... *A61K 31/4439* (2013.01); *A61K 31/416* (2013.01); *A61K 31/4245* (2013.01); *A61K 31/437* (2013.01); *A61K 31/4709* (2013.01); *A61K 45/06* (2013.01); *C07D 231/56* (2013.01); *C07D 401/06* (2013.01); *C07D 401/12* (2013.01); *C07D 403/10* (2013.01); *C07D 409/14* (2013.01); *C07D 413/12* (2013.01); *C07D 413/14* (2013.01); *C07D 471/04* (2013.01)

(58) Field of Classification Search
CPC ........................... C07D 401/10; A61K 31/4353
USPC ........................... 546/113, 118; 514/300, 303
See application file for complete search history.

(56) References Cited

U.S. PATENT DOCUMENTS
2006/0100218 A1     5/2006 Ibrahim et al.

FOREIGN PATENT DOCUMENTS

| EP | 0429257 | A2 | 5/1991 |
| EP | 2181710 | A1 | 5/2010 |
| JP | 2007238463 | A | 9/2007 |
| WO | WO-2006063167 | A1 | 6/2006 |
| WO | 2008132434 | * | 11/2008 |
| WO | WO-2009015067 | A2 | 1/2009 |
| WO | WO-2010068483 | A2 | 6/2010 |
| WO | WO-2010150837 | A1 | 12/2010 |

OTHER PUBLICATIONS

International Search Report from PCT/CN2012/071017, mailed May 24, 2012.
Annunziato et al., "Type 17 T helper cells—origins, features and possible roles in rheumatic disease," 5 *Nat. Rev. Rheumatol.* 325-31 (2009).
Boaventura et al., "Human mucosal leishmanuasis: Neutrophils infiltrate areas of tissue damage that express high levels of Th17-related cytokines," 40 *Eur. J. Immunol.* 2830-36 (2010).
Bundgaard (ed.). *Design of Prodrugs*, Elsevier (1985).
Buonocore et al., "Innate lymphoid cells drive interleukin-23-dependent innate intestinal pathology," 464 *Nature* 1371-75 (2010).
(Continued)

*Primary Examiner* — Niloofar Rahmani
(74) *Attorney, Agent, or Firm* — Covington & Burling LLP; Andrea G. Reister; Melody Wu

(57) ABSTRACT

The present invention relates to compounds according to Formula (I) or a pharmaceutically acceptable salt or solvate thereof. Such compounds can be used in the treatment of RORgammaT-mediated diseases or condition.

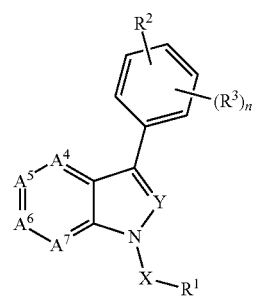

19 Claims, No Drawings

(56) References Cited

OTHER PUBLICATIONS

Cheng et al., "Design and synthesis of heterocyclic malonyl-CoA decarboxylase inhibitors," 16 *Bioorg. Med. Chem. Lett.* 695-700 (2006).

Eberl et al., "An essential function for the nuclear receptor RORγt in the generation of fetal lymphoid tissue inducer cells," 5(1) *Nat. Immunol.* 64-73 (2004).

Figueroa-Vega et al., "Increased Circulating Pro-Inflammatory Cytokines and Th17 Lymphocytes in Hashimoto's Thyroiditis," 95(2) *J. Clin. Endocrinol. Metab.* 953-62 (2010).

Gennaro (ed.), *Remington: The Science and Practice of Pharmacy*, 20th edition (2000).

He et al., "RORγt, a Novel Isoform of an Orphan Receptor, Negatively Regulates Fas Ligand Expression and IL-2, Production in T Cells," 9 *Immunity* 797-806 (1998).

Higuchi et al. (eds.), *Pro-drugs as Novel Delivery Systems*, 14 A.C.S. Symposium Series (1975).

Hirose et al., "RORγ: the third member of ROR/RZR orphan receptor subfamily that is highly expressed in skeletal muscle," 205 *Bioche. Biophys. Res. Comm.* 1976-83 (1994).

Hueber et al., "Cutting Edge: Mast Cells Express IL-17A in Rheumatoid Arthritis Synovium," 184 *J. Immunol.* 3336-40 (2010).

Ivanov et al., "The Orphan Nuclear Receptor RORγt Directs the Differentiation Program of Proinflammatory IL-17+ T Helper Cells," 126 *Cells* 1121-33 (2006).

Jia et al., "The T helper type 17/regulatory T cell imbalance in patients with acute Kawasaki disease," 162 *Clin. Exp. Immunol.* 131-37 (2010).

Jin et al., "Structural Basis for Hydroxycholesterols as Natural Ligands of Orphans Nuclear Receptor RORγ," 24(5) *Mol. Endocrinol.* 923-29 (2010).

Kastelein et al., "Discovery and Biology of IL-23 and IL-27: Related but Functionally Distinct Regulators of Inflammation," 25 *Annu. Rev. Immunol.* 221-42 (2007).

Kurebayashi et al., "Selective LXXLL peptides antagonize transcriptional activation by the retinoid-related orphan receptor RORγ," 315 *Biochem. Biophys. Res. Comm.* 919-27 (2004).

Louten et al., "Development and function of TH17 cells in health and disease," 123(5) *J. Allergy Clin. Immunol.* 1004-11 (2009).

Miossec et al., "Interleukin-17 and Type 17 Helper T Cells," 361(9) *New Eng. J. Med.* 888-98 (2009).

Roche (ed.), *Biorevesible Carriers in Drug Design*, Pergamon Press (1987).

Sun et al., "Requirement for RORγ in Thymocyte Survival and Lymphoid Organ Development," 288 *Science* 2369-72 (2000).

Sutton et al., "Interleukin-1 and IL-23 Induce Innate IL-17 Production from γδ T Cells, Amplifying Th17 Responses and Autoimmunity," 31 *Immunity* 331-41 (2009).

Wang et al., "Identification of SR1078, a Synthetic Agonist for the Orphan Nuclear Receptors RORα and RORγ," 5(11) ACS Chem. Biol. 1029-34 (2010).

Wang et al., "Modulation of Retinoic Acid Receptor-related Orphan Receptor α and γ Activity by 7-Oxygenated Sterol Ligands," 285(7) J. Bio. Chem. 5013-25 (2010).

Xie et al., "RORγt Recruits Steroid Receptor Coactivators to Ensure Thymocyte Survival," 175(6) *J. Immunol.* 3800-09 (2005).

Yang et al., "T Helper 17 Lineage Differentiation is programmed by Orphan Nuclear Recepors RORα and RORγ," 28 *Immunity* 29-39 (2008).

Zhou et al., "Use of Homogeneous Time-Resolved Fluorescence Energy Transfer in the Measurement of Nuclear Receptor Activation," 25 *Methods* 54-61 (2001).

Extended European Search Report, EP Application No. 12744370.3, Sep. 9, 2014.

Ciattini et al., "An Efficient Synthesis of 3-Substituted Indoles by Palladium-Catalyzed Coupling Reaction of 3-Tributylstannylindoles with Organic Triflates and Halides," 35(15) Tetrahedron Letters 2405-08 (1994).

Inamoto et al., "Palladium-Catalyzed C-H Activation/Intramolecular Amination Reaction: A New Route to 3-Aryl/Alkylindazoles," 9(15) Org. Letts. 2931-34 (2007).

Larhed et al., "Rapid Microwave-Assisted Suzuki Coupling on Solid-Phase," 37(45) Tetrahedron Letters 8219-22 (1996).

Reckenbeil et al., "Supramolekulare Phosphorylierung kationischer Alkohole mit 3-Arylindol-4-carboxamidin-Struktur," Liebigs Ann. Chem. 1219-29 (1994).

\* cited by examiner

SEQUENCE LISTING

```
<160> NUMBER OF SEQ ID NOS: 2

<210> SEQ ID NO 1
<211> LENGTH: 25
<212> TYPE: PRT
<213> ORGANISM: Artificial Sequence
<220> FEATURE:
<223> OTHER INFORMATION: SRC1_2 peptide

<400> SEQUENCE: 1

Cys Pro Ser Ser His Ser Ser Leu Thr Glu Arg His Lys Ile Leu His
1               5                   10                  15

Arg Leu Leu Gln Glu Gly Ser Pro Ser
            20                  25

<210> SEQ ID NO 2
<211> LENGTH: 5
<212> TYPE: PRT
<213> ORGANISM: Artificial Sequence
<220> FEATURE:
<223> OTHER INFORMATION: SCR1_2 peptide
<223> OTHER INFORMATION: Xaa can be any amino acid

<400> SEQUENCE: 2

Leu Xaa Xaa Leu Leu
1               5
```

RORGAMMAT INHIBITORS

BACKGROUND OF THE INVENTION

Upon activation by antigen-presenting cells naïve T helper cells undergo clonal expansion and will ultimately differentiate in cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 2361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205: 1976-1983, 1994). RORgammaT is a truncated form of RORgamma, lacking the first N-terminal 21 amino acids and is, in contrast to RORgamma which is expressed in multiple tissues (heart, brain, kidney, lung, liver and muscle), exclusively expressed in cells of the lymphoid lineage and embryonic lymphoid tissue inducers (Sun et al., *Science* 288: 2369-2372, 2000; Eberl et al., *Nat Immunol.* 5: 64-73, 2004).

Studies using heterozygous knock-in mice replacing the RORgammaT open reading frame with GFP, revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP and in vitro stimulation of CD4+ T cells, under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). Taken together demonstrating the importance of RORgammaT in differentiation and stabilization of the Th17 lineage. In addition, a ROR family member, RORalpha has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1 and IL-23R proteins. Genetic disruption of RORgamma in a mouse colitis model dependent on these innate lymphoid cells, prevented colitis development (Buonocore et al., *Nature* 464: 1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004) and gamma-delta T-cells (Sutton et al., *Nat. Immunol.* 31: 331-341, 2009; Louten et al., *J. Allergy Clin. Immunol.* 123: 1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., *J. Allergy Clin. Immunol.* 123: 1004-1011, 2009; Annunziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126: 1121-33, 2006; Buonocore et al., *Nature* 464: 1371-1375, 2010).

Being a critical mediator in Th17-cells and other non-Th17 cells, inhibition of RORgammaT is expected to have a beneficial effect on autoimmune diseases, such as, but not limited to rheumatoid arthritis, psoriasis, multiple sclerosis, inflammatory bowel disease, Crohn's disease, and asthma (Annunziato et al., *Nat. Rev. Immunol.* 5: 325-331, 2009; Louten et al., *J. Allergy Clin. Immunol.* 123: 1004-1011, 2009) Inhibition of RORgammaT may also be beneficial in other diseases, which are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162: 131-137, 2010) and Hashimoto's thyroiditis (Figueroa-Vega et al., *J. Clin. Endocrinol. Metab.* 95: 953-62, 2010). Another example includes infectious diseases, such as, but not limited to, mucosal leishmaniasis (Boaventura et al., *Eur. J. Immunol.* 40: 2830-2836, 2010). In each of the above examples the inhibition may be enhanced by simultaneous inhibition of RORalpha.

Compounds modulating RORgammaT have been reported. Examples of agonists include T0901317 and SR1078 (Wang et al., *ACS Chem. Biol.* 5:1029-1034, 2010). In addition, antagonist have been reported such as 7-oxygenated sterols (Wang et al., *J. Biol. Chem.* 285: 5013-5025, 2009) and compounds described in EP2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds which inhibit RORgammaT, their use for the treatment of RORgammaT-mediated diseases or conditions, in particular autoimmune diseases and inflammatory diseases, as well as pharmaceutical compositions comprising such compounds and pharmaceutical carriers.

DETAILED DESCRIPTION OF THE INVENTION

The present invention provides a compound according to Formula I

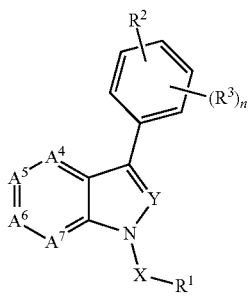

or a pharmaceutically acceptable salt or solvate thereof wherein,

X is C(O), SO or $SO_2$,
Y is CH or N;
n=0, 1, 2, 3 or 4;
$A^4$-$A^7$ are independently N or $CR^4$, $CR^5$, $CR^6$ or $CR^7$, respectively, with the proviso that no more than two of the four positions $A^4$-$A^7$ can be simultaneously N;
$R^1$ is (i) ($C_{3-7}$)cycloalkyl or ($C_{3-5}$)heterocycloalkyl, both optionally substituted with one or more groups selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl and ($C_{1-3}$)alkoxy are optionally substituted with one or more halogens; (ii) ($C_{2-9}$)heteroaryl, optionally substituted with one or more groups selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl and ($C_{1-3}$)alkoxy are optionally substituted with one or more halogens; or (iii) ($C_{6-14}$)aryl, optionally substituted with one or more groups selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl or ($C_{1-3}$)alkoxy are optionally substituted with one or more halogens;
$R^2$ is C(O)OH, 5-tetrazoylyl, $HOC(CF_3)_2$, $C(O)OH(C_{1-10})$alkyl, ($C_{1-10}$)alkylsulfoxyaminocarbonyl; or carbamoyl;
$R^3$ is hydrogen, halogen, cyano, nitro, hydroxy, (C1-3)alkylC(O)O—, ($C_{1-4}$)alkyl, or ($C_{1-4}$)alkoxy, wherein ($C_{1-4}$)alkyl and ($C_{1-4}$)alkoxy are optionally substituted with one or more halogens;
$R^4$-$R^7$ independently are H, halogen, amino, cyano, hydroxy, ($C_{1-3}$)alkoxy, ($C_{1-4}$)alkyl, ($C_{0-10}$)alkyl)aminocarbonyl, (di)($C_{1-6}$)alkylaminocarbonyl or amino($C_{1-4}$)alkyl, wherein ($C_{1-3}$)alkoxy, ($C_{1-4}$)alkyl, ($C_{0-10}$)alkyl)aminocarbonyl, (di)($C_{1-6}$)alkylaminocarbonyl and amino($C_{1-4}$)alkyl are optionally substituted with one or more halogen, hydroxyl or ($C_{1-3}$)alkoxy; or a group having the formula

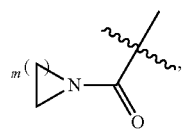

optionally substituted with one or more of the following: ($C_{1-10}$)alkyl, halogen, amino, cyano, hydroxy, ($C_{1-3}$)alkoxy, and wherein m is 1, 2, 3, or 4.

This invention also provides a compound according to Formula Ia

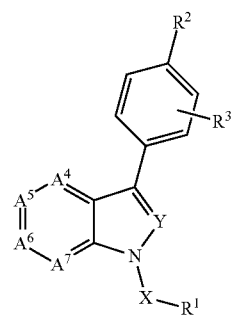

or a pharmaceutically acceptable salt or solvate thereof
wherein X represents C(O), SO or $SO_2$,
Y is CH or N;
$A^4$-$A^7$ are independently N or $CR^4$, $CR^5$, $CR^6$ or $CR^7$, respectively, with the proviso that no more than two of the four positions $A^4$-$A^7$ can be simultaneously N;
$R^1$ is ($C_{3-7}$)cycloalkyl or ($C_{3-5}$)heterocycloalkyl, both optionally substituted with one or more groups selected from halogen, amino, cyano, hydroxy, $H_2NC(O)$—, or ($C_{1-3}$)alkoxycarbonyl, (di)($C_{1-6}$)alkylaminocarbonyl, ($C_{1-4}$)alkyl or ($C_{1-3}$)alkoxy, all optionally substituted with one or more halogens or;
$R^1$ is ($C_{2-9}$)heteroaryl, optionally substituted with one or more groups selected from halogen, amino, cyano, nitro, hydroxy, $H_2NC(O)$—, or ($C_{1-3}$)alkoxycarbonyl, (di)($C_{1-6}$)alkylaminocarbonyl, ($C_{1-4}$)alkyl or ($C_{1-3}$)alkoxy, all optionally substituted with one or more halogens or;
$R^1$ is ($C_{6-14}$)aryl, optionally substituted with one or more groups selected from halogen, amino, cyano, nitro, hydroxy, $H_2NC(O)$—, or ($C_{1-3}$)alkoxycarbonyl, (di)($C_{1-6}$)alkylaminocarbonyl, ($C_{1-4}$)alkyl or ($C_{1-3}$)alkoxy, all optionally substituted with one or more halogens;
$R^2$ is C(O)OH, 5-tetrazoylyl, or $HOC(CF_3)_2$;
$R^3$ is independently selected from hydrogen, halogen, cyano, nitro or ($C_{1-4}$)alkyl, optionally substituted with one or more halogens; and
$R^4$-$R^7$ independently are H, halogen, amino, cyano, hydroxy, ($C_{1-3}$)alkoxy, ($C_{1-4}$)alkyl, optionally substituted with one or more halogens.

In the first embodiment of the compounds of Formula I and Ia are compounds wherein $A^4$, $A^5$, $A^6$, $A^7$ are selected from the group consisting of: (i) $CR^4$, $CR^5$, $CR^6$, $CR^7$; (ii) N, $CR^5$, $CR^6$, $CR^7$; (iii) $CR^4$, N, $CR^6$, $CR^7$; (iv) $CR^4$, $CR^5$, N, $CR^7$; (v) $CR^4$, $CR^5$, $CR^6$, N; (vi) N, N, $CR^6$, $CR^7$; (vii) $CR^4$, N, N, $CR^7$; (viii) $CR^4$, $CR^5$, N, N; (ix) N, $CR^5$, N, $CR^7$; (x) $CR^4$, N, $CR^6$, N; and (xi) N, $CR^5$, $CR^6$, N.

In a subset of the first embodiment are compounds wherein $A^4$, $A^5$, $A^6$, $A^7$ are selected from the group consisting of: (i) $CR^4$, $CR^5$, $CR^6$, $CR^7$; (ii) N, $CR^5$, $CR^6$, $CR^7$; and (iii) $CR^4$, N, $CR^6$, $CR^7$.

In a second subset of the first embodiment are compounds wherein $A^4$, $A^5$, $A^6$, $A^7$ is (i) $CR^4$, $CR^5$, $CR^6$, $CR^7$, or (ii) N, $CR^5$, $CR^6$, $CR^7$; and Y is N.

In a third subset of the first embodiment are compounds wherein
X is C(O) or $SO_2$;
$R^1$ is (i) ($C_{3-7}$)cycloalkyl or ($C_{3-5}$)heterocycloalkyl, both optionally substituted with one or more groups selected from ($C_{1-4}$)alkyl or halogen; (ii) ($C_{2-9}$)heteroaryl, optionally substituted with one or more groups selected from halogen, amino or ($C_{1-4}$)alkyl; or (iii) ($C_{6-14}$)aryl, optionally substituted with one or more groups selected from halogen, amino, cyano, nitro, hydroxy, ($C_{1-3}$)alkoxycarbonyl, ($C_{1-4}$)alkyl, ($C_{1-3}$)alkoxy, wherein ($C_{1-3}$)alkoxycarbonyl, ($C_{1-4}$)alkyl and ($C_{1-3}$)alkoxy are optionally substituted with one or more halogens.

In a fourth subset of the first embodiment are compounds wherein
$R^1$ is ($C_{2-9}$)heteroaryl or ($C_{6-14}$)aryl, both optionally substituted with one or more groups selected from halogen, amino, cyano, nitro, hydroxy, ($C_{1-3}$)alkoxycarbonyl, ($C_{1-4}$ alkyl or ($C_{1-3}$)alkoxy, wherein ($C_{1-3}$)alkoxycarbonyl, ($C_{1-4}$)alkyl and ($C_{1-3}$)alkoxy are optionally substituted with one or more halogen.

In a fifth subset of the first embodiment are compounds according to Formula I wherein R1 is ($C_{6-14}$)aryl, optionally substituted with one or more groups selected from halogen, amino, cyano, nitro, hydroxy, or ($C_{1-3}$)alkoxycarbonyl, ($C_{1-4}$)alkyl or ($C_{1-3}$)alkoxy, all optionally substituted with one or more halogen.

In a sixth subset of the first embodiment are compounds wherein $R^1$ is phenyl, naphthyl, pyridinyl, quinolinyl, benzooxadiazolyl, thiophenyl, or isoxazolyl, each optionally substituted with one or more groups selected from halogen, amino, cyano, nitro, hydroxy, ($C_{1-3}$)alkoxycarbonyl, ($C_{1-4}$)alkyl or ($C_{1-3}$)alkoxy, wherein ($C_{1-3}$)alkoxycarbonyl, ($C_{1-4}$)alkyl and ($C_{1-3}$)alkoxy are optionally substituted with one or more halogens.

In a seventh subset of the first embodiment are compounds according to Formula I and Ia wherein ($C_{6-14}$)aryl in $R^1$ is phenyl.

In an eighth subset of the of the first embodiment are compounds wherein $R^1$ is phenyl, optionally substituted with one or more groups selected from halogen, amino, cyano, nitro, hydroxy, ($C_{1-3}$)alkoxycarbonyl, ($C_{1-4}$)alkyl or ($C_{1-3}$)alkoxy, wherein ($C_{1-3}$)alkoxycarbonyl, ($C_{1-4}$)alkyl and ($C_{1-3}$)alkoxy are optionally substituted with one or more halogens.

In a ninth subset of the first embodiment, are compounds wherein $R^2$ is C(O)OH.

A tenth subset of the invention relates to compounds according to Formula I and Ia wherein Y is N.

In a second embodiment of the compound of Formula I is a compound having Formula Ib

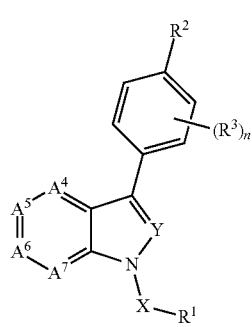

Ib and a pharmaceutically acceptable salt or solvate thereof, wherein $A^4$-$A^7$, $R^1$-$R^3$, X, Y and n are defined as set forth hereinabove for Formula I.

In a third embodiment of the compound of Formula I is a compound having Formula Ic

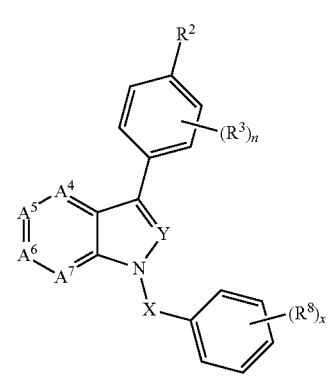

Ic or a pharmaceutically acceptable salt or solvate thereof wherein,

X is C(O) or $SO_2$ $R^8$ is selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl or ($C_{1-3}$)alkoxy are optionally substituted with one or more halogens;

x is 0, 1, 2, 3, 4 or 5; and $A^4$-$A^7$, $R^1$-$R^3$, Y and n are defined as set forth hereinabove for Formula I.

In a fourth embodiment of the compound of Formula I is a compound having Formula Id

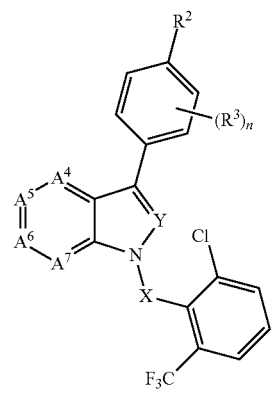

Id and a pharmaceutically acceptable salt or solvate thereof, wherein $A^4$-$A^7$, $R^2$, $R^3$, X, Y and n are defined as set forth hereinabove for Formula I.

In a fifth embodiment of the compound of Formula I is a compound having Formula Ie

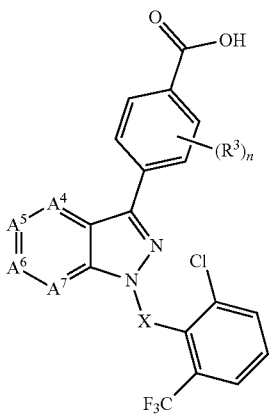

and a pharmaceutically acceptable salt or solvate thereof, wherein $A^4$-$A^7$, $R^3$, X and n are defined as set forth hereinabove for Formula I.

In a further embodiment of the compounds of Formula I, Ia, Ib, Ic, Id, and Ie, are compounds wherein
$R^4$ is selected from H, halogen, amino, and ($C_{1-4}$)alkyl optionally substituted with one or more halogen;
$R^5$ is H;
$R^6$ is selected from H, dimethylaminocarbonyl, —CH2NH2, cyano,

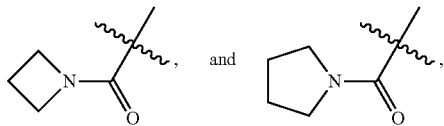 [SMILES: *C(=O)N1CCC1 ; *C(=O)N1CCCC1]

each optionally substituted with one or more halogen, hydroxyl, —$CH_2OH$, —$CH_2OCH_3$ or methoxy; and
$R^7$ is selected from H and halogen.

A still further embodiment of the compounds of Formula I, Ia, Ib, Ic, Id, and Ie, are compounds wherein one of $R^4$, $R^5$ and $R^7$ is other than hydrogen.

The invention also relates to those compounds wherein all specific definitions for $A^1$ through $A^4$, $R^1$ through $R^8$, X, Y, n and x and all substituent groups in the various aspects of the inventions defined here above occur in any combination within the definition of the compound of Formula I.

Non-limiting examples of the compounds of the present invention include:
4-(1-(2,6-dichlorobenzoyl)-1H-indazol-3-yl)benzoic acid;
4-(1-(2,6-dichlorobenzoyl)-5-fluoro-1H-indazol-3-yl)benzoic acid;
4-(1-(2,6-dichlorobenzoyl)-7-fluoro-1H-indazol-3-yl)benzoic acid;
4-(1-(2,6-dichlorobenzoyl)-4-fluoro-1H-indazol-3-yl)benzoic acid;
4-(1-(2,6-dichlorobenzoyl)-6-fluoro-1H-indazol-3-yl)benzoic acid;
4-(1-(2,6-dichlorobenzoyl)-1H-pyrazolo[4,3-b]pyridin-3-yl)benzoic acid;
4-(1-(2-(trifluoromethyl)benzoyl)-1H-pyrazolo[4,3-b]pyridin-3-yl)benzoic acid;
4-(1-(2,6-dichlorobenzoyl)-1H-pyrrolo[3,2-b]pyridin-3-yl)benzoic acid;
4-(1-(2,6-dichlorobenzoyl)-1H-pyrazolo[4,3-c]pyridin-3-yl)benzoic acid;
1,1,1,3,3,3-hexafluoro-2-(4-(1-(2-(trifluoromethyl)phenylsulfonyl)-1H-indazol-3-yl)phenyl)propan-2-ol;
4-(1-(2-(trifluoromethyl)benzoyl)-1H-indazol-3-yl)benzoic acid;
4-(1-(3,5-dichloroisonicotinoyl)-1H-indazol-3-yl)benzoic acid;
4-(1-(2-bromobenzoyl)-1H-indazol-3-yl)benzoic acid;
4-(1-(2-(methoxycarbonyl)benzoyl)-1H-indazol-3-yl)benzoic acid;
4-(1-(cyclohexanecarbonyl)-1H-indazol-3-yl)benzoic acid;
4-(1-(2-bromo-6-chlorobenzoyl)-1H-indazol-3-yl)benzoic acid;
4-(1-(2-fluoro-6-(trifluoromethyl)benzoyl)-1H-indazol-3-yl)benzoic acid;
4-(1-(2-fluoro-6-methoxybenzoyl)-1H-indazol-3-yl)benzoic acid;
4-(1-(2,4,6-trichlorobenzoyl)-1H-indazol-3-yl)benzoic acid;
4-(1-(2,6-dimethylbenzoyl)-1H-indazol-3-yl)benzoic acid;
4-(1-(2-ethoxybenzoyl)-1H-indazol-3-yl)benzoic acid;
4-(1-(2,3-dichlorobenzoyl)-1H-indazol-3-yl)benzoic acid;
4-(1-(2-chlorobenzoyl)-1H-indazol-3-yl)benzoic acid;
4-(1-(2-chloro-6-(trifluoromethyl)benzoyl)-1H-indazol-3-yl)benzoic acid;
4-(1-(2-methyl-6-nitrobenzoyl)-1H-indazol-3-yl)benzoic acid;
4-(1-(2-(trifluoromethyl)phenylsulfonyl)-1H-indazol-3-yl)benzoic acid;
4-(1-(quinolin-8-ylsulfonyl)-1H-indazol-3-yl)benzoic acid;
4-(1-(2-bromophenylsulfonyl)-1H-indazol-3-yl)benzoic acid;
4-(1-(2,5-dichlorophenylsulfonyl)-1H-indazol-3-yl)benzoic acid;
4-(1-(3-chloro-2-methylphenylsulfonyl)-1H-indazol-3-yl)benzoic acid;
4-(1-(2,3-dichlorophenylsulfonyl)-1H-indazol-3-yl)benzoic acid;
4-(1-(2,3,4-trichlorophenylsulfonyl)-1H-indazol-3-yl)benzoic acid;
4-(1-(2-cyanophenylsulfonyl)-1H-indazol-3-yl)benzoic acid;
4-(1-(2-(trifluoromethoxy)phenylsulfonyl)-1H-indazol-3-yl)benzoic acid;
4-(1-(naphthalen-1-ylsulfonyl)-1H-indazol-3-yl)benzoic acid;
4-(1-(2,6-dichlorophenylsulfonyl)-1H-indazol-3-yl)benzoic acid;
4-(1-(benzo[c][1,2,5]oxadiazol-4-ylsulfonyl)-1H-indazol-3-yl)benzoic acid;
4-(1-(2-cyano-5-methylphenylsulfonyl)-1H-indazol-3-yl)benzoic acid;
4-(1-(3,5-dimethylphenylsulfonyl)-1H-indazol-3-yl)-3-fluorobenzoic acid;
4-(1-(3,5-dimethylphenylsulfonyl)-1H-indazol-3-yl)-2-(trifluoromethyl)benzoic acid;
4-(1-(2-chlorophenylsulfonyl)-1H-pyrazolo[4,3-c]pyridin-3-yl)benzoic acid;
3-(4-(1H-tetrazol-5-yl)phenyl)-1-(3-chlorophenylsulfonyl)-1H-indazole;
methyl 3-(3-(4-(1H-tetrazol-5-yl)phenyl)-1H-indazol-1-ylsulfonyl)thiophene-2-carboxylate;
3-(4-(1H-tetrazol-5-yl)phenyl)-1-(2-bromo-4-fluorophenylsulfonyl)-1H-indazole;
3-(4-(1H-tetrazol-5-yl)phenyl)-1-(3-bromo-5-chlorothiophen-2-ylsulfonyl)-1H-indazole;
4-(3-(4-(1H-tetrazol-5-yl)phenyl)-1H-indazol-1-ylsulfonyl)-3,5-dimethylisoxazole;

(3-(4-(1H-tetrazol-5-yl)phenyl)-1H-indazol-1-yl)(2,6-dichlorophenyl)methanone;
(3-(4-(1H-tetrazol-5-yl)phenyl)-1H-indazol-1-yl)(2,3-dichlorophenyl)methanone;
methyl 4-(1-(2-chloro-6-(trifluoromethyl)benzoyl)-4-fluoro-1H-indazol-3-yl)-3-fluorobenzoate;
4-(1-(2-chloro-6-(trifluoromethyl)benzoyl)-4-fluoro-1H-indazol-3-yl)-3-fluorobenzoic acid;
Sodium 4-(1-(2-chloro-6-(trifluoromethyl)benzoyl)-4-fluoro-1H-indazol-3-yl)-3-fluorobenzoate;
methyl 4-(1-(2-chloro-6-(trifluoromethyl)benzoyl)-1H-indazol-3-yl)benzoate;
4-(1-(2-chloro-6-(trifluoromethyl)benzoyl)-1H-indazol-3-yl)benzoic acid; sodium 4-(1-(2-chloro-6-(trifluoromethyl)benzoyl)-1H-indazol-3-yl)benzoate;
methyl 4-(1-(2-chloro-6-(trifluoromethyl)benzoyl)-1H-pyrazolo[4,3-b]pyridin-3-yl)-3-fluorobenzoate;
sodium 4-(1-(2-chloro-6-(trifluoromethyl)benzoyl)-1H-pyrazolo[4,3-b]pyridin-3-yl)-3-fluorobenzoate;
(2-chloro-6-(trifluoromethyl)phenyl)(4-fluoro-3-(4-(1,1,1,3,3,3-hexafluoro-2-hydroxypropan-2-yl)phenyl)-1H-indazol-1-yl)methanone;
3-(1-(2-chloro-6-(trifluoromethyl)benzoyl)-4-fluoro-1H-indazol-3-yl)benzoic acid;
2-(3-(1-(2-chloro-6-(trifluoromethyl)benzoyl)-4-fluoro-1H-indazol-3-yl)phenyl)acetic acid;
2-(4-(1-(2-chloro-6-(trifluoromethyl)benzoyl)-4-fluoro-1H-indazol-3-yl)phenyl)acetic acid;
2-chloro-4-(1-(2-chloro-6-(trifluoromethyl)benzoyl)-4-fluoro-1H-indazol-3-yl)benzoic acid; Sodium 3-chloro-4-(1-(2-chloro-6-(trifluoromethyl)benzoyl)-4-fluoro-1H-indazol-3-yl)benzoate;
4-(1-(2-chloro-6-(trifluoromethyl)benzoyl)-4-fluoro-1H-indazol-3-yl)benzamide;
4-(1-(2-chloro-6-(trifluoromethyl)benzoyl)-4-fluoro-1H-indazol-3-yl)-2-fluoro-5-methylbenzoic acid;
4-(1-(2-chloro-6-(trifluoromethyl)benzoyl)-4-fluoro-1H-indazol-3-yl)-3-methylbenzoicacid;
4-(1-(2-chloro-6-(trifluoromethyl)benzoyl)-4-fluoro-1H-indazol-3-yl)-2-methoxybenzoic acid;
4-(1-(2-chloro-6-(trifluoromethyl)benzoyl)-4-fluoro-1H-indazol-3-yl)-2-fluorobenzoic acid; sodium 4-(1-(2-chloro-6-(trifluoromethyl)benzoyl)-4-fluoro-1H-indazol-3-yl)-2-fluorobenzoate;
4-(1-(2-chloro-6-(trifluoromethyl)benzoyl)-4-fluoro-1H-indazol-3-yl)-2-methylbenzoic acid;
4-(1-(2-chloro-6-(trifluoromethyl)benzoyl)-4-fluoro-1H-indazol-3-yl)-3-methoxybenzoic acid;
4-(1-(2-chloro-6-(trifluoromethyl)benzoyl)-4-fluoro-1H-indazol-3-yl)-2,6-difluorobenzoic acid;
4-(1-(2-chloro-6-(trifluoromethyl)benzoyl)-4-fluoro-1H-indazol-3-yl)-2-isopropylbenzoic acid;
4-(1-(2-chloro-6-(trifluoromethyl)benzoyl)-4-fluoro-1H-indazol-3-yl)-3,5-dimethoxybenzoic acid;
4-(1-(2-chloro-6-(trifluoromethyl)benzoyl)-4-fluoro-1H-indazol-3-yl)-2-cyano benzoic acid;
4-(1-(2-chloro-6-(trifluoromethyl)benzoyl)-4-fluoro-1H-indazol-3-yl)-2,3-difluorobenzoic acid;
4-(1-(2-chloro-6-(trifluoromethyl)benzoyl)-4-fluoro-1H-indazol-3-yl)-2,5-difluorobenzoic acid;
2-chloro-4-(1-(2-chloro-6-(trifluoromethyl)benzoyl)-4-fluoro-1H-indazol-3-yl)-5-fluorobenzoic acid;
4-(1-(2-chloro-6-(trifluoromethyl)benzoyl)-4-fluoro-1H-indazol-3-yl)-5-fluoro-2-methoxybenzoic acid;
5-(1-(2-chloro-6-(trifluoromethyl)benzoyl)-4-fluoro-1H-indazol-3-yl)-2-hydroxybenzoic acid;
3-fluoro-4-(4-fluoro-1-(2-fluoro-6-methoxybenzoyl)-1H-indazol-3-yl)benzoic acid;
4-(4-fluoro-1-(2-fluoro-6-methoxybenzoyl)-1H-indazol-3-yl)benzoic acid;
3-(1-(2-chloro-6-(trifluoromethyl)benzoyl)-1H-pyrazolo[4,3-b]pyridin-3-yl)benzoic acid;
2-(4-(1-(2-chloro-6-(trifluoromethyl)benzoyl)-1H-pyrazolo[4,3-b]pyridin-3-yl)phenyl)acetic acid;
(2-chloro-6-(trifluoromethyl)phenyl)(3-(4-(1,1,1,3,3,3-hexafluoro-2-hydroxypropan-2-yl)phenyl)-1H-pyrazolo[4,3-b]pyridin-1-yl)methanone;
4-(1-(2-chloro-6-(trifluoromethyl)benzoyl)-1H-pyrazolo[4,3-b]pyridin-3-yl)-3-methylbenzoic acid;
3-chloro-4-(1-(2-chloro-6-(trifluoromethyl)benzoyl)-1H-pyrazolo[4,3-b]pyridin-3-yl)benzoic acid;
4-(1-(2-chloro-6-(trifluoromethyl)benzoyl)-1H-pyrazolo[4,3-b]pyridin-3-yl)-2-fluorobenzoic acid;
4-(1-(2-chloro-6-(trifluoromethyl)benzoyl)-1H-pyrazolo[4,3-b]pyridin-3-yl)-2-methoxybenzoic acid;
2-chloro-4-(1-(2-chloro-6-(trifluoromethyl)benzoyl)-1H-pyrazolo[4,3-b]pyridin-3-yl)-5-fluorobenzoic acid;
4-(1-(2-chloro-6-(trifluoromethyl)benzoyl)-1H-pyrazolo[4,3-b]pyridin-3-yl)-2,5-difluorobenzoic acid;
5-(1-(2-chloro-6-(trifluoromethyl)benzoyl)-1H-pyrazolo[4,3-b]pyridin-3-yl)-2-hydroxybenzoic acid;
4-(1-(2-fluoro-6-methoxybenzoyl)-1H-pyrazolo[4,3-b]pyridin-3-yl)benzoic acid;
3-fluoro-4-(1-(2-fluoro-6-methoxybenzoyl)-1H-pyrazolo[4,3-b]pyridin-3-yl)benzoic acid;
4-(1-(2-chloro-6-(trifluoromethyl)benzoyl)-4-(trifluoromethyl)-1H-indazol-3-yl)benzoic acid;
4-(1-(2-chloro-6-(trifluoromethyl)benzoyl)-1H-indazol-3-yl)-2-isopropylbenzoic acid;
sodium 4-(1-(2-chloro-6-(trifluoromethyl)benzoyl)-1H-indazol-3-yl)-2-fluoro benzoate;
sodium 4-(1-(2-chloro-6-(trifluoromethyl)benzoyl)-1H-indazol-3-yl)-3-fluoro benzoate;
3-chloro-4-(1-(2-chloro-6-(trifluoromethyl)benzoyl)-1H-indazol-3-yl)benzoic acid;
3-fluoro-4-(1-(2-fluoro-6-methoxybenzoyl)-1H-indazol-3-yl)benzoic acid;
sodium 3-fluoro-4-(1-(2-fluoro-6-methoxybenzoyl)-1H-indazol-3-yl)benzoate;
4-(7-fluoro-1-(2-fluoro-6-methoxybenzoyl)-1H-indazol-3-yl)benzoic acid;
3-fluoro-4-(7-fluoro-1-(2-fluoro-6-methoxybenzoyl)-1H-indazol-3-yl)benzoic acid;
4-(6-bromo-1-(2-chloro-6-(trifluoromethyl)benzoyl)-4-fluoro-1H-indazol-3-yl)benzoic acid;
4-(6-bromo-1-(2-chloro-6-(trifluoromethyl)benzoyl)-1H-indazol-3-yl)benzoic acid;
4-(1-(2-chloro-6-(trifluoromethyl)benzoyl)-4-fluoro-6-methoxy-1H-indazol-3-yl)benzoic acid;
4-(1-(2-chloro-6-(trifluoromethyl)benzoyl)-6-hydroxy-1H-indazol-3-yl)benzoic acid;
sodium 4-(1-(2-chloro-6-(trifluoromethyl)benzoyl)-6-hydroxy-1H-indazol-3-yl)benzoate;
4-(1-(2-chloro-6-(trifluoromethyl)benzoyl)-6-hydroxy-1H-indazol-3-yl)-3-fluorobenzoic acid;
4-(1-(2-chloro-6-(trifluoromethyl)benzoyl)-4-fluoro-6-hydroxy-1H-indazol-3-yl)benzoic acid;
4-(1-(2-chloro-6-(trifluoromethyl)benzoyl)-4-fluoro-6-hydroxy-1H-indazol-3-yl)-3-fluorobenzoic acid;
4-(1-(2-chloro-6-(trifluoromethyl)benzoyl)-6-(hydroxymethyl)-1H-indazol-3-yl)benzoic acid;
4-(1-(2-chloro-6-(trifluoromethyl)benzoyl)-6-(hydroxymethyl)-1H-indazol-3-yl)-3-fluorobenzoic acid;

4-(1-(2-chloro-6-(trifluoromethyl)benzoyl)-6-(methoxymethyl)-1H-indazol-3-yl)benzoic acid;
1-(2-chloro-6-(trifluoromethyl)benzoyl)-3-(4-(methoxy carbonyl)phenyl)-1H-indazole-6-carboxylic acid;
methyl 4-(1-(2-chloro-6-(trifluoromethyl)benzoyl)-6-(2-hydroxyethylcarbamoyl)-1H-indazol-3-yl)benzoate;
4-(1-(2-chloro-6-(trifluoromethyl)benzoyl)-6-(2-hydroxy ethylcarbamoyl)-1H-indazol-3-yl)benzoic acid;
sodium 4-(1-(2-chloro-6-(trifluoromethyl)benzoyl)-6-(2-hydroxyethylcarbamoyl)-1H-indazol-3-yl)benzoate;
4-(1-(2-chloro-6-(trifluoromethyl)benzoyl)-6-(dimethylcarbamoyl)-1H-indazol-3-yl)benzoic acid;
4-(1-(2-chloro-6-(trifluoromethyl)benzoyl)-6-(2-hydroxyethylcarbamoyl)-1H-indazol-3-yl)benzoic acid;
sodium 4-(1-(2-chloro-6-(trifluoromethyl)benzoyl)-6-(2-hydroxyethylcarbamoyl)-1H-indazol-3-yl)benzoate;
4-(1-(2-chloro-6-(trifluoromethyl)benzoyl)-6-(dimethylcarbamoyl)-1H-indazol-3-yl)-3-fluorobenzoic acid;
sodium 4-(1-(2-chloro-6-(trifluoromethyl)benzoyl)-6-(dimethylcarbamoyl)-1H-indazol-3-yl)-3-fluorobenzoate;
4-(1-(2-chloro-6-(trifluoromethyl)benzoyl)-6-(2-hydroxyethylcarbamoyl)-1H-indazol-3-yl)-2-fluorobenzoic acid;
4-(1-(2-chloro-6-(trifluoromethyl)benzoyl)-6-(2-hydroxyethylcarbamoyl)-1H-indazol-3-yl)-3-fluorobenzoic acid;
4-(1-(2-chloro-6-(trifluoromethyl)benzoyl)-6-(dimethylcarbamoyl)-1H-indazol-3-yl)-2-fluorobenzoic acid;
3-chloro-4-(1-(2-chloro-6-(trifluoromethyl)benzoyl)-6-(dimethylcarbamoyl)-1H-indazol-3-yl)benzoic acid;
3-chloro-4-(1-(2-chloro-6-(trifluoromethyl)benzoyl)-6-(2-hydroxyethylcarbamoyl)-1H-indazol-3-yl)benzoic acid;
4-(1-(2-chloro-6-(trifluoromethyl)benzoyl)-6-(3-hydroxypropylcarbamoyl)-1H-indazol-3-yl)benzoic acid;
4-(1-(2-chloro-6-(trifluoromethyl)benzoyl)-6-(3-hydroxypropylcarbamoyl)-1H-indazol-3-yl)-3-fluorobenzoic acid;
4-(1-(2-chloro-6-(trifluoromethyl)benzoyl)-6-(3-methoxypropylcarbamoyl)-1H-indazol-3-yl)-3-fluorobenzoic acid;
4-(1-(2-chloro-6-(trifluoromethyl)benzoyl)-6-(2-hydroxypropylcarbamoyl)-1H-indazol-3-yl)benzoic acid;
4-(1-(2-chloro-6-(trifluoromethyl)benzoyl)-6-(4-hydroxybutylcarbamoyl)-1H-indazol-3-yl)benzoic acid;
4-(1-(2-chloro-6-(trifluoromethyl)benzoyl)-6-((2-hydroxyethyl)(methyl)carbamoyl)-1H-indazol-3-yl)benzoic acid;
4-(1-(2-chloro-6-(trifluoromethyl)benzoyl)-6-((2-hydroxyethyl)(methyl)carbamoyl)-1H-indazol-3-yl)-3-fluorobenzoic acid;
4-(1-(2-chloro-6-(trifluoromethyl)benzoyl)-6-((2-methoxyethyl)(methyl)carbamoyl)-1H-indazol-3-yl)-3-fluorobenzoic acid;
4-(1-(2-chloro-6-(trifluoromethyl)benzoyl)-6-(3-fluoroazetidine-1-carbonyl)-1H-indazol-3-yl)benzoic acid;
4-(1-(2-chloro-6-(trifluoromethyl)benzoyl)-6-(3,3-difluoroazetidine-1-carbonyl)-1H-indazol-3-yl)benzoic acid;
4-(1-(2-chloro-6-(trifluoromethyl)benzoyl)-6-(pyrrolidine-1-carbonyl)-1H-indazol-3-yl)benzoic acid;
4-(6-(azetidine-1-carbonyl)-1-(2-chloro-6-(trifluoromethyl)benzoyl)-1H-indazol-3-yl)benzoic acid;
4-(1-(2-chloro-6-(trifluoromethyl)benzoyl)-4-fluoro-1H-indazol-3-yl)-2-hydroxybenzoic acid;
2-acetoxy-4-(1-(2-chloro-6-(trifluoromethyl)benzoyl)-4-fluoro-1H-indazol-3-yl)benzoic acid;
sodium 4-(1-(2-chloro-6-(trifluoromethyl)benzoyl)-4-fluoro-1H-indazol-3-yl)-2-hydroxybenzoate;
4-(1-(2-chloro-6-(trifluoromethyl)benzoyl)-4-fluoro-1H-indazol-3-yl)-2-fluoro-6-hydroxybenzoic acid;
4-(1-(2-chloro-6-(trifluoromethyl)benzoyl)-4-fluoro-1H-indazol-3-yl)-3-hydroxybenzoic acid;
4-(1-(2-chloro-6-(trifluoromethyl)benzoyl)-4-fluoro-1H-indazol-3-yl)-5-fluoro-2-hydroxybenzoic acid;
4-(1-(2-chloro-6-(trifluoromethyl)benzoyl)-4-fluoro-1H-indazol-3-yl)-3,6-difluoro-2-hydroxybenzoic acid;
4-(1-(2-chloro-6-(trifluoromethyl)benzoyl)-1H-pyrazolo[4,3-b]pyridin-3-yl)-2-hydroxybenzoic acid;
2-acetoxy-4-(1-(2-chloro-6-(trifluoromethyl)benzoyl)-1H-pyrazolo[4,3-b]pyridin-3-yl)benzoic acid;
4-(1-(2-chloro-6-(trifluoromethyl)benzoyl)-6-(dimethylcarbamoyl)-1H-indazol-3-yl)-2-hydroxybenzoic acid;
4-(6-(aminomethyl)-1-(2-chloro-6-(trifluoromethyl)benzoyl)-1H-indazol-3-yl)benzoic acid;
4-(6-(aminomethyl)-1-(2-chloro-6-(trifluoromethyl)benzoyl)-1H-indazol-3-yl)-3-fluorobenzoic acid;
4-(1-(2-chloro-6-(trifluoromethyl)benzoyl)-1H-indazol-3-yl)-2-(difluoro methyl)benzoic acid; and
4-(1-(2-chloro-6-(trifluoromethyl)benzoyl)-6-cyano-1H-indazol-3-yl)benzoic acid.

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched.

Unless specified otherwise, "alkyl" includes both branched- and straight-chain saturated aliphatic hydrocarbon groups, including all isomers, having the specified number of carbon atoms; for example, "$C_{1-6}$ alkyl" (or "$C_1$-$C_6$ alkyl") includes all of the hexyl alkyl and pentyl alkyl isomers as well as n-, iso-, sec- and t-butyl, n- and isopropyl, ethyl and methyl. "Alkylene" refers to both branched- and straight-chain saturated aliphatic hydrocarbon groups, including all isomers, having the specified number of carbons, and having two terminal end chain attachments; for example, the term "A-$C_4$alkylene-B" represents, for example, A-$CH_2$—$CH_2$—$CH_2$—$CH_2$—B, A-$CH_2$—$CH_2$—$CH(CH_3)$—$CH_2$—B, A-$CH_2$—$CH(CH_2CH_3)$—B, A-$CH_2$—$C(CH_3)(CH_3)$—B, and the like. "Alkoxy" represents a linear or branched alkyl group of indicated number of carbon atoms attached through an oxygen bridge; for example "$C_1$-$C_6$ alkoxy" includes —$OCH_3$, —$OCH_2CH_3$, —$OCH(CH_3)_2$, —$O(CH_2)_5CH_3$, and the like.

Unless otherwise specifically noted as only "unsubstituted" or only "substituted", alkyl groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, $H_2N$—C(O)(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH ($C_1$-$C_6$ alkyl), NHC(O)O$C_1$-$C_6$ alkyl, —NH($C_1$-$C_6$ alkyl) $NHSO_2(C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "alkenyl" means a straight or branched carbon chain having the specified number of carbon atoms with at least one carbon-carbon double bond. Examples of alkenyl include, but are not limited to, vinyl, allyl, isopropenyl, pentenyl, hexenyl, heptenyl, 1-propenyl, 2-butenyl, 2-methyl-2-butenyl, 2,4-hexadienyl, and the like.

The term "alkynyl" means a straight or branched carbon chain having the specified number of carbon atoms with at least one carbon-carbon triple bond. Examples of alkynyl include, but are not limited to ethynyl, propargyl, 1-propynyl, 2-butynyl, and the like.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either attached via a bond to, or fused (including spirofused) to, the other ring, and each ring is saturated or unsaturated. The carbocycle may be attached to the rest of the molecule at any carbon atom which results in a stable compound.

Saturated carbocyclics form a subset of carbocycles in which the entire ring system (mono- or polycyclic) is saturated. Saturated monocyclic carbocyclic rings are also referred to as cycloalkyl rings, e.g., cyclopropyl, cyclobutyl, etc. The fused bicyclic carbocycles are a further subset of the carbocycles in which a $C_7$ to $C_{10}$ bicyclic ring system in which each ring is saturated or unsaturated and two adjacent carbon atoms (or in the case of spirofused, one carbon atom) are shared by each of the rings in the ring system. A saturated bicyclic carbocycle is one in which both rings are saturated. An unsaturated bicyclic carbocycle is one in which one ring is unsaturated and the other is unsaturated or saturated. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

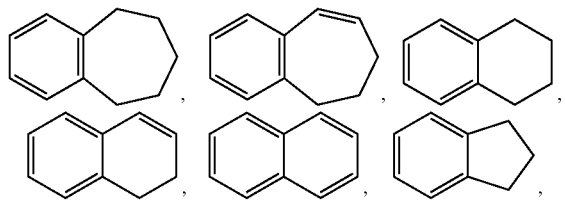

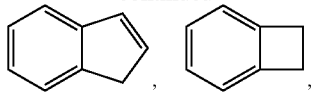

Aromatic carbocycles form another subset of the carbocycles. The term "aryl" refers to aromatic mono- and poly-carbocyclic ring systems in which the individual carbocyclic rings in the polyring systems are fused or attached to each other via a single bond. Suitable aryl groups include phenyl, naphthyl, and biphenyl.

The term "cycloalkyl" means a cyclic ring of an alkane having the specified total ring carbon atoms; for example cyclopropyl, cyclobutyl, cyclopentyl, cyclohexyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is either attached via a bond to, or fused (including spirofused) to, the other ring, and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, 1,4-dioxanyl, 1,4-thioxanyl, tetrahydropyranyl, tetrahydrofuryl (or tetrahydrofuranyl), tetrahydrothienyl, and tetrahydrothiopyranyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic aromatic ring, and which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of monocyclic heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isoxazolyl, oxadiazolyl, thiazolyl, isothiazolyl, and thiadiazolyl. Examples of bicyclic heteroaromatic rings include benzotriazolyl, indolyl, benzoxazolyl, benzofuranyl, benzothienyl, benzothiazolyl, benzimidazolyl, isoindolyl, indazolyl, quinoxalinyl, quinazolinyl, cinnolinyl, quinolinyl, isoquinolinyl, naphthyridinyl, pyrazolo[3,4-b]pyridine, imidazo[2,1-b](1,3)thiazole, (i.e.,

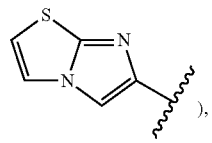

6-(1-pyrrolyl)-3-pyridyl, 4-(1-pyrrolyl)phenyl, 4-(pyrid-3-yl)phenyl, and 4-(pyrid-4-yl)phenyl.

Another subset of heterocycles are unsaturated heterocycles in which one or both rings are unsaturated (provided the entire ring system is not aromatic). Representative examples of unsaturated heterocycles include dihydrofuranyl, dihydrothienyl, dihydropyranyl, dihydroimidazolyl, indolinyl, isoindolinyl, chromanyl, isochromanyl, tetrahydroquinolinyl, tetrahydroisoquinolinyl, tetrahydronaphthyridinyl, 2,3-dihydrobenzofuranyl, 1,4-benzoxazinyl, 1,3-benzoxazolinyl, 2,3-dihydrobenzo-1,4-dioxinyl (i.e.,

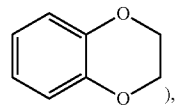

and benzo-1,3-dioxolyl (i.e.,

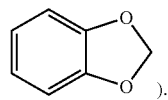

In certain contexts herein,

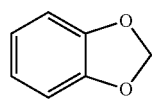

is alternatively referred to as phenyl having as a substituent methylenedioxy attached to two adjacent carbon atoms. Also included are groups such as chromone and coumarin.

Unless otherwise specifically noted as only unsubstituted or only substituted, cycloalkyl, cycloalkenyl, cycloalkyl, aryl (including phenyl) and heteroaryl groups are unsubstituted or substituted (also referred to as "optionally substituted"). Unless the substituents are specifically provided, substituents for substituted or optionally substituted cycloalkyl, cycloalkenyl, aryl (including phenyl, and as an isolated substituent or as part of a substituent such as in aryloxy and aralkyl), heteroaryl (as an isolated substituent or as part of a substituent such as in heteroaryloxy and heteroaralkyl) are one to three groups independently selected from halogen (or halo), $C_1$-$C_6$ alkyl optionally substituted with one to five fluorine, $NH_2$, $N(C_1$-$C_6$ alkyl$)_2$, $NO_2$, oxo, CN, $N_3$, —OH, —O($C_1$-$C_6$ alkyl) optionally substituted with one to five fluorine, $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, aryl-$S(O)_{0-2}$—, ($C_0$-$C_6$ alkyl)$S(O)_{0-2}$($C_0$-$C_6$ alkylene)-, ($C_0$-$C_6$ alkyl)C(O)NH—, $H_2N$—C(NH)—, ($C_0$-$C_6$ alkyl)C(O)—, ($C_0$-$C_6$ alkyl)OC(O)—, ($C_0$-$C_6$alkyl)O($C_1$-$C_6$ alkylene)-, ($C_0$-$C_6$ alkyl)-C(O)$_{1-2}$($C_0$-$C_6$ alkylene)-, ($C_0$-$C_6$ alkyl)$_2$NC(O)—, ($C_0$-$C_6$ alkyl)OC(O)NH—, aryl, aralkyl, heteroaryl, heteroaralkyl, halo-aryl, halo-aralkyl, halo-heteroaryl, halo-heteroaralkyl, cyano-aryl, cyano-aralkyl, cyano-heteroaryl and cyano-heteroaralkyl.

The term "halogen" (or "halo") refers to fluorine, chlorine, bromine and iodine (alternatively referred to as fluoro (F), chloro (Cl), bromo (Br), and iodo (I)).

The term "haloalkyl" means alkyl having the specified number of carbon atoms in which from one to all of the hydrogen atoms have been replaced by a halogen atom.

The terms "aralkyl" and "heteroaralkyl" refer to an aryl/heteroaryl linked to the rest of the molecule via a $C_1$ to $C_4$ alkylene.

The term "$C_0$" as employed in expressions such as "$C_{0-6}$ alkylene" means a direct covalent bond; or when employed in experssions such as "$C_{0-6}$ alkyl" means hydrogen. Similarly, when an integer defining the presence of a certain number of atoms in a group is equal to zero, it means that the atoms adjacent thereto are connected directly by a bond; for example, in the structure

wherein s is an integer equal to zero, 1 or 2, the structure is

when s is zero; or it means that the indicated atom is absent; for example —$S(O)_0$— means —S—.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., (CRiRj)$_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)$_2$ can be

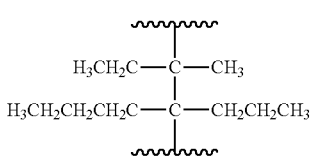

The term $(C_{1-6})$alkyl as used hereinabove means a branched or unbranched alkyl group having 1-6 carbon atoms, for example methyl, ethyl, propyl, isopropyl, butyl, tert-butyl, n-pentyl and n-hexyl. Preferred is $(C_{1-4})$alkyl.

The term $(C_{1-5})$alkyl means a branched or unbranched alkyl group having 1-5 carbon atoms, for example methyl, ethyl, propyl, isopropyl, butyl, tert-butyl and n-pentyl.

The term $(C_{1-4})$alkyl as used herein means a branched or unbranched alkyl group having 1-4 carbon atoms, being methyl, ethyl, n-propyl, isopropyl, n-butyl, isobutyl, sec-butyl and tert-butyl.

The term $(C_{1-3})$alkoxy means an alkoxy group having 1-3 carbon atoms, the alkyl moiety being branched or unbranched.

The term $(C_{1-3})$alkoxycarbonyl means an alkoxycarbonyl group having 1-3 carbon atoms in the alkoxy moiety, the alkoxy moiety having the same meaning as previously defined.

The term $(di)(C_{1-6})$alkylaminocarbonyl means an alkylaminocarbonyl group, the amino group of which is monosubstituted or disubstituted independently with an alkyl group which contains 1-6 carbon atoms and which has the same meaning as previously defined. Preferred alkyl group is $(C_{1-4})$alkyl.

The term $(C_{3-7})$cycloalkyl means a cycloalkyl group having 3-7 carbon atoms, such as cyclopropyl, cyclobutyl, cyclopentyl, cyclohexyl and cycloheptyl. 5-6 Carbon atoms are preferred.

The term $(C_{3-5})$heterocycloalkyl means a heterocycloalkyl group having 3-5 carbon atoms, including 1-3 heteroatoms selected from N, O and/or S, which may be attached via a nitrogen if feasible, or a carbon atom. Preferred number of heteroatoms is one or two. Most preferred number is one. Preferred heteroatoms are N or O. Most preferred are piperazinyl, tetrahydropyranyl, morpholinyl and pyrrolidinyl.

The term $(C_{2-9})$heteroaryl means an aromatic group having 2-9 carbon atoms and 1-3 heteroatoms selected from N, O and S, like imidazolyl, thiadiazolyl, pyridinyl, pyrimidinyl, thiophenyl or furyl, pyrazolyl, isoxazolyl or quinolyl. Preferred number of heteroatoms is one or two. Preferred heteroaryl groups are pyrazolyl, thiophenyl, isoxazolyl, pyridyl and quinolyl. The $(C_{2-5})$heteroaryl group may be attached via a carbon atom or a nitrogen, if feasible.

The term $(C_{6-14})$aryl means an aromatic hydrocarbon group having 6-14 carbon atoms, such as phenyl, naphthyl, tetrahydronaphthyl, indenyl, anthracyl, More preferred are $(C_{6-10})$aryl groups. The most preferred aromatic hydrocarbon group is phenyl.

As used herein, the term "$X_a$-$X_b$", shall have the same meaning as the term "$X_{a-b}$", wherein X is any atom and a and b are any integers. For example, "$C_1$-$C_4$" shall have the same meaning as "$C_{1-4}$". Additionally, when referring to a functional group generically, "A" shall have the same meaning, and be interchangeable with, "AX", wherein "A" is any atom and "x" or "X" are any integer. For example, "$R^1$" shall have the same meaning, and be interchangeable with, "R1".

In the above definitions with multifunctional groups, the attachment point is at the last group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

When, in the definition of a substituent, is indicated that "all of the alkyl groups" of said substituent are optionally substituted, this also includes the alkyl moiety of an alkoxy group.

The term "optionally substituted" means optional substitution with the specified groups, radicals or moieties.

The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The term "effective amount" as used herein, refers to an amount of the compound of Formula (I) and/or an additional therapeutic agent, or a composition thereof, that is effective in producing the desired therapeutic, ameliorative, inhibitory or preventative effect when administered to a subject suffering from an RORgammaT-mediated disease or disorder. In the combination therapies of the present invention, as effective amount can refer to each individual agent or to the combination as a whole, wherein the amounts of all agents administered are together effective, but wherein the component agent of the combination may not be present individually in an effective amount.

A "subject" is a human or non-human mammal. In one embodiment, a subject is a human. In another embodiment, a subject is a chimpanzee It should be noted that any carbon as well as heteroatom with unsatisfied valences in the text, schemes, examples and tables herein is assumed to have the sufficient number of hydrogen atom(s) to satisfy the valences.

The compounds of this invention include the prodrugs, hydrates or solvates of the compounds.

Optical Isomers—Diastereomers—Geometric Isomers—Tautomers

The compounds of Formula I may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula (I) may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzyl-ethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

The compounds of Formula I can form salts which are also within the scope of this invention. Reference to a compound of Formula I herein is understood to include reference to salts thereof, unless otherwise indicated.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide, calcium hydroxide, calcium carbonate, ammonium (e.g. diethylamine) or lithium hydroxide.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

The compounds of the invention may form hydrates or solvates. It is known to those of skill in the art that charged compounds form hydrated species when lyophilized with water, or form solvated species when concentrated in a solution with an appropriate organic solvent. One or more compounds of the invention may exist in unsolvated as well as solvated forms with pharmaceutically acceptable solvents such as water, ethanol, and the like, and it is intended that the invention embrace both solvated and unsolvated forms. "Solvate" may also mean a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs

The present invention includes within its scope the use prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of Retinoic Acid Receptor-related Orphan Receptor gamma t (RORgammaT), and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound having Formula I, Ia, Ib, Ic, Id or Ie or a pharmaceutically acceptable salt or solvate thereof, that is effective for treating the disease or condition mediated by RORgammaT in the subject.

The compounds according to the invention can be used in therapy.

A further aspect of the invention resides in the use of compounds according to the invention or a pharmaceutically acceptable salt thereof for the treatment of RORgammaT-mediated diseases or RORgammaT mediated conditions.

Another aspect of the invention resides in the use of compounds or a pharmaceutically acceptable salt thereof having the general formula I for the treatment of autoimmune diseases, in particular those diseases in which Th17 cells and non-Th17 cells, which express Th17 hallmark cytokines play a prominent role. These include, but are not limited to, the treatment of rheumatoid arthritis, psoriasis, inflammatory bowel disease, Crohn's disease and multiple sclerosis.

In another aspect, compounds or a pharmaceutically acceptable salt thereof having the general formula I can be used for treatment of inflammatory diseases in which Th17 cells and/or non-Th17 cells, which express Th17 hallmark cytokines play a prominent role such as, but not limited to respiratory diseases, osteoarthritis and asthma. Also, compounds or a pharmaceutically acceptable salt thereof having the general formula I can be used for treatment of infectious diseases in which Th17 cells and/or non-Th17 cells, which express Th17 hallmark cytokines play a prominent role such as, but not limited to mucosal leishmaniasis.

Compounds or a pharmaceutically acceptable salt thereof having the general formula I can also be used for treatment of other diseases in which Th17 cells and/or non-Th17 cells, which express Th17 hallmark cytokines play a prominent role such as, but not limited to Kawasaki disease and Hashimoto's thyroiditis.

In one aspect is the disease or condition is an autoimmune disease or inflammatory disease. The disease or condition includes, but is not limited to, multiple sclerosis, inflammatory bowel disease, Crohn's disease, psoriasis, rheumatoid arthritis, asthma, osteoarthritis, Kawasaki disease, Hashimoto's thyroiditis or mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis and mucosal leishmaniasis.

In another aspect the compounds according to the invention can be used to treat or prevent psoriasis.

In yet another aspect the compounds according to the invention can be used to treat inflammatory bowel disease.

This aspect of the present invention further includes the use of a compound of Formula I, Ia, Ib, Ic, Id or Ie, or a pharmaceutically acceptable salt or solvate thereof, in the manufacture of a medicament for the treatment of a disease or condition mediated by RORgammaT.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., autoimmune and inflammatory diseases and disorders.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula I or a pharmaceutically acceptable salt or solvate thereof and one or more pharmaceutically acceptable excipients. The term "excipient" and "carrier" may be used interchangeably.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy. The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The present invention also relates to a pharmaceutical composition comprising compounds or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of the present invention, and their salts and solvates, and physiologically functional derivatives thereof, may be employed alone or in combination with other therapeutic agents for the treatment of diseases and conditions associated with inappropriate IL-17 pathway activity. Combination therapies according to the present invention thus comprise the administration of at least one compound of formula (I) or a pharmaceutically acceptable salt or solvate thereof, or a physiologically functional derivative thereof, and the use of at least one other pharmaceutically active agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect. For the treatment of the inflammatory and autoimmune diseases, rheumatoid arthritis, psoriasis, inflammatory bowel disease, SLE, uveitis, atopic dermatitis, COPD, asthma and allergic rhinitis a compound of formula (I) may be combined with one or more other active agents such as: (1) TNF-a inhibitors; (2) non-selective COX-I/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. It could also be combined with anti-IL17 antibodies to obtain additive/synergistic responses for the treatment of inflammatory and autoimmune diseases.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula I, Ia, Ib, Ic, Id or Ie.

The invention further includes a compound of Formula I in combination with one or more other drug(s).

Synthesis

Table 1 below lists commercial sources, and previously disclosed synthetic routes, for chemical materials employed in the synthesis of intermediates and examples of the instant invention. This list is not intended to be exhaustive, exclusive, or limiting in any way.

TABLE 1

| Structure | Source |
|---|---|
|  | Oakwood |
| 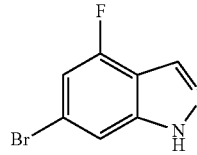 | Aldrich |
| 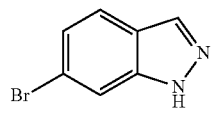 | Frontier |
| 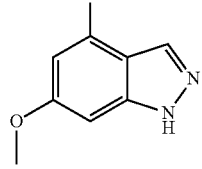 | Oakwood |

TABLE 1-continued

| Structure | Source |
|---|---|
| 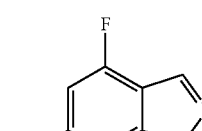 | Sinova |
| 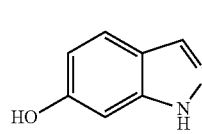 | Sinova |
| 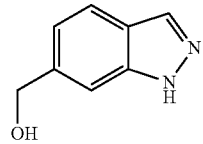 [SMILES: OCc1ccc2cn[nH]c2c1] | Aldrich |
| 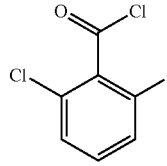 | Sinova |
| 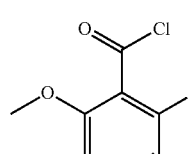 | Sinova |
| | Aldrich |
| | Sinova |
| 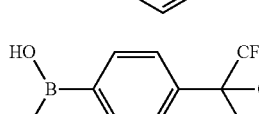 | Alfa |
| | Alfa |
| 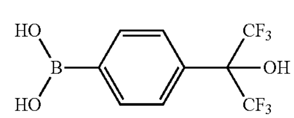 | *Bioorganic & Medicinal Chemistry Letters*, 2006, 695-700 |

TABLE 1-continued

| Structure | Source |
|---|---|
| (3-methoxycarbonylphenyl)boronic acid | Acros |
| methyl 2-(3-boronophenyl)acetate | Combi-blocks |
| methyl 2-(4-boronophenyl)acetate | Combi-blocks |
| methyl 2-chloro-4-boronobenzoate | Alfa |
| methyl 3-chloro-4-boronobenzoate | Combi-blocks |
| 4-boronobenzamide | Alfa |
| methyl 4-borono-2-methylbenzoate | Combi-blocks |
| methyl 4-borono-2-methoxybenzoate | Combi-blocks |
| methyl 4-borono-2-fluorobenzoate | Alfa |
| 4-borono-2-methylbenzoic acid | Combi-blocks |
| methyl 4-borono-3-methoxybenzoate | Anichem |
| methyl 4-borono-2,6-difluorobenzoate | Aobchem |

TABLE 1-continued

| Structure | Source |
|---|---|
| 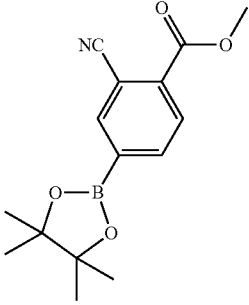 | Chemmaker |
| 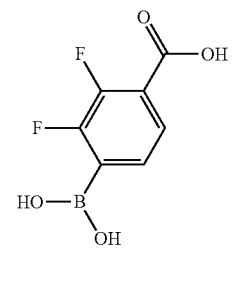 | Combi-blocks |
| 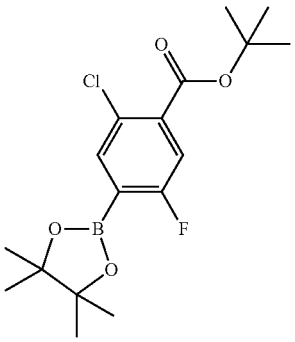 [SMILES: CC(C)(C)OC(=O)c1cc(F)c(B2OC(C)(C)C(C)(C)O2)cc1Cl] | Combi-blocks |
| 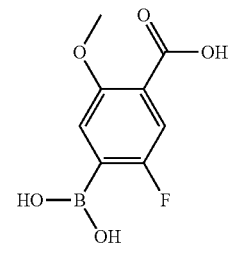 | Anisyn |
| 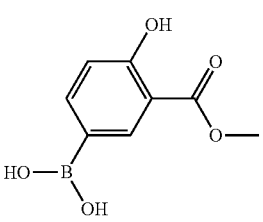 | Anisyn |
| 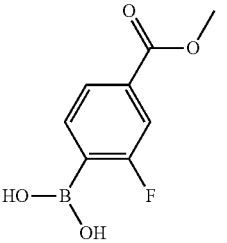 | Alfa |
| 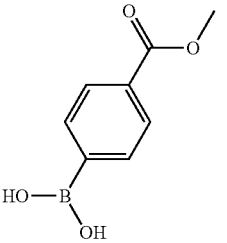 | Aldrich |

Abbreviations used herein are as follows: Boc: tert-butoxycarbonyl; $CDCl_3$: chloroform-d; DiPEA: N,N-diisopropylethylamine; DMAP: 4-dimethylaminopyridine; DMF: N,N-dimethylformamide; $Et_3N$ or TEA: triethyl amine; HPLC: high performance liquid chromatography; TFA: trifluoro acetic acid; MS: mass spectrum; $(PPh_3)_4Pd$: tetrakis-(triphenylphosphine)palladium(0); THF: tetrahydrofuran; TLC: thin layer chromatography; $SiO_2$: silica-gel; DME: dimethoxy ethane; m: molar; t-BuOK; potassium tert-butoxide; APCI-MS: atmospheric pressure chemical ionization mass spectrometry; ESI-MS; electronspray ionization-mass spectroscopy; EtOAc: Ethyl acetate; PE: Petroleum ether; EA: Ethyl acetate; DCM: Dichloro methane; Dppf: 1,1.Bis (diphenylphosphino)ferrocene; AcOH:Acetic acid; DMAC: N,N-Dimethylacetamide; PYAOP: (7-Azabenzotriazol-1-yloxy)tripyrrolidin ophosphonium hexafluorophosphate; $Pd(dppf)Cl_2$: [1,1'-Bis(diphenylphosphino) ferrocene] dichloropalladium (II); BnBr: Benzyl bromide; DAST: (Diethylamino)sulfur trifluoride; $Ac_2O$: Acetic an hydride; LiHMDS: Lithium bis(trimethylsilyl)amide; $PhNTf_2$: N-Phenyl-bis(trifluoro methanesulfonimide); S-Phos: 2-Dicyclohexylphosphino-2',6'-dimethoxybiphenyl; X-Phos: 2-Dicyclohexylphosphino-2',4',6'-triisopropylbiphenyl; CPME: Cyclopentyl methyl ether.

Intermediates

EXAMPLE i-1

Preparation of methyl 2-isopropyl-4-(4,4,5,5-tetramethyl-1,3,2-dioxaborolan-2-yl)benzoate (i-1)

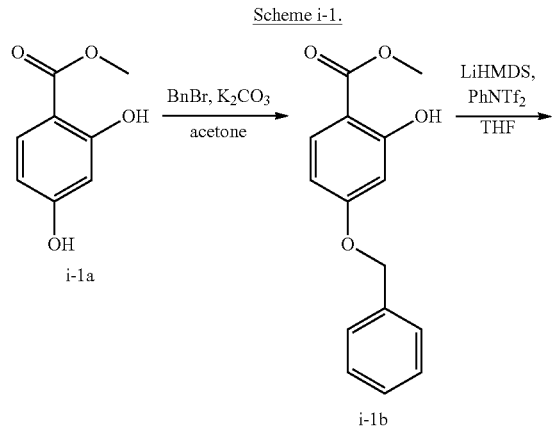

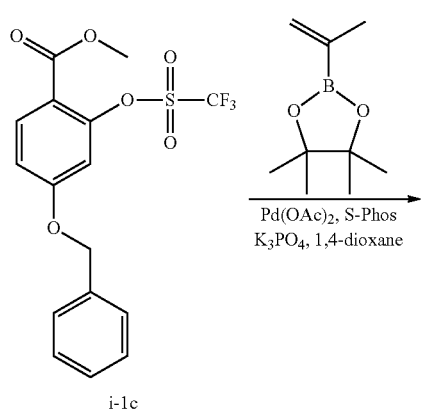

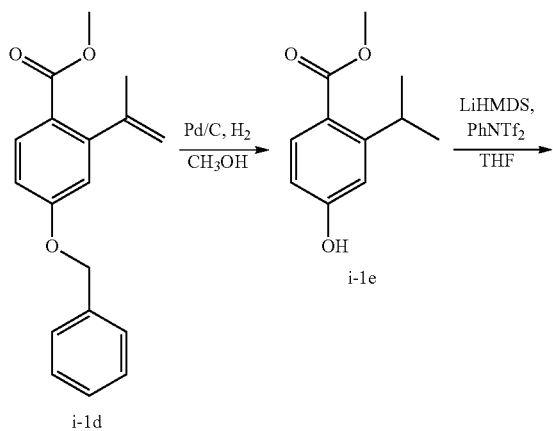

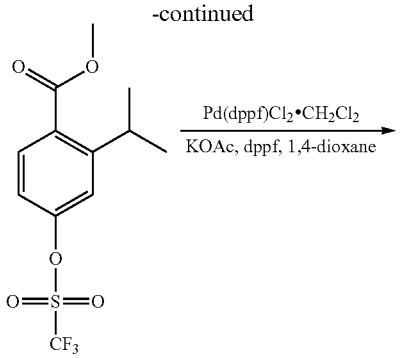

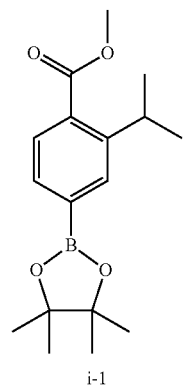 [SMILES: COC(=O)c1ccc(B2OC(C)(C)C(C)(C)O2)cc1C(C)C]

i) Preparation of methyl 4-(benzyloxy)-2-hydroxybenzoate (i-1b)

To a solution of methyl 2,4-dihydroxybenzoate (i-1a) (1.68 g, 10 mmol) in acetone (30 mL) was added K$_2$CO$_3$ (2.76 g, 20 mmol). The mixture was stirred at rt for 5 h, followed by the addition of BnBr (1.88 g, 11 mmol). The mixture was heated at 60° C. for 24 h. The reaction mixture was cooled down, filtered. The filtrate was concentrated to afford the title compound. LCMS (ESI) calc'd for C$_{15}$H$_{14}$O$_4$ [M+H]$^+$: 259.1. found: 259.1.

ii) Preparation of methyl 4-(benzyloxy)-2-(trifluoromethylsulfonyloxy)benzoate (i-1c)

To a solution of methyl 4-(benzyloxy)-2-hydroxybenzoate (i-1b) (1.1 g, 4.26 mmol) in THF (20 ml) at −78° C. was added LiHMDS (1M in THF, 5.1 ml, 5.1 mmol) dropwise. Then the mixture was warmed up to −40° C. and stirred at this temperature for 3 h. PhNTf$_2$ (1.52 g, 4.26 mmol) was added, and the mixture was stirred at rt for 24 h. The mixture was then diluted with H$_2$O, and extracted with EtOAc. The organic layer was dried, concentrated, and purified by flash chromatography (PE/EA=10:1) to afford the title compound. LCMS (ESI) calc'd for C$_{16}$H$_{13}$F$_3$O$_6$S [M+H]$^+$: 391. found: 391.

iii) Preparation of methyl 4-(benzyloxy)-2-(prop-1-en-2-yl)benzoate (i-1d)

Methyl 4-(benzyloxy)-2-(trifluoromethylsulfonyloxy) benzoate (i-1c) (6.8 g, 17.4 mmol), 4,4,5,5-tetramethyl-2-(prop-1-en-2-yl)-1,3,2-dioxaborolane (2.9 g, 17.4 mmol), Pd(OAc)$_2$ (195 mg, 0.87 mmol), S-Phos (71 mg, 0.174 mmol) and K$_3$PO$_4$ (11 g, 52 mmol) were mixed in THF (70 ml). The mixture was stirred at 75° C. for 24 h. The mixture was diluted with H₂O, and extracted with EtOAc. The combined organics were dried and concentrated. The residue was purified by flash chromatography (PE/EA=10:1) to afford the title compound. LCMS (ESI) calc'd for $C_{18}H_{18}O_3$ [M+H]⁺: 391. found: 391.

iv) Preparation of methyl 4-hydroxy-2-isopropylbenzoate (i-1e)

To a solution of methyl 4-(benzyloxy)-2-(prop-1-en-2-yl) benzoate (i-1d) (4.6 g, 16.3 mmol) in methanol (100 ml) was added Pd/C (0.46 g). The mixture was stirred at rt under H₂ atmosphere for 24 h. Then the mixture was filtered, and the filtrate was concentrated to afford the title compound. LCMS (ESI) calc'd for $C_{11}H_{14}O_3$ [M+H]⁺: 195.1. found: 195.1.

v) Preparation of methyl 2-isopropyl-4-(trifluoromethylsulfonyloxy)benzoate (i-1f)

To a solution of methyl 4-hydroxy-2-isopropylbenzoate (i-1e) (2.45 g, 12.6 mmol) in THF (100 ml) at −78° C. was added LiHMDS (1M in THF, 15 ml, 15 mmol) dropwise. Then the mixture was warmed up to −40° C. and stirred for 3 h. PhNTf₂ (4.5 g, 12.6 mmol) was added and the mixture was stirred at rt for 24 h. The reaction mixture was diluted with H₂O and extracted with EtOAc. The organic layer was dried and concentrated. The residue was purified by flash chromatography (PE/EA=8:1) to afford the title compound. LCMS (ESI) calc'd for $C_{12}H_{13}F_3O_5S$ [M+H]⁺: 327. found: 327.

vi) Preparation of methyl 2-isopropyl-4-(4,4,5,5-tetramethyl-1,3,2-dioxaborolan-2-yl)benzoate (i-1)

Methyl 2-isopropyl-4-(trifluoromethylsulfonyloxy)benzoate (i-1f) (1.5 g, 4.6 mmol), 4,4,4',4',5,5,5',5'-octamethyl-2,2'-bi(1,3,2-dioxaborolane) (1.75 g, 6.9 mmol), Pd(dppf)Cl₂.CH₂Cl₂ (188 mg, 0.23 mmol), dppf (102 mg, 0.184 mmol) and KOAc (1.13 g, 11.5 mmol) were mixed in 1,4-dioxane (35 ml). The mixture was stirred at 80° C. for 24 h. The mixture was then cooled down and concentrated under reduced pressure. The residue was diluted with H₂O, extracted with EtOAc. The combined organics were dried and concentrated. The residue was purified by flash chromatography (PE/EA=10:1) to afford the title compound. LCMS (ESI) calc'd for $C_{17}H_{25}BO_4$ [M+H]⁺: 305.2. found: 305.2.

EXAMPLE i-2

Preparation of methyl 2-fluoro-5-methyl-4-(4,4,5,5-tetramethyl-1,3,2-dioxaborolan-2-yl)benzoate (i-2)

Scheme i-2.

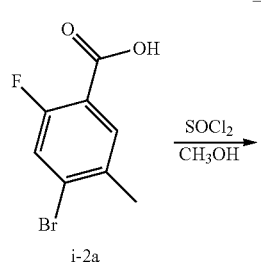

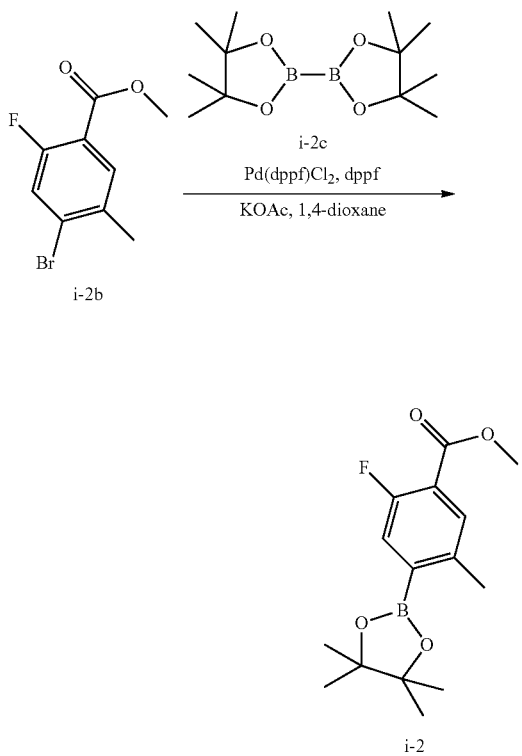

i) Preparation of methyl 4-bromo-2-fluoro-5-methylbenzoate (i-2b)

To a solution of 4-bromo-2-fluoro-5-methylbenzoic acid (i-2a) (1.87 g, 8 mmol) in CH₃OH (50 mL) at 0° C. was added SOCl₂ (6 mL, 80 mmol) dropwise. Then the mixture was heated to 80° C. for 2 h. The solvent was removed in vacuo and the residue was diluted with EtOAc and washed with H₂O, brine, dried over anhydrous Na₂SO₄, and concentrated. The resulting crude solid was washed with PE to give the title compound as a yellow solid. ¹H NMR (400 MHz, CDCl₃) δ 7.80 (1H, d), 7.37 (1H, d), 3.92 (3H, s), 2.39 (3H, s).

ii) Preparation of methyl 2-fluoro-5-methyl-4-(4,4,5,5-tetramethyl-1,3,2-dioxa borolan-2-yl)benzoate (i-2)

To a flask was added compound (i-2b) (830 mg, 3.3 mmol), compound (i-2c) (915 mg, 3.6 mmol), dppf (25 mg, 0.132 mmol), Pd(dppf)Cl₂*CH₂Cl₂ (134 mg, 0.165 mmol) and 1,4-dioxane (20 mL). The reaction mixture was heated at 80° C. for 2 h. The mixture was diluted with H₂O, and the organic layer was separated. The aqueous layer was extracted with CH₂Cl₂. The combined organics were washed with H₂O and brine, dried over Na₂SO₄, and concentrated. The residue was purified by flash chromatography (Pentane/EtOAc) to afford the title compound. LCMS (ESI) calc'd for $C_{15}H_{20}BFO_4$ [M+H]⁺: 295.1. found: 295.1.

EXAMPLE i-3

Preparation of methyl 3,5-dimethoxy-4-(4,4,5,5-tetramethyl-1,3,2-dioxaborolan-2-yl)benzoate (i-3)

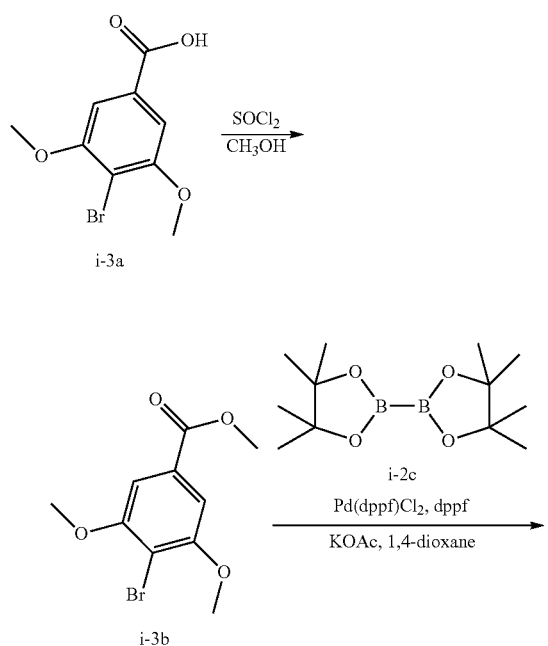

i) Preparation of methyl 4-bromo-3,5-dimethoxybenzoate (i-3b)

Prepared following a similar procedure of compound i-2b LCMS (ESI) calc'd for $C_{10}H_{11}BrO_4$ [M+H]$^+$: 275.1. found: 275.1.

ii) Preparation of methyl 3,5-dimethoxy-4-(4,4,5,5-tetramethyl-1,3,2-dioxa borolan-2-yl)benzoate (i-3)

Prepared following a similar procedure of compound i-2 LCMS (ESI) calc'd for $C_{16}H_{23}BrO_6$ [M+H]$^+$: 323.2. found: 323.2.

EXAMPLE i-4

Preparation of methyl 2,5-difluoro-4-(4,4,5,5-tetramethyl-1,3,2-dioxaborolan-2-yl)benzoate (i-4)

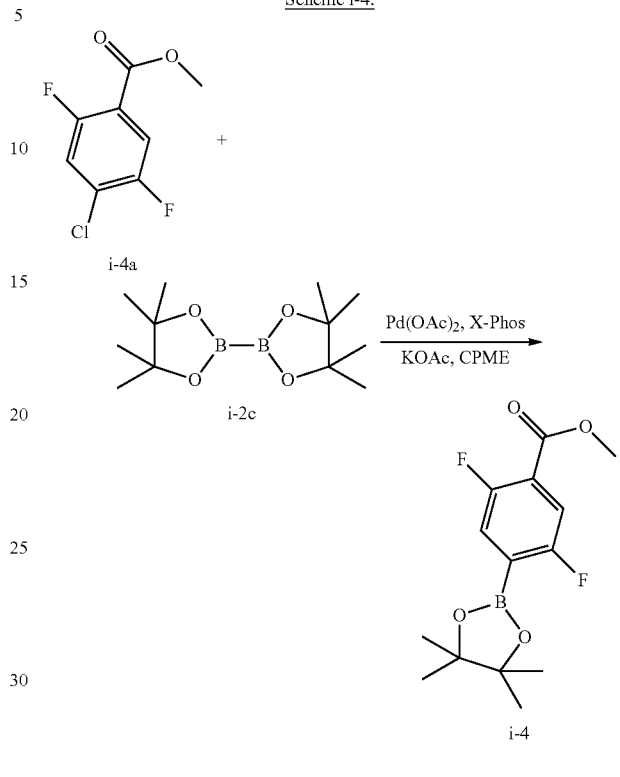

i) Preparation of methyl 2-fluoro-5-methyl-4-(4,4,5,5-tetramethyl-1,3,2-dioxa borolan-2-yl)benzoate (i-4)

To a flask was added compound (i-4a) (412 mg, 2.0 mmol), compound (i-2c) (1.52 g, 6 mmol), X-Phos (95 mg, 0.2 mmol), Pd(OAc)$_2$ (44 mg, 0.2 mmol) and CPME (20 mL). The reaction mixture was heated at 85° C. for 2 h. The mixture was then cooled down, diluted with H$_2$O, and the organic layer was separated. The aqueous layer was extracted with Et$_2$O. The combined organics were washed with H$_2$O and brine, dried over Na$_2$SO$_4$, and concentrated. The residue was purified by flash chromatography (DCM) to afford the title compound. LCMS (ESI) calc'd for $C_{14}H_{17}BF_2O_4$ [M+H]$^+$: 299.1. found: 299.1.

EXAMPLE i-5

Preparation of 3-fluoro-5-methoxy-4-(methoxycarbonyl)phenyl boronic acid (i-5)

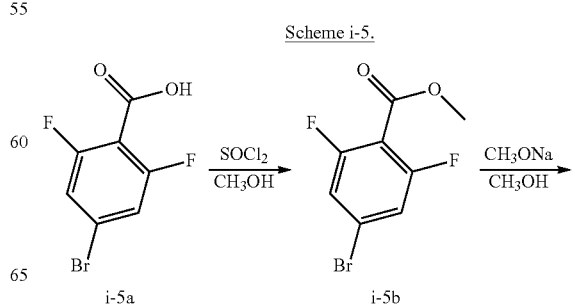

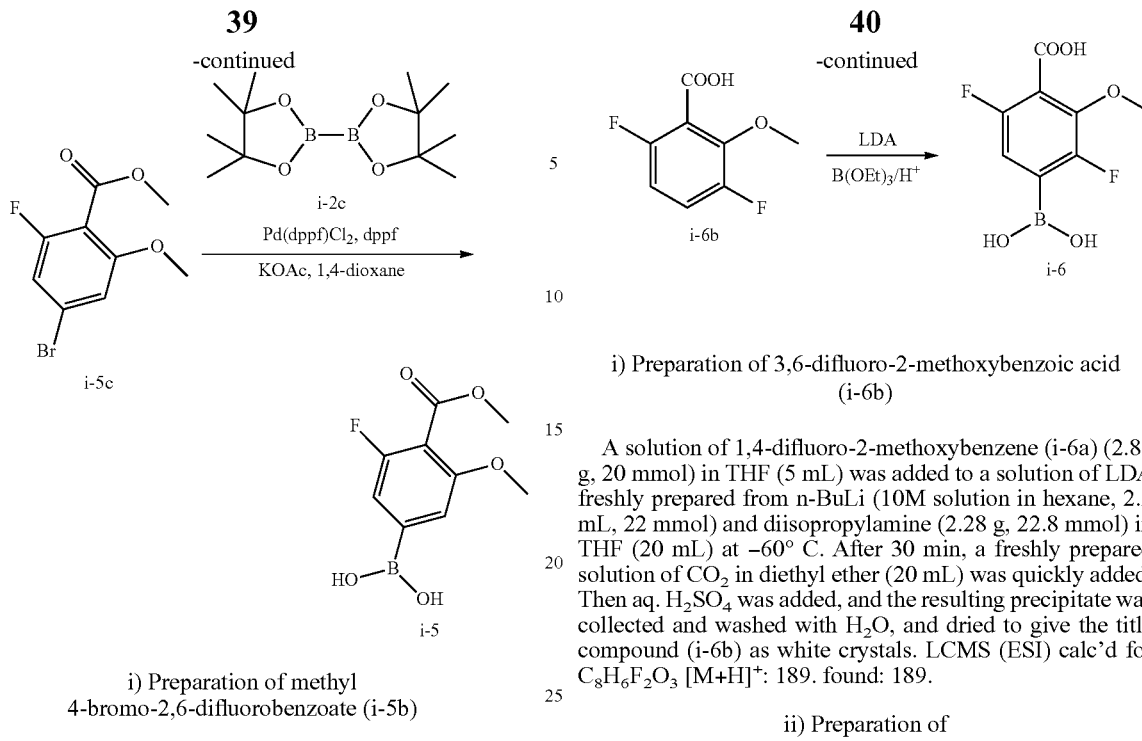

i) Preparation of 3,6-difluoro-2-methoxybenzoic acid (i-6b)

A solution of 1,4-difluoro-2-methoxybenzene (i-6a) (2.88 g, 20 mmol) in THF (5 mL) was added to a solution of LDA freshly prepared from n-BuLi (10M solution in hexane, 2.2 mL, 22 mmol) and diisopropylamine (2.28 g, 22.8 mmol) in THF (20 mL) at −60° C. After 30 min, a freshly prepared solution of $CO_2$ in diethyl ether (20 mL) was quickly added. Then aq. $H_2SO_4$ was added, and the resulting precipitate was collected and washed with $H_2O$, and dried to give the title compound (i-6b) as white crystals. LCMS (ESI) calc'd for $C_8H_6F_2O_3$ [M+H]$^+$: 189. found: 189.

ii) Preparation of 4-borono-3,6-difluoro-2-methoxybenzoic acid (i-6)

To a solution of 3,6-difluoro-2-methoxybenzoic acid (i-6b) (0.94 g, 5 mmol) in THF (5 mL) at −70° C. was added a solution of LDA [freshly prepared from diisopropylamine (1.51 g, 15 mmol) and n-BuLi (10M solution in hexane, 1.5 mL, 15 mol) in THF (15 mL). The resultant solution was stirred for 15 mins, followed by the addition of B(OEt)$_3$ (1.46 g, 10 mmol). The mixture was stirred for 15 mins and then hydrolyzed with dilute aq. $H_2SO_4$. The organic phase was separated and the aqueous layer was extracted with $Et_2O$. The combined organics were concentrated and the residue solid was washed with $H_2O$ and hexane, dried to give the title compound as white crystals. LCMS (ESI) calc'd for $C_8H_7BF_2O_5$ [M+H]$^+$: 233. found: 233.

EXAMPLE i-7: methyl 5-fluoro-2-methoxy-4-(4,4,5,5-tetramethyl-1,3,2-dioxa borolan-2-yl)benzoate (i-7)

i) Preparation of methyl 4-bromo-2,6-difluorobenzoate (i-5b)

Prepared following a similar procedure of compound i-2b
LCMS (ESI) calc'd for $C_8H_5BrF_2O_2$ [M+H]$^+$: 250.9. Found: 250.9.

ii) Preparation of methyl 4-bromo-2-fluoro-6-methoxybenzoate (i-5c)

To a solution of compound (i-5b) (827 mg, 3.3 mmol) in DMF (20 mL) at 0° C. was added a solution of sodium methoxide (25% in MeOH, 0.75 mL, 3.3 mmol). The reaction mixture was stirred at 0° C. for 10 min and then at rt for 30 min. The mixture was then brought back to 0° C. and quenched with EtOAc and 1M HCl. The organic layer was separated and the aqueous phase was extracted with EtOAc. The combined organics were dried over $Na_2SO_4$ and concentrated. The crude oil was purified by flash chromatography (Pentane/EtOAc) to afford the title compound. LCMS (ESI) calc'd for $C_9H_8BrFO_3$ [M+H]$^+$: 263.0. found: 263.0; $^1$H NMR (400 MHz, CDCl$_3$) δ 6.98 (1H, t), 6.91 (1H, q), 3.76 (3H, s), 3.74 (3H, s).

ii) Preparation of 3-fluoro-5-methoxy-4-(methoxycarbonyl)phenylboronic acid (i-5)

Prepared following a similar procedure of compound i-2
LCMS (ESI) calc'd for $C_9H_{10}BFO_5$ [M+H]$^+$: 229.1. found: 229.1.

Example i-6: Preparation of 4-borono-3,6-difluoro-2-methoxybenzoic acid (i-6)

Scheme i-6.

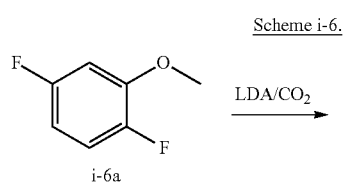

Scheme I-7.

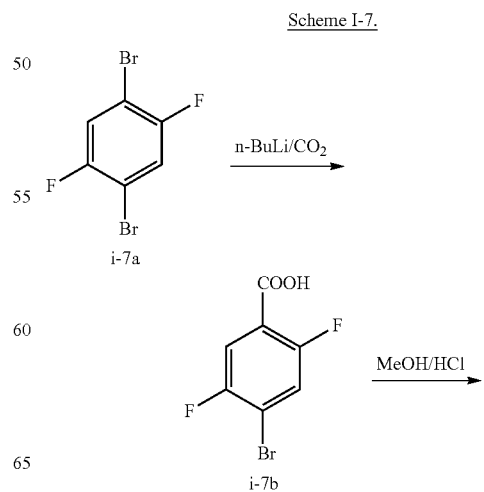

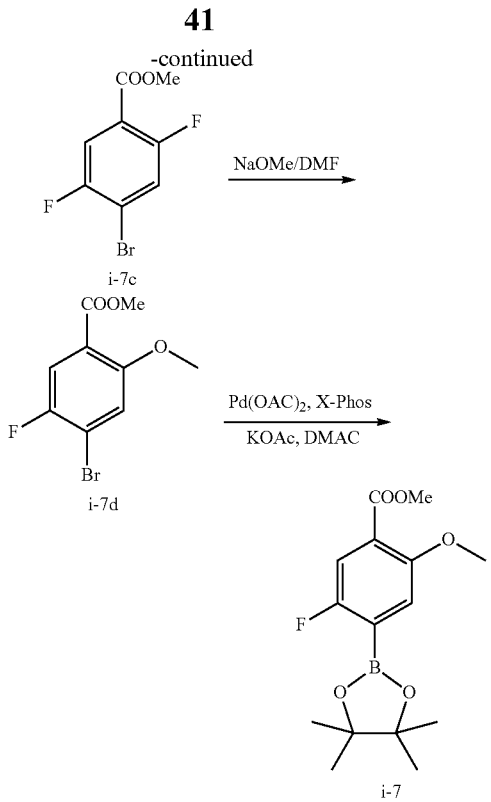

i) Preparation of 4-bromo-2,5-difluorobenzoic acid (i-7b)

To a solution of 1,4-dibromo-2,5-difluorobenzene (i-7a) (1.1 g, 4 mmol) in Et$_2$O (10 mL) at −78° C. was added n-BuLi (2.5M in hexane, 1.6 mL, 4 mmol) dropwise. The mixture was stirred for 30 min at −78° C. and then quenched with an excess of freshly crushed dry ice. After 15 min, the mixture was brought to rt and diluted with H$_2$O. The aqueous layer was separated, and the organic layer was extracted with 10% aq. Na$_2$CO$_3$. The combined aqueous layers were acidified with 1M HCl and extracted with EtOAc. The combined organic layers were dried with Na$_2$SO$_4$ and concentrated to give the title compound. LCMS (ESI) calc'd for C$_7$H$_3$BrF$_2$O$_2$ [M+H]$^+$: 237. found: 237.

ii) Preparation of methyl 4-bromo-2,5-difluorobenzoate (i-7c)

A mixture of 4-bromo-2,5-difluorobenzoic acid (i-7b) (0.48 g, 2 mmol) and methanol (10 mL, saturated with gaseous HCl) was heated at 65° C. for 2 h. The mixture was concentrated. Then MeOH was added and the mixture was concentrated again. The residue was purified by flash chromatography (Pentane/EtOAc=4:1) to give the title compound. LCMS (ESI) calc'd for C$_8$H$_5$BrF$_2$O$_2$ [M+H]$^+$: 251. found: 251.

iii) Preparation of methyl 4-bromo-5-fluoro-2-methoxybenzoate (i-7d)

To a solution of methyl 4-bromo-2,5-difluorobenzoate (i-7c) (0.5 g, 2 mmol) in DMF (5 mL) at 0° C. was added NaOMe (25% in MeOH, 0.45 mL, 2 mmol). The reaction mixture was stirred at 0° C. for 10 min and then at rt for 30 min. The mixture was then brought back to 0° C. and quenched with EtOAc and 1M HCl. The organic layer was separated, and the aqueous phase was extracted with EtOAc, dried over Na$_2$SO$_4$, concentrated and purified by flash chromatography (Pentane/EtOAc=9:1) to give the title compound. LCMS (ESI) calc'd for C$_9$H$_8$BrFO$_3$ [M+H]$^+$: 263. found: 263 iv) Preparation of methyl 5-fluoro-2-methoxy-4-(4,4,5,5-tetramethyl-1,3,2-dioxaborolan-2-yl)benzoate (i-7)

A mixture of Bis(pinacolato)diboron (0.72 g, 2.86 mmol), Pd(OAc)$_2$ (50 mg), X-Phos (100 mg), methyl 4-bromo-5-fluoro-2-methoxybenzoate (i-7d) (0.5 g, 1.9 mmol), and KOAc (100 mg) in DMAC (20 mL) were heated at 80° C. for 24 h. The mixture was then cooled down, diluted with EtOAc and H$_2$O. The organic layer was separated and the aqueous layer was extracted with EtOAc. The organics were combined, dried, concentrated and purified by flash chromatography (Pentane/EtOAc=10:1) to give the title compound. LCMS (ESI) calc'd for C$_{15}$H$_{20}$BFO$_5$ [M+H]$^+$: 311. found: 311

EXAMPLE i-8

Preparation of (2-chloro-6-(trifluoromethyl)phenyl)(3-iodo-6-(methoxymethyl)-1H-indazol-1-yl)methanone (i-8)

Scheme I-8.

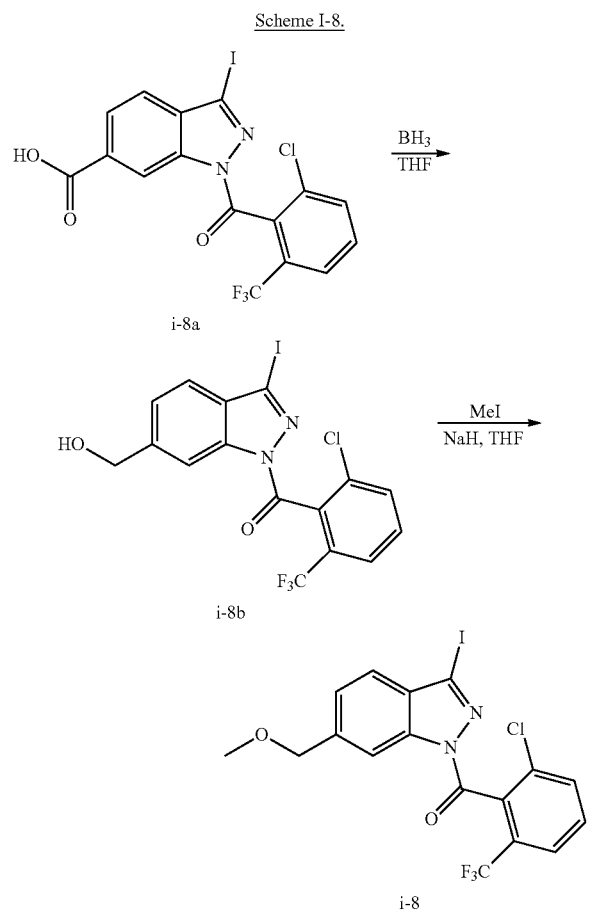

i) Preparation of (2-chloro-6-(trifluoromethyl)phenyl)(6-(hydroxymethyl)-3-iodo-1H-indazol-1-yl)methanone (i-8b)

To a solution of compound (i-8a) (prepared following the procedure of Scheme D) (175 mg, 0.35 mmol) in THF (20 mL) was added BH$_3$.THF (1.75 mL, 1.75 mmol) and the mixture was refluxed for 12 h. The mixture was cooled down and quenched with excess MeOH. The mixture was concentrated to give the title compound. LCMS (ESI) calc'd for $C_{16}H_9ClF_3IN_2O_2$ [M+H]$^+$: 480.9. found: 480.9.

ii) Preparation of (2-chloro-6-(trifluoromethyl)phenyl)(3-iodo-6-(methoxy methyl)-1H-indazol-1-yl)methanone (i-8)

To a mixture of (i-8b) (0.2 g, 0.416 mmol) in THF (5 mL) was added NaH (25 mg, 0.62 mmol) and the mixture was stirred at room temperature for 30 min. Then iodomethane (0.1 mL, 0.83 mmol) was added dropwise. The reaction mixture was stirred at rt for 24 h. Ammonium Hydroxide (5 mL) was added to quench the reaction. The solvent was removed under reduced pressure and the residue was diluted with aq. NH$_4$Cl.

The mixture was extracted with EtOAc, and the combined organics were washed with brine, dried over anhydrous Na$_2$SO$_4$ and concentrated. The residue was purified by prep-TLC (PE:EA 4:1) to provide the title compound as a pale yellow solid. LCMS (ESI) calc'd for $C_{17}H_{11}ClF_3IN_2O_2$ [M+H]$^+$: 495. found: 495.

Method for Preparing Compounds of the Invention

Methods for preparing the compounds of this invention are illustrated in the following schemes. Other synthetic protocols will be readily apparent to those skilled in the art. The examples illustrate the preparation of the compounds of Formula I and as such are not to be considered as limiting the invention set forth in the claims appended hereto. Unless otherwise indicated, all variables are as previously defined.

compounds I. In a typical procedure, a mixture of compound II, a palladium catalyst (e.g. Pd(PPh$_3$)$_4$), base (e.g. aqueous NaOH, K$_2$CO$_3$ or the like) and an aryl boronic acid of general Formula III-a or aryl boronic ester of general formula III-b in a suitable solvent such as dioxane or toluene/EtOH, is heated under an atmosphere of nitrogen under microwave irradiation or using conventional heating.

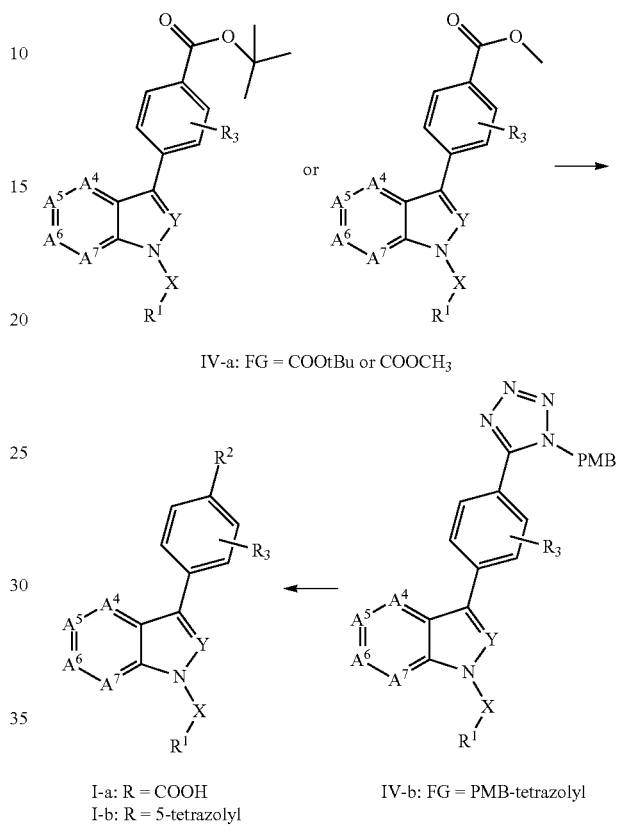

SCHEME 1

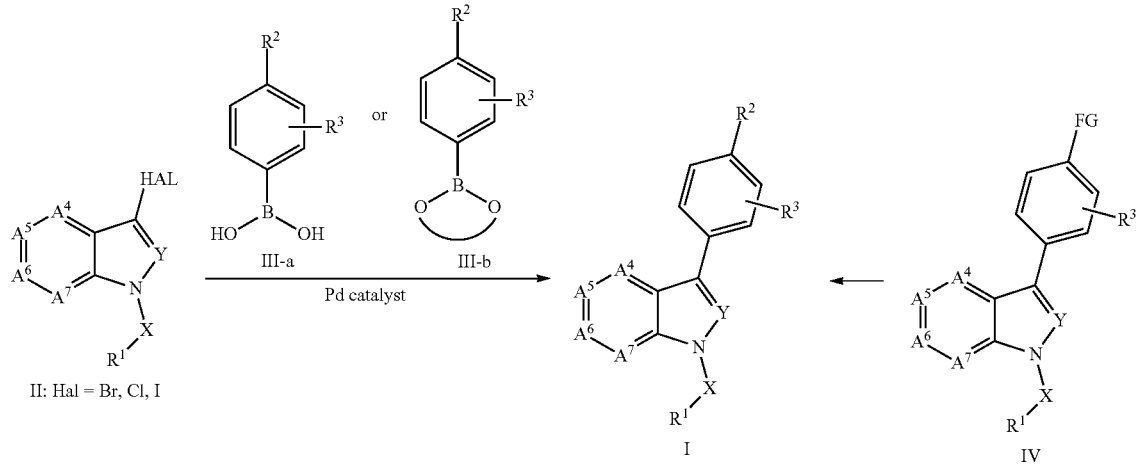

The heterocyclic derivatives of Formula I, wherein A$^4$ to A$^7$, R$^1$, R$^2$, R$^3$, X and Y are as previously defined, can be prepared from compounds II. Palladium catalyzed Suzuki-Miyaura arylation of compounds II using appropriately substituted phenylboronic acids III-a (corresponding boronic esters III-b may also be used) directly affords the desired Alternatively, compound I may be obtained from compounds of Formula IV, in which FG is a functional group (e.g. ester, cyano, protected tetrazole) that can be easily converted to groups defined for R$^2$. Non limiting examples of suitable functional groups in compounds IV are a tert-butyl ester or methyl ester or a tetrazole, containing an acid labile group such as a para-methoxy benzyl protecting group, which can be treated with acid or base to afford compounds of Formula I-a or I-b in which $R^2$ is carboxyl or 5-tetrazolyl, respectively.

Compounds IV can be prepared in the same way as compounds I, by Suzuki-Miyaura reaction between compounds of general Formula II and an appropriately substituted arylboronic acid or ester.

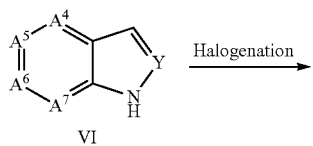

VI

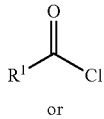

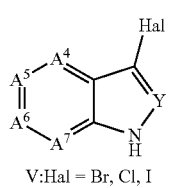

V: Hal = Br, Cl, I

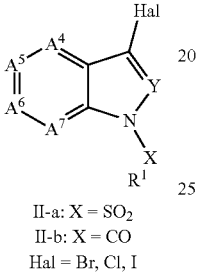

II-a: X = SO$_2$
II-b: X = CO
Hal = Br, Cl, I

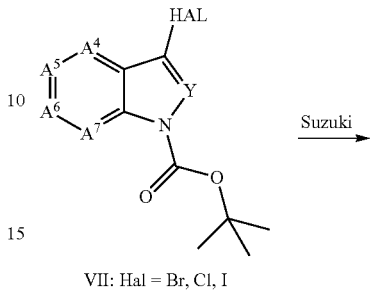

VII: Hal = Br, Cl, I

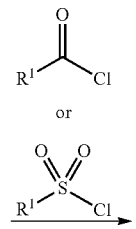

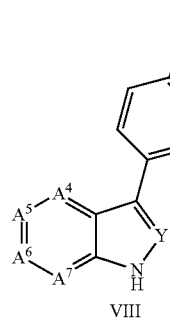

VIII

Compounds II are prepared by straightforward acylation or sulfonylation of compounds V. For example, treatment of compounds V with a strong base (such as potassium tert-butoxide or NaH) and the appropriately substituted sulfonyl chlorides in a suitable solvent such as DMF or THF will give compounds II-a in which X=SO$_2$. Alternatively, treatment of V with sulfonyl chlorides and a tertiary amine base (e.g. DiPEA or triethylamine) in a solvent such as dichloromethane can also give compounds II-a. Treatment of V with acyl chlorides in pyridine or Et$_3$N will yield compounds II-b, in which X=CO. In case the acid chlorides are not available, they can be easily prepared from the corresponding carboxylic acids using known methods (e.g. treatment with SOCl$_2$ or similar reagents). Compounds V are commercially available or prepared by methods know in the art, such as halogenation of compounds VI. Compounds VI are also commercially available or easily prepared by standard organic synthesis techniques.

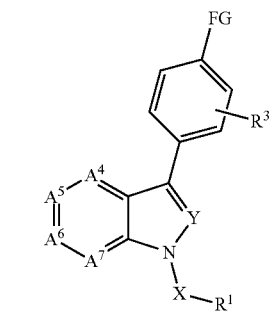

IV-a: X = SO$_2$
IV-b: X = CO
FG = Functional Group

Alternatively, a Suzuki reaction on compounds VII (obtained by Boc-protection of compounds V) will give compounds VIII (in most cases the Boc-group is cleaved under the reaction conditions, although a separate deprotection may be necessary). Now, acylation or sulfonylation as described for the conversion of V to II, yields compounds IV. The functional group (FG in formula IV) may be a tert-butyl ester, or a para-methoxy benzyl protected tetrazole, which after treatment with trifluoro acetic acid will give a carboxylate or 5-tetrazolyl, respectively, as required for compounds I. Finally, a Suzuki reaction on unprotected compounds V, may also directly lead to compounds VIII.

The invention is illustrated by the following examples.

General

The following procedure was used for Examples 1-23. $^1$H NMR spectra were recorded on a Bruker spectrometer (400

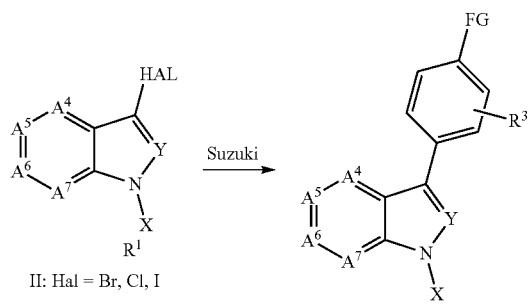

II: Hal = Br, Cl, I

IV

MHz) with deuterochloroform as the solvent unless stated otherwise. Chemical shifts are reported as δ values (parts per million) relative to tetramethylsilane as an internal standard.

MS: Electro Spray spectra were recorded on the Applied Biosystems API-165 single quad MS in alternating positive and negative ion mode using Flow Injection. The mass range was 120-2000 Da and scanned with a step rate of 0.2 Da. and the capillary voltage was set to 5000 V. N2-gas was used for nebulasation.

LC-MS spectrometer (Waters) Detector: PDA (200-320 nm), Mass detector: ZQ

Eluens: A: acetonitrile with 0.05% trifluoroacetic acid, B: acetonitrile/water=1/9 (v/v) with 0.05% trifluoroacetic acid Column 1: Chromolith Performance, RP-18e, 4.6×100 mm, Gradient method: Flow: 4 mL/min

| Time (min) | A (%) | B (%) |
|---|---|---|
| 0.0 | 100 | 0 |
| 3.60 | 0 | 100 |
| 4.00 | 0 | 100 |
| 4.05 | 100 | 0 |
| 6.00 | 100 | 0 |

Column 2: XBridge C18, 3.5 µm, 4.6×20 mm

Gradient method: Flow: 4 ml/min

| Time (min.) | A (%) | B (%) |
|---|---|---|
| 0.0 | 100 | 0 |
| 1.60 | 0 | 100 |
| 3.10 | 0 | 100 |
| 3.20 | 100 | 0 |
| 5.00 | 100 | 0 |

UPLC: Water acquity UPLC system; Column:BEH C18 1.7 µm, 2.1×100 mm, Detector: PDA (200-320 nm), Mass detector: SQD Eluens: A: acetonitrile with 0.035% trifluoroacetic acid, B: acetonitrile/water=1/9 (v/v) with 0.035% trifluoroacetic acid

| Time (min) | Method 60_100 Flow: 0.75 mL/min | | Method 40_80 Flow: 0.65 mL/min | | Method 0_60 Flow: 0.60 mL/min | |
|---|---|---|---|---|---|---|
| | A (%) | B (%) | A (%) | B (%) | A (%) | B (%) |
| 0.0 | 40 | 60 | 60 | 40 | 100 | 0 |
| 3.00 | 0 | 100 | 20 | 80 | 40 | 60 |
| 3.20 | 0 | 100 | 0 | 100 | 0 | 100 |
| 3.69 | 0 | 100 | 0 | 100 | 0 | 100 |
| 3.70 | 40 | 60 | 60 | 40 | 100 | 0 |

All target compounds were characterized and determined as at least >95% pure by $^1$H NMR, MS and analyticakl HPLC.

EXAMPLES

Example 1

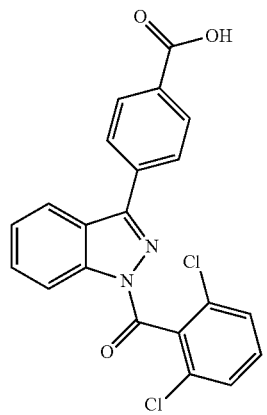 [SMILES: O=C(O)c1ccc(-c2nn(C(=O)c3c(Cl)cccc3Cl)c3ccccc23)cc1]

4-(1-(2,6-dichlorobenzoyl)-1H-indazol-3-yl)benzoic acid i) A solution of 3-bromo-4-azaindole (100 mg, 0.508 mmol) and 2,6-dichlorobenzoyl chloride (159 mg, 0.761 mmol) in 4 ml of pyridine was stirred for 1 h at 150° C. in a microwave reactor. After cooling to room temperature the reaction mixture was diluted with water and the product was extracted into $CH_2Cl_2$. The organic layer was washed with water, dried over a phase separation filter and concentrated under reduced pressure. The residue was purified on $SiO_2$, using 10% ethylacetate in heptane as the eluent, to give (3-bromo-1H-indazol-1-yl)(2,6-dichlorophenyl)methanone (140 mg) as a yellow solid.

ii) To a microwave reaction vial were added the product obtained in the previous step (53 mg, 0.143 mmol) in 2 ml dioxane, 4-(tert-butoxycarbonyl)phenylboronic acid (47.7 mg, 0.215 mmol) and a 2M aqueous solution of sodium carbonate (0.286 ml, 0.573 mmol). After purging the vial with nitrogen for about 5 minutes, $Pd(PPh_3)_4$ (8.28 mg, 7.16 µmmol) was added and the reaction mixture was stirred for 30 minutes at 100° C. in a microwave reactor. After cooling to room temperature, the reaction mixture was diluted with ethyl acetate and washed with water, brine and dried over magnesium sulfate.

After filtration the solvent was evaporated under reduced pressure and the desired product, tert-butyl 4-(1-(2,6-dichlorobenzoyl)-1H-indazol-3-yl)benzoate, was obtained as a yellow solid (90 mg). The product was used in the next step without further purification.

iii) A solution of the product obtained in the previous step (90 mg, 0.22 mmol) and trifluoroacetic acid (5 ml, 67.3 mmol) in 20 ml $CH_2Cl_2$ was stirred for 1 h at room temperature After completion, the reaction mixture was concentrated under reduced pressure and the residue was purified on $SiO_2$, using 10% ethylacetate in heptane as the eluent to give the title compound 4-(1-(2,6-dichlorobenzoyl)-1H-indazol-3-yl) benzoic acid as a white solid (50 mg). ESI MS=m/z 411 [M+H]$^+$ Example 2

Following a procedure analogous to that described in Example 1, starting from 3-bromo-5-fluoro-1H-indazole, the following compound was prepared.

4-(1-(2,6-dichlorobenzoyl)-5-fluoro-1H-indazol-3-yl)benzoic acid

ESI MS=m/z 429 [M+H]+

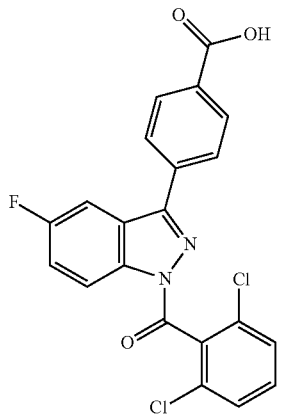 [SMILES: O=C(O)c1ccc(-c2nn(C(=O)c3c(Cl)cccc3Cl)c3ccc(F)cc23)cc1]

Example 3

Following a procedure analogous to that described in Example 1, starting from 3-bromo-7-fluoro-1H-indazole, the following compound was prepared.

4-(1-(2,6-dichlorobenzoyl)-7-fluoro-1H-indazol-3-yl)benzoic acid

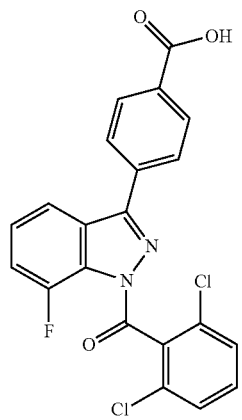 [SMILES: O=C(O)c1ccc(-c2nn(C(=O)c3c(Cl)cccc3Cl)c3c(F)cccc23)cc1]

ESI MS=m/z 429 [M+H]+

Example 4

Following a procedure analogous to that described in Example 1, starting from 3-bromo-4-fluoro-1H-indazole, the following compound was prepared.

4-(1-(2,6-dichlorobenzoyl)-4-fluoro-1H-indazol-3-yl)benzoic acid

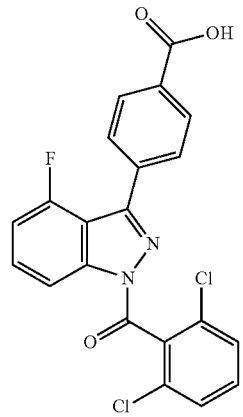 [SMILES: O=C(O)c1ccc(-c2nn(C(=O)c3c(Cl)cccc3Cl)c3cccc(F)c23)cc1]

ESI MS=m/z 429 [M+H]+

Example 5

Following a procedure analogous to that described in Example 1, starting from 3-bromo-6-fluoro-1H-indazole, the following compound was prepared.

4-(1-(2,6-dichlorobenzoyl)-6-fluoro-1H-indazol-3-yl)benzoic acid

ESI MS=m/z 429 [M+H]+

Example 6

Following a procedure analogous to that described in Example 1, starting from 3-bromo-M-pyrazolo[4,3-b]pyridine, the following compounds were prepared.

6A: 4-(1-(2,6-dichlorobenzoyl)-1H-pyrazolo[4,3-b]pyridin-3-yl)benzoic acid

ESI MS=m/z 412 [M+H]+

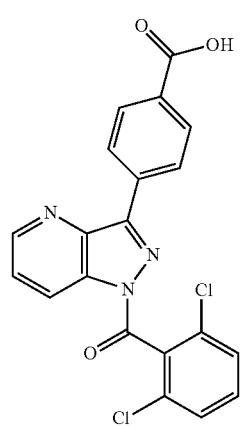 [SMILES: O=C(O)c1ccc(-c2nn(C(=O)c3c(Cl)cccc3Cl)c3cccnc23)cc1]

6B: 4-(1-(2-(trifluoromethyl)benzoyl)-1H-pyrazolo[4,3-b]pyridin-3-yl)benzoic acid ESI MS=m/z 412 [M+H]+

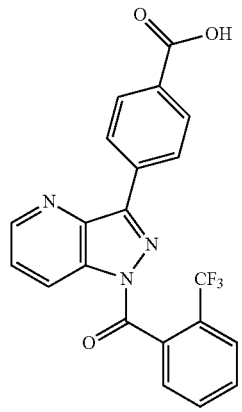 [SMILES: O=C(O)c1ccc(-c2nn(C(=O)c3ccccc3C(F)(F)F)c3cccnc23)cc1]

Example 7

Following a procedure analogous to that described in Example 1, starting from 3-bromo-1H-pyrrolo[3,2-b]pyridine, the following compound was prepared.

4-(1-(2,6-dichlorobenzoyl)-1H-pyrrolo[3,2-b]pyridin-3-yl)benzoic acid

ESI MS=m/z 412 [M+H]+

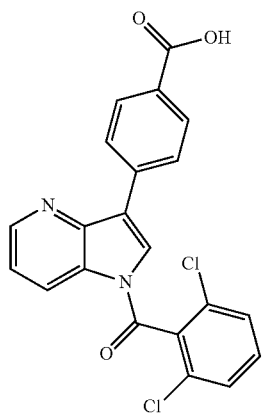 [SMILES: O=C(O)c1ccc(-c2cn(C(=O)c3c(Cl)cccc3Cl)c3cccnc23)cc1]

Example 8

Following a procedure analogous to that described in Example 1, starting from 3-bromo-1H-pyrazolo[4,3-c]pyridine, the following compound was prepared.

4-(1-(2,6-dichlorobenzoyl)-1H-pyrazolo[4,3-c]pyridin-3-yl)benzoic acid

ESI MS=m/z 412 [M+H]+

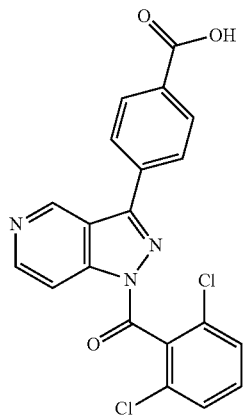 [SMILES: O=C(O)c1ccc(-c2nn(C(=O)c3c(Cl)cccc3Cl)c3ccncc23)cc1]

Example 9

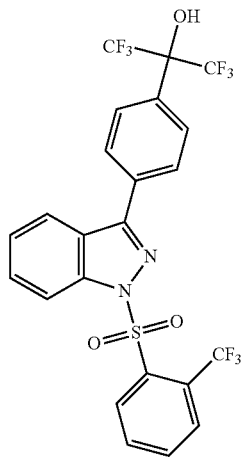 [SMILES: O=S(=O)(c1ccccc1C(F)(F)F)n1nc(-c2ccc(C(O)(C(F)(F)F)C(F)(F)F)cc2)c2ccccc21]

1,1,1,3,3,3-hexafluoro-2-(4-(1-(2-(trifluoromethyl)phenylsulfonyl)-1H-indazol-3-yl)phenyl)propan-2-ol i) To a suspension of 3-bromoindazole (500 mg, 2.54 mmol) in 8 ml CH$_2$Cl$_2$ was added triethyl amine (1.06 ml, 7.61 mmol) at room temperature. To this yellow solution was added 2-(trifluoromethyl)benzenesulfonyl chloride (0.392 ml, 2.54 mmol) and the reaction mixture was stirred for 3 h at room temperature. The reaction mixture was concentrated under reduced pressure and the residue was purified on SiO$_2$ using 5% to 20% ethyl acetate in heptane to give 3-bromo-1-(2-(trifluoromethyl)phenylsulfonyl)-1H-indazole (894 mg)

ii) Following a procedure analogous to that described in Example 1, step ii, using 1,1,1,3,3,3-hexafluoro-2-(4-(4,4,5,5-tetramethyl-1,3,2-dioxaborolan-2-yl)phenyl)propan-2-ol as the boronic ester, the title compound 1,1,1,3,3,3-hexafluoro-2-(4-(1-(2-(trifluoromethyl)phenylsulfonyl)-1H-indazol-3-yl)phenyl)propan-2-ol was prepared (9 mg).

ESI MS=m/z 569 [M+H]+

Example 10

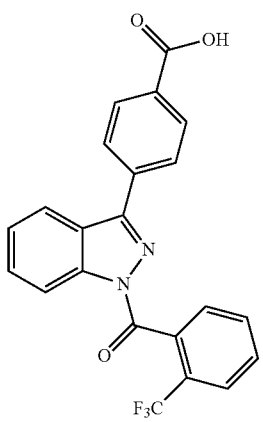 [SMILES: O=C(O)c1ccc(-c2nn(C(=O)c3ccccc3C(F)(F)F)c3ccccc23)cc1]

4-(1-(2-(trifluoromethyl)benzoyl)-1H-indazol-3-yl)benzoic acid i) To a mixture of tert-butyl 3-bromo-1H-indazole-1-carboxylate (5 g, 16.83 mmol,) and 4-(tert-butoxycarbonyl)phenylboronic acid (4.52 g, 20.36 mmol) in 30 ml of dioxane and 30 ml water was added sodium carbonate (50.5 mmol, 5.35 g). The mixture was purged with $N_2$ and subsequently, $Pd(PPh_3)_4$ (0.486 g, 0.421 mmol) was added. The reaction mixture was heated to 100° C. overnight under a nitrogen atmosphere.

After cooling to room temperature, the reaction mixture was diluted with water and the product was extracted into ethyl acetate. The combined organic layers were washed with water, brine and dried over magnesium sulfate. After filtration, the solvent was removed under reduced pressure and the residue was purified on $SiO_2$, using 0% to 25% ethylacetate in heptane as the eluent, to give tert-butyl 4-(1H-indazol-3-yl)benzoate as a yellow solid.

ii) To a solution of tert-butyl 4-(1H-indazol-3-yl)benzoate (40 mg, 0.136 mmol) in 1 ml of pyridine was added 2-(trifluoromethyl)benzoyl chloride (356 mg, 1.699 mmol).

The reaction mixture was stirred at 150° C. in a microwave reactor for 1 h

After cooling, water was added and the product was extracted into ethylacetate. The organic layer was washed with water, brine and dried over magnesium sulfate. After filtration, the solvent was removed under reduced pressure and the residue was purified on $SiO_2$, using 3% to 20% ethylacetate in heptane as the eluent, to give tert-butyl 4-(1-(2-(trifluoromethyl)benzoyl)-1H-indazol-3-yl)benzoate as a white solid.

iii) A solution of the compound obtained in the previous step (19.4 mg, 0.042 mmol) and trifluoroacetic acid (0.5 ml, 6.73 mmol,) in 2 ml $CH_2Cl_2$ was stirred for 1 h at room temperature.

After the reaction was complete the reaction mixture was concentrated under reduced pressure to give the title compound 4-(1-(2-(trifluoromethyl)benzoyl)-1H-indazol-3-yl)benzoic acid as a light yellow solid.

ESI MS=m/z 411 [M+H]$^+$

Example 11

Following a procedure analogous to that described in Example 10, the following compounds were prepared.

11A: 4-(1-(3,5-dichloroisonicotinoyl)-1H-indazol-3-yl)benzoic acid

ESI MS=m/z 412 [M+H]$^+$

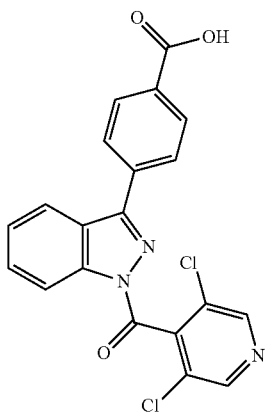 [SMILES: O=C(O)c1ccc(-c2nn(C(=O)c3c(Cl)cncc3Cl)c3ccccc23)cc1]

11B: 4-(1-(2-bromobenzoyl)-1H-indazol-3-yl)benzoic acid

ESI MS=m/z 421/423 [M+H]$^+$

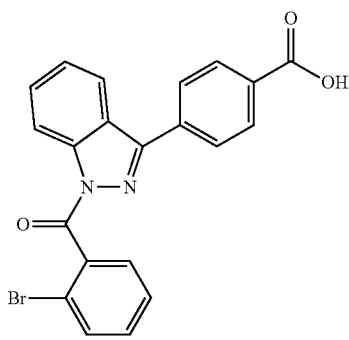 [SMILES: O=C(O)c1ccc(-c2nn(C(=O)c3ccccc3Br)c3ccccc23)cc1]

11C: 4-(1-(2-(methoxycarbonyl)benzoyl)-1H-indazol-3-yl)benzoic acid

ESI MS=m/z 401 [M+H]$^+$

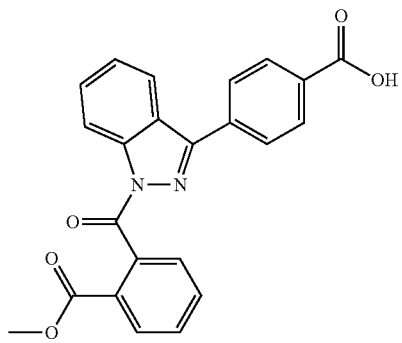 [SMILES: COC(=O)c1ccccc1C(=O)n1nc(-c2ccc(C(=O)O)cc2)c2ccccc21]

11D:
4-(1-(cyclohexanecarbonyl)-1H-indazol-3-yl)benzoic acid

ESI MS=m/z 349 [M+H]+

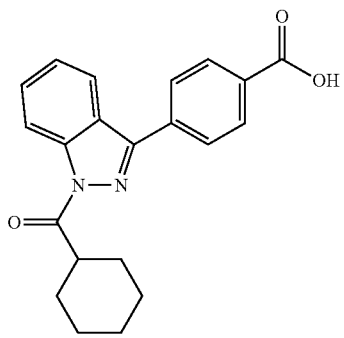 [SMILES: O=C(O)c1ccc(-c2nn(C(=O)C3CCCCC3)c3ccccc23)cc1]

11E: 4-(1-(2-bromo-6-chlorobenzoyl)-1H-indazol-3-yl)benzoic acid

ESI MS=m/z 457 [M+H]+

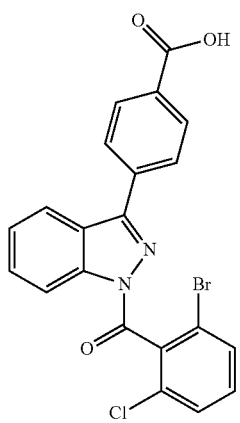 [SMILES: O=C(O)c1ccc(-c2nn(C(=O)c3c(Cl)cccc3Br)c3ccccc23)cc1]

11F: 4-(1-(2-fluoro-6-(trifluoromethyl)benzoyl)-1H-indazol-3-yl)benzoic acid

ESI MS=m/z 429 [M+H]+

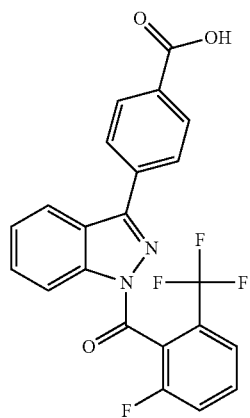 [SMILES: O=C(O)c1ccc(-c2nn(C(=O)c3c(F)cccc3C(F)(F)F)c3ccccc23)cc1]

11G: 4-(1-(2-fluoro-6-methoxybenzoyl)-1H-indazol-3-yl)benzoic acid

ESI MS=m/z 391 [M+H]+

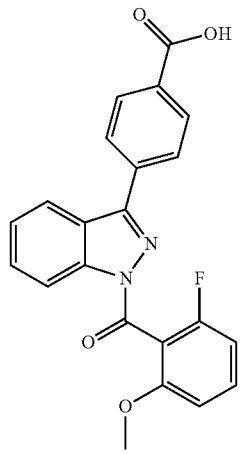 [SMILES: COc1cccc(F)c1C(=O)n1nc(-c2ccc(C(=O)O)cc2)c2ccccc21]

11H: 4-(1-(2,4,6-trichlorobenzoyl)-1H-indazol-3-yl)benzoic acid

ESI MS=m/z 445/447 [M+H]+

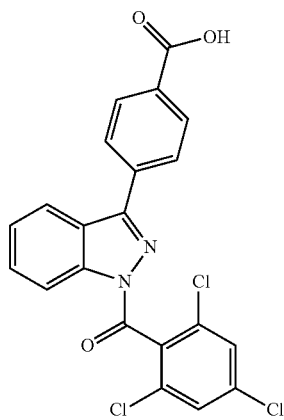 [SMILES: O=C(O)c1ccc(-c2nn(C(=O)c3c(Cl)cc(Cl)cc3Cl)c3ccccc23)cc1]

11I: 4-(1-(2,6-dimethylbenzoyl)-1H-indazol-3-yl)benzoic acid

ESI MS=m/z 371 [M+H]+

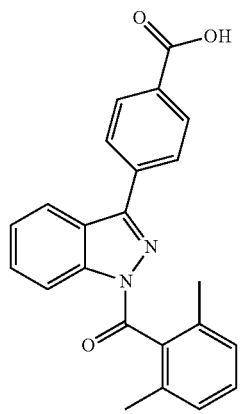 [SMILES: Cc1cccc(C)c1C(=O)n1nc(-c2ccc(C(=O)O)cc2)c2ccccc21]

11J: 4-(1-(2-ethoxybenzoyl)-1H-indazol-3-yl)benzoic acid
ESI MS=m/z 387 [M+H]$^+$
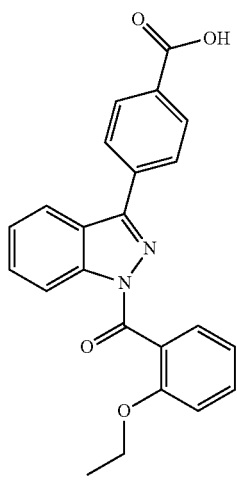 [SMILES: CCOc1ccccc1C(=O)n1nc(-c2ccc(C(=O)O)cc2)c2ccccc21]
11K: 4-(1-(2,3-dichlorobenzoyl)-1H-indazol-3-yl)benzoic acid
ESI MS=m/z 411 [M+H]$^+$
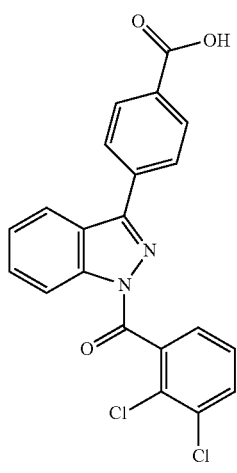 [SMILES: O=C(O)c1ccc(-c2nn(C(=O)c3cccc(Cl)c3Cl)c3ccccc23)cc1]
11L: 4-(1-(2-chlorobenzoyl)-1H-indazol-3-yl)benzoic acid
ESI MS=m/z 377 [M+H]$^+$
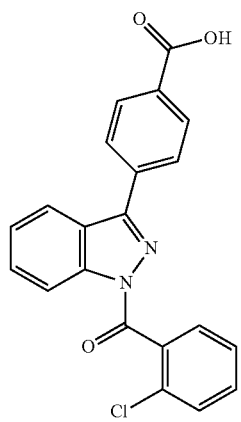 [SMILES: O=C(O)c1ccc(-c2nn(C(=O)c3ccccc3Cl)c3ccccc23)cc1]
11M: 4-(1-(2-chloro-6-(trifluoromethyl)benzoyl)-1H-indazol-3-yl)benzoic acid
ESI MS=m/z 445 [M+H]$^+$
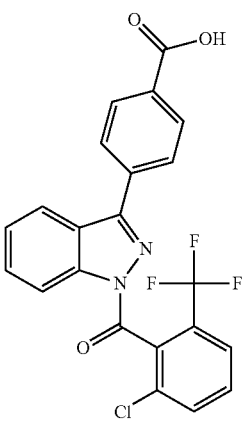 [SMILES: O=C(O)c1ccc(-c2nn(C(=O)c3c(Cl)cccc3C(F)(F)F)c3ccccc23)cc1]

11N: 4-(1-(2-methyl-6-nitrobenzoyl)-1H-indazol-3-yl)benzoic acid

ESI MS=m/z 402 [M+H]$^+$

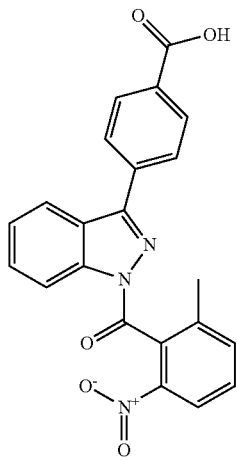 [SMILES: Cc1cccc([N+](=O)[O-])c1C(=O)n1nc(-c2ccc(C(=O)O)cc2)c2ccccc21]

Example 12

4-(1-(2-(trifluoromethyl)phenylsulfonyl)-1H-indazol-3-yl)benzoic acid

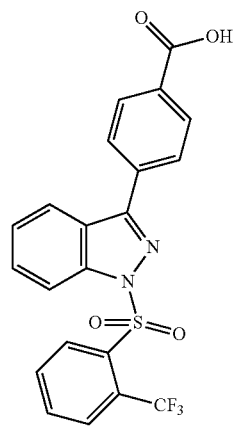 [SMILES: O=C(O)c1ccc(-c2nn(S(=O)(=O)c3ccccc3C(F)(F)F)c3ccccc23)cc1]

i) To a solution of tert-butyl 4-(1'-indazol-3-yl)benzoate, Example 10, step i, (58 mg, 0.197 mmol) in 2 ml CH$_2$Cl$_2$ were added triethyl amine (60 mg, 0.592 mmol) and 2-(trifluoromethyl)benzenesulfonyl chloride (48 mg, 0.197 mmol). The reaction mixture was stirred overnight at room temperature. The reaction mixture was directly purified on SiO$_2$ using 0% to 50% ethyl acetate in heptane as the eluent to give tert-butyl 4-(1-(2-(trifluoromethyl)phenylsulfonyl)-1H-indazol-3-yl)benzoate)102 mg) as a clear oil.

ii) Following a procedure analogous to that described in Example 10, step iii, the title compound, 4-(1-(2-(trifluoromethyl)phenylsulfonyl)-1H-indazol-3-yl)benzoic acid, was prepared (28 mg)

ESI MS=m/z 447 [M+H]$^+$

Example 13

Following a procedure analogous to that described in Example 11, the following compounds were prepared.

13A: 4-(1-(quinolin-8-ylsulfonyl)-1H-indazol-3-yl)benzoic acid

ESI MS=m/z 429 [M+H]$^+$

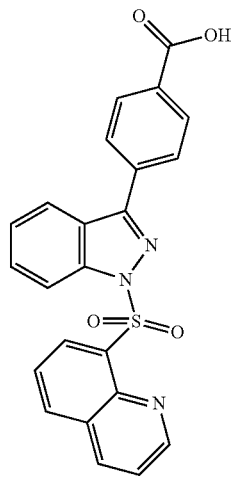 [SMILES: O=C(O)c1ccc(-c2nn(S(=O)(=O)c3cccc4cccnc34)c3ccccc23)cc1]

13B: 4-(1-(2-bromophenylsulfonyl)-1H-indazol-3-yl)benzoic acid

ESI MS=m/z 457/459 [M+H]$^+$

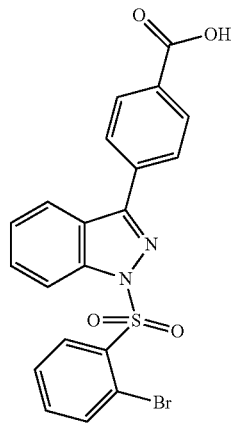 [SMILES: O=C(O)c1ccc(-c2nn(S(=O)(=O)c3ccccc3Br)c3ccccc23)cc1]

13C: 4-(1-(2,5-dichlorophenylsulfonyl)-1H-indazol-3-yl)benzoic acid
ESI MS=m/z 447 [M+H]+
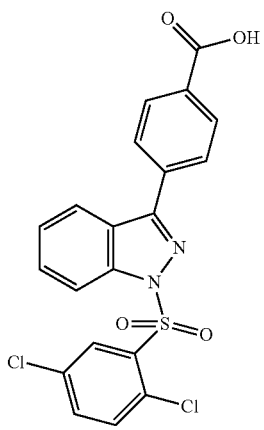 [SMILES: O=C(O)c1ccc(-c2nn(S(=O)(=O)c3cc(Cl)ccc3Cl)c3ccccc23)cc1]
13D: 4-(1-(3-chloro-2-methylphenylsulfonyl)-1H-indazol-3-yl)benzoic acid
ESI MS=m/z 427 [M+H]+
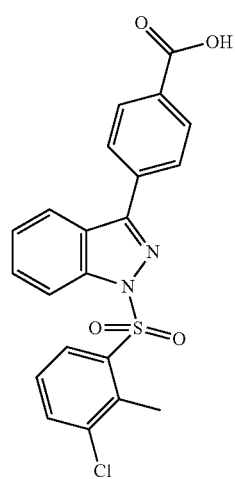 [SMILES: Cc1c(Cl)cccc1S(=O)(=O)n1nc(-c2ccc(C(=O)O)cc2)c2ccccc21]
13E: 4-(1-(2,3-dichlorophenylsulfonyl)-1H-indazol-3-yl)benzoic acid
ESI MS=m/z 447 [M+H]+
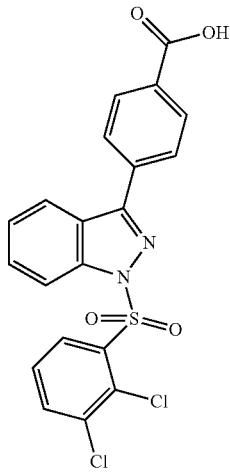 [SMILES: O=C(O)c1ccc(-c2nn(S(=O)(=O)c3cccc(Cl)c3Cl)c3ccccc23)cc1]
13F: 4-(1-(2,3,4-trichlorophenylsulfonyl)-1H-indazol-3-yl)benzoic acid
ESI MS=m/z 481/483 [M+H]+
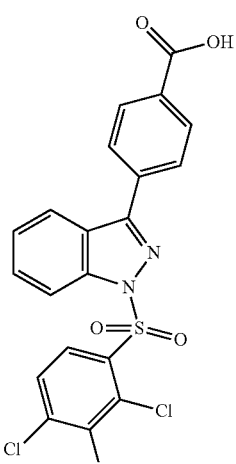

Example 14

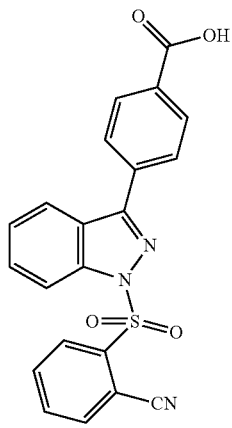 [SMILES: N#Cc1ccccc1S(=O)(=O)n1nc(-c2ccc(C(=O)O)cc2)c2ccccc21]

4-(1-(2-cyanophenylsulfonyl)-1H-indazol-3-yl)benzoic acid i) To a solution of 3-bromo-1H-indazole (200 mg, 1.02 mmol) in 2 ml $CH_2Cl_2$ was added triethylamine (308 mg, 3.05 mmol) and 2-cyanobenzene-1-sulfonyl chloride (205 mg, 1.02 mmol). The reaction mixture was stirred overnight at room temperature. After completion the reaction mixture was concentrated under reduced pressure and the product was purified on $SiO_2$ using 0% to 50% ethyl acetate in heptane as the eluent to give 3-bromo-1-(2-cyanophenylsulfonyl)-1H-indazole (360 mg) as a yellow solid.

ii) To a microwave reaction vial were added the product obtained in the previous step (50 mg, 0.138 mmol) in 2 ml toluene and 0.5 ml ethanol, 4-(tert-butoxycarbonyl)phenylboronic acid (50 mg, 0.166 mmol) and a 2M aqueous solution of potassium carbonate (0.345 ml, 0.690 mmol). After purging the vial with nitrogen for about 5 minutes, $Pd(PPh_3)_4$ (3.99 mg) was added and the reaction mixture was stirred for 30 minutes at 100° C. in a microwave reactor. After cooling to room temperature, the reaction mixture was diluted with water and product was extracted into ethyl acetate. The organic layer was washed with water, brine and dried over magnesium sulfate.

After filtration the solvent was evaporated under reduced pressure and the product was purified on $SiO_2$ using 0% to 50% ethylacetate in heptane as the eluent to give the desired product, tert-butyl 4-(1-(2-cyanophenylsulfonyl)-1H-indazol-3-yl)benzoate (12 mg).

iii) Following a procedure analogous to that described in Example 10, step iii, the title compound, 4-(1-(2-cyanophenylsulfonyl)-1H-indazol-3-yl)benzoic acid, was prepared (13 mg)

ESI MS=m/z 404 [M+H]$^+$

Example 15

Following a procedure analogous to that described in Example 14, the following compounds were prepared.

15A: 4-(1-(2-(trifluoromethoxy)phenylsulfonyl)-1H-indazol-3-yl)benzoic acid

ESI MS=m/z 463 [M+H]$^+$

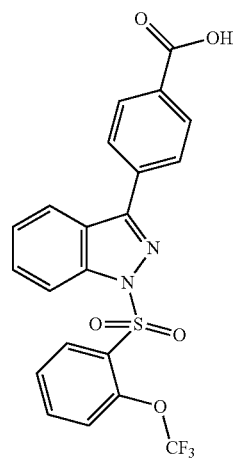 [SMILES: O=C(O)c1ccc(-c2nn(S(=O)(=O)c3ccccc3OC(F)(F)F)c3ccccc23)cc1]

15B: 4-(1-(naphthalen-1-ylsulfonyl)-1H-indazol-3-yl)benzoic acid

ESI MS=m/z 429 [M+H]$^+$

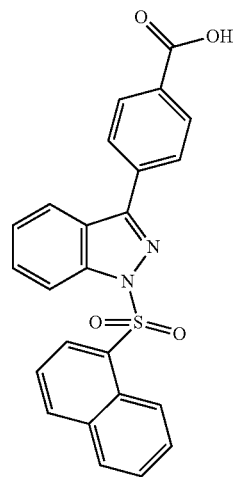 [SMILES: O=C(O)c1ccc(-c2nn(S(=O)(=O)c3cccc4ccccc34)c3ccccc23)cc1]

15C: 4-(1-(2,6-dichlorophenylsulfonyl)-1H-indazol-3-yl)benzoic acid

ESI MS=m/z 447 [M+H]⁺

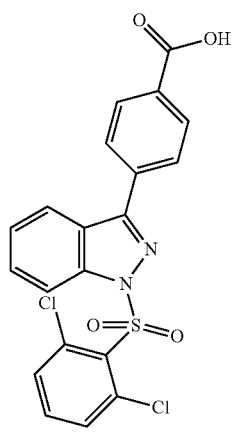 [SMILES: O=C(O)c1ccc(-c2nn(S(=O)(=O)c3c(Cl)cccc3Cl)c3ccccc23)cc1]

15D: 4-(1-(benzo[c][1,2,5]oxadiazol-4-ylsulfonyl)-1H-indazol-3-yl)benzoic acid

ESI MS=m/z 421 [M+H]⁺

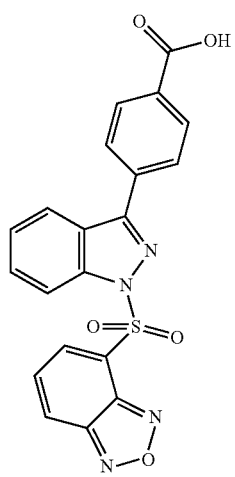 [SMILES: O=C(O)c1ccc(-c2nn(S(=O)(=O)c3cccc4nonc34)c3ccccc23)cc1]

15E: 4-(1-(2-cyano-5-methylphenylsulfonyl)-1H-indazol-3-yl)benzoic acid

ESI MS=m/z 418 [M+H]⁺

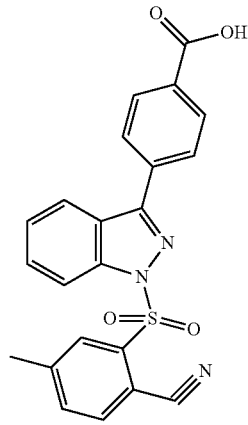 [SMILES: Cc1ccc(C#N)c(S(=O)(=O)n2nc(-c3ccc(C(=O)O)cc3)c3ccccc32)c1]

Example 16

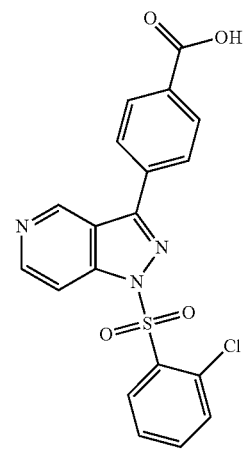 [SMILES: O=C(O)c1ccc(-c2nn(S(=O)(=O)c3ccccc3Cl)c3ccncc23)cc1]

4-(1-(2-chlorophenylsulfonyl)-1H-pyrazolo[4,3-c]pyridin-3-yl)benzoic acid i) To a solution of 3-bromo-1H-pyrazolo[4,3-c]pyridine (198 mg, 1,0 mmol) in 10 ml THF was added portion wise at 0° C. sodium hydride (101 mg, 4 mmol, 95%). After addition was complete, 2-chlorobenzenesulfonyl chloride (495 mg, 2.347 mmol) was added and the reaction mixture was stirred overnight at room temperature. The reaction mixture was quenched by the addition of water. The product was extracted into ethyl acetate and the organic layer was washed with brine. The organic solvent was evaporated under reduced pressure to give 3-bromo-1-(2-chlorophenylsulfonyl)-1H-pyrazolo[4,3-c]pyridine as a yellow oil. The product was used in the next step without further purification.

ii) To a microwave reaction vial were added the product obtained in the previous step (67 mg, 0.135 mmol) in 3 ml DME, tert-butyl 4-(4,4,5,5-tetramethyl-1,3,2-dioxaborolan-2-yl)benzoate (49.2 mg, 0.162 mmol) and 0.472 ml of a 2M aqueous solution of sodium carbonate (0.944 mmol). After purging the vial with nitrogen for about 5 minutes, Pd(PPh₃)₄ (31.2 mg, 0.027 mmol) was added and the reaction mixture was stirred for 40 minutes at 100° C. in a microwave reactor. After cooling to room temperature, the reaction mixture was diluted with water and washed with ethyl acetate. The organic layer was washed with water, brine and dried over magnesium sulfate.

After filtration the solvent was evaporated under reduced pressure and the product was purified preparative HPLC using 20% to 100% CH₃CN in water as the eluent to give tert-butyl 4-(1-(2-chlorophenylsulfonyl)-1H-pyrazolo[4,3-c]pyridin-3-yl)benzoate as a yellow solid (16 mg).

iii) Following a procedure analogous to that described in Example 10, step iii, the title compound, 4-(1-(2-chlorophenylsulfonyl)-1H-pyrazolo[4,3-c]pyridin-3-yl)benzoic acid, was prepared (7 mg)

ESI MS=m/z not measured [M+H]⁺

Example 17

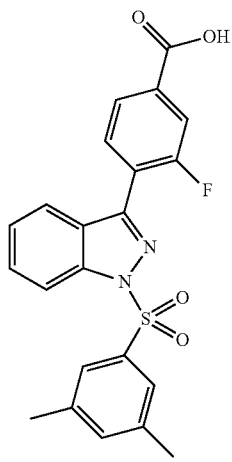 [SMILES: Cc1cc(C)cc(S(=O)(=O)n2nc(-c3ccc(C(=O)O)cc3F)c3ccccc32)c1]

4-(1-(3,5-dimethylphenylsulfonyl)-1H-indazol-3-yl)-3-fluorobenzoic acid i) 3-bromo-1H-indazole (3 gram; 15 mmol) was dissolved in 30 ml DMF, followed by the addition of sodiumhydride (850 mg, 21 mmol). After stirring for 20 min at room temperature, 3,5-dimethylbenzene-1-sulfonyl chloride (4.4 gram, 21 mmol) was added and the reaction mixture was stirred for another 2 h at room temperature. The reaction was quenched by the addition of water and the formed solids were filtered off and washed with little methanol. The solids were dried to obtain 3-bromo-1-(3,5-dimethylphenylsulfonyl)-1H-indazole (2.1 gram) as a white solid.

ii) The product obtained in the previous step (100 mg, 0.27 mmol), Pd(PPh₃)₄ (63 mg, 0.05 mmol) and 4-borono-3-fluorobenzoic acid (101 mg, 0.55 mmol) were stirred in 6.5 ml DME and 3.5 ml of an aqueous solution of NaHCO₃ (69 mg, 0.82 mmol) was added. The reaction mixture was heated in a microwave reactor for 30 min at 100° C. After cooling, the reaction mixture was filtered over cotton and the volatiles were evaporated under reduced pressure. The crude material was purified by prep. HPLC (Gemini NX column (100*30 mm, 5 μm); 40 ml/min; Eluens A: 20 mmol/L NH₄HCO₃ (aq) and Eluens B: acetonitrile; Gradient: 0-7 min 70% A and 30% B; 7-7.1 min 50% A and 50% B; 7.1-8.5 min 100% B) to give the title compound 4-(1-(3,5-dimethylphenylsulfonyl)-1H-indazol-3-yl)-3-fluorobenzoic acid (25 mg) as an off white solid.

ESI MS m/z 425 [M+H]⁺

Example 18

Following a procedure analogous to that described in Example 17, the following compounds was prepared.

4-(1-(3,5-dimethylphenylsulfonyl)-1H-indazol-3-yl)-2-(trifluoromethyl)benzoic acid ESI MS m/z 475 [M+H]⁺

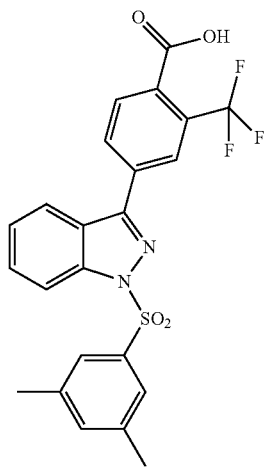 [SMILES: Cc1cc(C)cc(S(=O)(=O)n2nc(-c3ccc(C(=O)O)c(C(F)(F)F)c3)c3ccccc32)c1]

Example 19

5-(4-(4,4,5,5-Tetramethyl-1,3,2-dioxaborolan-2-yl)phenyl)-1H-tetrazole

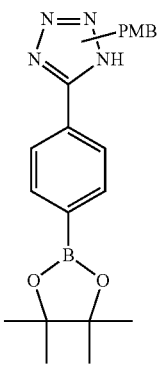

i) 4-(4,4,5,5-Tetramethyl-1,3,2-dioxaborolan-2-yl)benzonitrile (8.0 g, 34.8 mmol), trimethylsilyl azide, (8.04 g, 69.8 mmol) and dibutyl-stannanone (868 mg, 3.5 mmol, 0.1 equiv) were dissolved in 1,2-dimethoxy ethane (110 ml). The mixture was divided in two portions and transferred in two microwave vessels then irradiated in a microwave reactor simultaneously at 150° C. for 10 min. After cooling to room temperature, trimethylsilyl azide (4.02 g, 35 mmol) and dibutyl-stannanone (434 mg, 1.75 mmol) were added into each microwave vessel and the mixtures were irradiated again at 150° C. for 10 min. After cooling to room temperature, the mixtures were combined and purified by column chromatography on florisil (200 g). It was first eluted with 20% dichloromethane in hexane to remove the impurities, then with 10% methanol in dichloromethane to elute the product. 1-(4-Methoxybenzyl)-5-(4-(4,4,5,5-tetramethyl-1,3,2-dioxaborolan-2-yl)phenyl)-1H-tetrazole 2 was isolated as a white powder (8.01 g).

APCI MS m/z 273 [M+H]$^+$.

ii) The product obtained in the previous step (8.40 g, 30.9 mmol) was dissolved in acetonitrile (150 ml). First potassium carbonate powder (5.12 g, 37.0 mmol, 1.2 equiv), then 4-methoxybenzyl chloride (6.3 mL, 46.3 mmol) were added. After stirring at 40° C. for 12 hours the reaction mixture was diluted with ethyl-acetate (100 ml), washed with water (2×100 ml) and dried over magnesium sulfate. After filtration the solvent was evaporated under reduced pressure. The residue was suspended in hexane and the formed crystals were filtered. Title compound 1-(4-Methoxybenzyl)-5-(4-(4,4,5,5-tetramethyl-1,3,2-dioxaborolan-2-yl)phenyl)-1H-tetrazole was obtained as a white powder as a mixture of regio-isomers (9.67 g).

APCI MS m/z 393 [M+H]$^+$.

Example 20

3-(4-(1H-tetrazol-5-yl)phenyl)-1-(3-chlorophenylsulfonyl)-1H-indazole

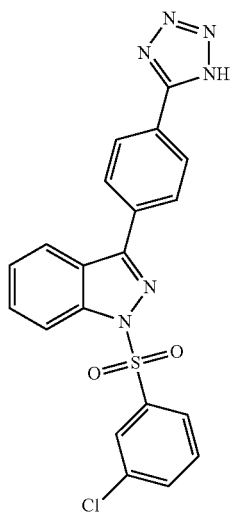 [SMILES: O=S(=O)(c1cccc(Cl)c1)n1nc(-c2ccc(-c3nnn[nH]3)cc2)c2ccccc21]

i) Tert-butyl 3-bromo-1H-indazole-1-carboxylate (5.0 g, 16.8 mmol) and a mixture of the regio-isomers of 1-(4-methoxybenzyl)-5-(4-(4,4,5,5-tetramethyl-1,3,2-dioxaborolan-2-yl)phenyl)-1H-tetrazole (Example 19, step ii) (7.92 g, 20.2 mmol) were dissolved in 100 ml of a 1 to 1 mixture of 1,4-dioxane and water under a nitrogen atmosphere. Sodium carbonate (5.35 g, 50.5 mmol) was added and the system was purged with nitrogen. Then Pd(PPh$_3$)$_4$ (486 mg, 0.42 mmol) was added and the reaction mixture was heated overnight at reflux temperature under a nitrogen atmosphere. After cooling to room temperature the mixture was diluted with water and extracted with ethyl acetate. The combined organic phases were washed with brine, dried over magnesium sulfate. After filtration the solvent was removed under reduced pressure. The residue was purified on SiO$_2$ using 20 to 30% ethyl acetate in hexane as the eluent to give 3-(4-(1-(4-methoxybenzyl)-1H-tetrazol-5-yl)phenyl)-1H-indazole as a mixture of two regioisomers in a 2 to 1 ratio (2.8 g) as a white solid.

Major regio-isomer (1.91 g, 30%) as a white powder.

APCI MS m/z 383 [M+H]$^+$, ii) To a solution of the product obtained in the previous step (100 mg, 0.26 mmol) in 2 ml anhydrous THF was added t-BuOK (32 mg, 0.29 mmol). After stirring the reaction mixture at room temperature for 20 min, 3-Chlorobenzene-1-sulfonyl chloride (41 mg, 0.29 mmol) was added and the mixture was stirred at room temperature for an additional 2 h. After completion, the solvent was evaporated under reduced pressure, the residue was dissolved in dichloromethane and washed with water. The organic phase was evaporated and the residue was dried under reduced pressure to afford 1-(3-chlorophenylsulfonyl)-3-(4-(1-(4-methoxybenzyl)-1H-tetrazol-5-yl)phenyl)-1H-indazole (146 mg, crude) as a brown oil which was used in the next step without any further purification.

ESI MS m/z 557 [M+H]+ iii) The product obtained in the previous step (81 mg) was dissolved in 1 ml trifluoroacetic acid and stirred for 2 days at room temperature. The solvent was evaporated under reduced pressure and the residue was purified by preparative HPLC using eluent system 1 then eluent system 2 to afford 3-(4-(1H-tetrazol-5-yl)phenyl)-1-(3-chlorophenylsulfonyl)-1H-indazole (26 mg) as a white powder:

ESI MS m/z 437 [M+H]$^+$

Example 21

Following a procedure analogous to that described in Example 20, the following compounds were prepared.

21A: methyl 3-(3-(4-(1H-tetrazol-5-yl)phenyl)-1H-indazol-1-ylsulfonyl)thiophene-2-carboxylate ESI MS=m/z 467 [M+H]$^+$

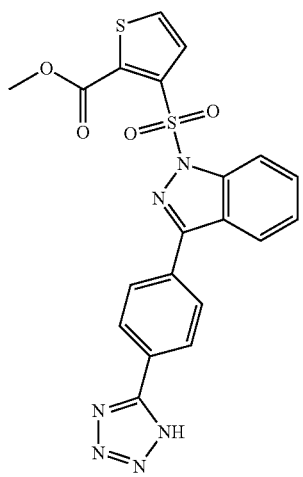 [SMILES: COC(=O)c1sccc1S(=O)(=O)n1nc(-c2ccc(-c3nnn[nH]3)cc2)c2ccccc21]

21B: 3-(1H-tetrazol-5-yl)phenyl)-1-(2-bromo-4-fluorophenylsulfonyl)-1H-indazole

21D: 4-(3-(1H-tetrazol-5-yl)phenyl)-1H-indazol-1-ylsulfonyl)-3,5-dimethylisoxazole

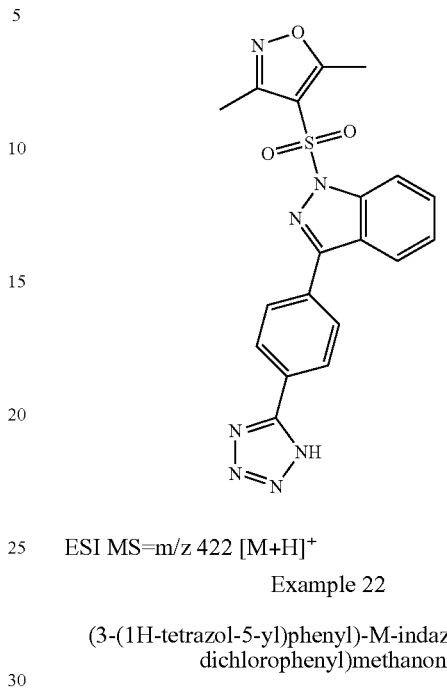

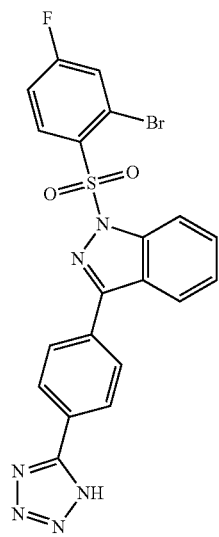 [SMILES: O=S(=O)(c1ccc(F)cc1Br)n1nc(-c2ccc(-c3nnn[nH]3)cc2)c2ccccc21]

ESI MS=m/z 422 [M+H]+

Example 22

(3-(1H-tetrazol-5-yl)phenyl)-M-indazol-1-yl)(2,6-dichlorophenyl)methanone

ESI MS=m/z 499/501[M+H]+

21C: 3-(1H-tetrazol-5-yl)phenyl)-1-(3-bromo-5-chlorothiophen-2-ylsulfonyl)-1H-indazole

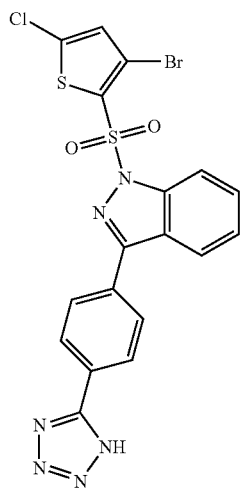 [SMILES: O=S(=O)(c1sc(Cl)cc1Br)n1nc(-c2ccc(-c3nnn[nH]3)cc2)c2ccccc21]

i) To a solution of a mixture of regio-isomers of 3-(4-(1-(4-Methoxybenzyl)-1H-tetrazol-5-yl)phenyl)-1H-indazole (Example 20, step i) (50 mg, 0.13 mmol) was dissolved in anhydrous THF (1 ml). After addition of t-BuOK (16 mg, 0.14 mmol,) the reaction mixture was stirred at room temperature for 15 min. Subsequently, 2,6-dichlorobenzoyl chloride (21 μl, 0.14 mmol) was added and the reaction mixture was stirred for another 2 h at room temperature. The solvent was evaporated under reduced pressure, the residue was dissolved in dichloromethane and washed with water, an aqueous solution of 5% $K_2CO_3$ and water. The organic solvent was evaporated under reduced pressure and the residue was dried in vacuo. The product was purified by preparative HPLC to afford (2,6-dichlorophenyl)(3-(4-(1-(4-methoxybenzyl)-1H-tetrazol-5-yl)phenyl)-1H-indazol-1-yl)methanone as a mixture of 2 regioisomers in a 98 to 2 ratio (59 mg, 74%).
ESI MS m/z 555 [M+H]+.

ESI MS=m/z 523 [M+H]+ ii) Following a procedure analogous to that described in Example 20, step iii, the product obtained in the previous step was converted to the title compound (3-(4(1H-tetrazol-5-yl)phenyl)-1H-indazol-1-yl)(2,6-dichlorophenyl)methanone (16 mg).

ESI MS m/z 435 [M+H]$^+$.

Example 23

Following a procedure analogous to that described in Example 22, the following compound was prepared.
Org 356723-0

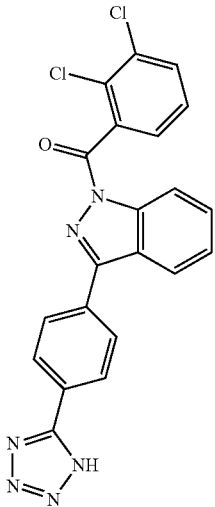 [SMILES: O=C(c1cccc(Cl)c1Cl)n1nc(-c2ccc(-c3nnn[nH]3)cc2)c2ccccc21]

(3-(1H-tetrazol-5-yl)phenyl)-1H-indazol-1-yl)(2,3-dichlorophenyl)methanone

ESI MS=m/z [M+H]$^+$

Example 24A

Preparation of sodium 4-(1-(2-chloro-6-(trifluoromethyl)benzoyl)-4-fluoro-1H-indazol-3-yl)-3-fluorobenzoate (24A)

SCHEME A.

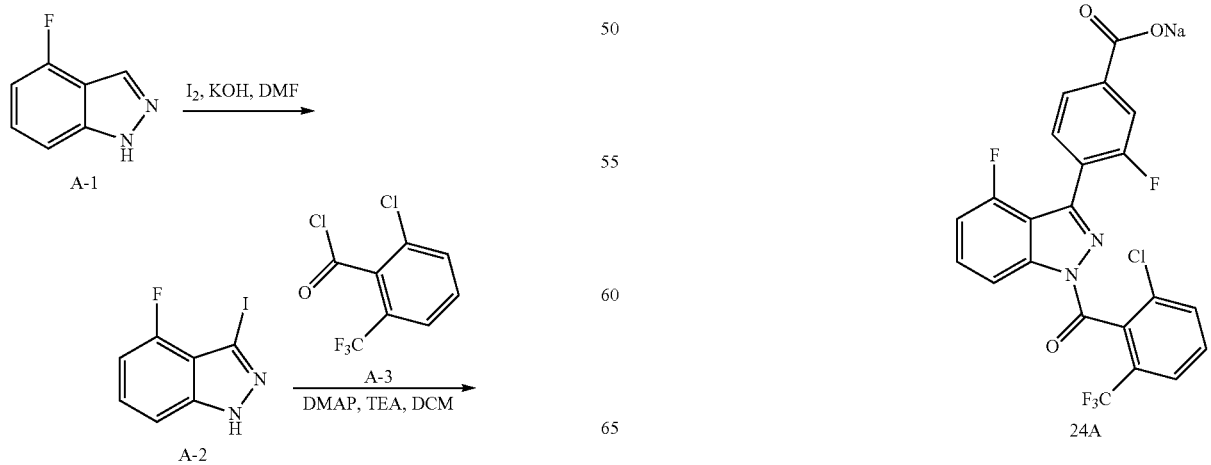

i) Preparation of 4-fluoro-3-iodo-1H-indazole (A-2)

To a solution of 4-fluoroindazole A-1 (5.00 g, 36.7 mmol) in DMF (80 mL) was added I$_2$ (18.6 g, 73.5 mmol) and KOH (7.73 g, 134 mmol) successively at rt. After 2 h, the reaction mixture was poured into aq. 10% NaHSO$_3$ (200 mL) and extracted with EtOAc (200 mL*3). The combined organic layers were washed with H$_2$O and brine, dried over Na$_2$SO$_4$, and concentrated. The crude solid was washed with PE to give the title compound as a yellow solid. LCMS (ESI) calc'd for C$_7$H$_5$FIN$_2$ [M+H]$^+$: 262.9. found: 262.9.

ii) Preparation of (2-chloro-6-(trifluoromethyl)phenyl)(4-fluoro-3-iodo-1H-indazol-1-yl)methanone (A-4)

To a flask was added compound A-2 (5.24 g, 20 mmol), compound A-3 (4.86 g, 20 mmol), DMAP (2.44 g, 20 mmol) and DCM (30 mL), followed by the addition of TEA (5.8 mL, 40 mmol) slowly. The reaction mixture was stirred at rt for 24 h. The mixture was diluted with H$_2$O, and the organic layer was separated. The aqueous layer was extracted with CH$_2$Cl$_2$. The combined organics were washed with H$_2$O, brine, dried over Na$_2$SO$_4$, and concentrated. The residue was purified by flash chromatography (Pentane/EtOAc) to afford the title compound. LCMS (ESI) calc'd for C$_{15}$H$_7$ClF$_4$IN$_2$O [M+H]$^+$: 468.9. found: 468.9.

iii) Preparation of methyl 4-(1-(2-chloro-6-(trifluoromethyl)benzoyl)-4-fluoro-1H-indazol-3-yl)-3-fluorobenzoate (A-5)

To a mixture of A-4 (300 mg, 0.64 mmol), 2-fluoro-4-(methoxycarbonyl)phenylboronic acid (190 mg, 0.96 mmol), Pd(dppf)Cl$_2$ (52 mg, 0.064 mmol) and KOAc (190 mg, 1.92 mmol) was added dioxane (10 ml) and H$_2$O (2 ml), and the mixture was heated at 90° C. under microwave for 2 h. The mixture was cooled down, diluted with CH$_2$Cl$_2$ (50 ml). The organic layer was separated, washed with brine, dried over Na$_2$SO$_4$, concentrated. The residue was purified by flash chromatography (Pentane/EtOAc) to give the title compound. LCMS (ESI) calc'd for C$_{23}$H$_{13}$ClF$_5$N$_2$O$_3$ [M+H]$^+$, 495. found: 495.

iv) Preparation of 4-(1-(2-chloro-6-(trifluoromethyl)benzoyl)-4-fluoro-1H-indazol-3-yl)-3-fluorobenzoic acid (A-6)

To a solution of A-5 (180 mg, 0.36 mmol) in THF (5 mL) and H$_2$O (5 mL) was added LiOH (350 mg, 1.44 mmol), and the mixture was stirred at rt for 24 h. The mixture was neutralized with 2N HCl to PH=3~4. The mixture was then concentrated under reduced pressure. The residue was filtered and washed with H$_2$O to afford the title compound as white solid. LCMS (ESI): calc'd for C$_{22}$H$_{11}$ClF$_5$N$_2$O$_3$ [M+H]$^+$: 481. found: 481; $^1$H NMR (400 MHz, CDCl$_3$) δ 8.45-8.47 (1H, d), 7.88-7.95 (2H, m), 7.66-7.71 (3H, m), 7.58-7.64 (2H, m), 7.13-7.17 (1H, m).

v) Preparation of sodium 4-(1-(2-chloro-6-(trifluoromethyl)benzoyl)-4-fluoro-1H-indazol-3-yl)-3-fluorobenzoate (24A)

To a suspension of compound A-6 (160 mg, 0.33 mmol) in H$_2$O (10 mL) was added 0.1M NaOH (3.3 ml, 0.33 mmol) and the mixture was kept stirring at 0° C. for 30 mins. The reaction mixture was dried under lyophilization to afford the title compound. LCMS (ESI) calc'd for C$_{22}$H$_{11}$ClF$_5$N$_2$O$_3$ [M-Na+2H]$^+$: 481. found: 481; $^1$HNMR (400 MHz, DMSO) δ 8.36-8.38 (1H, d), 7.96-8.03 (2H, m), 7.66-7.71 (1H, m), 7.85-7.89 (1H, m), 7.72-7.74 (1H, m), 7.65 (1H, s), 7.40-7.45 (2H, m).

Example 24B

Preparation of sodium 4-(1-(2-chloro-6-(trifluoromethyl)benzoyl)-1H-indazol-3-yl)benzoate (24B)

SCHEME B.

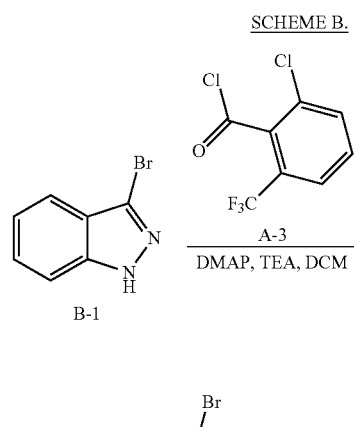

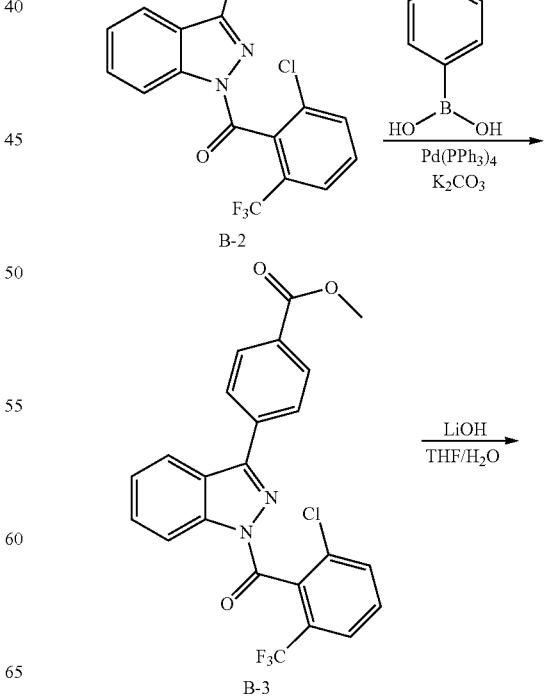

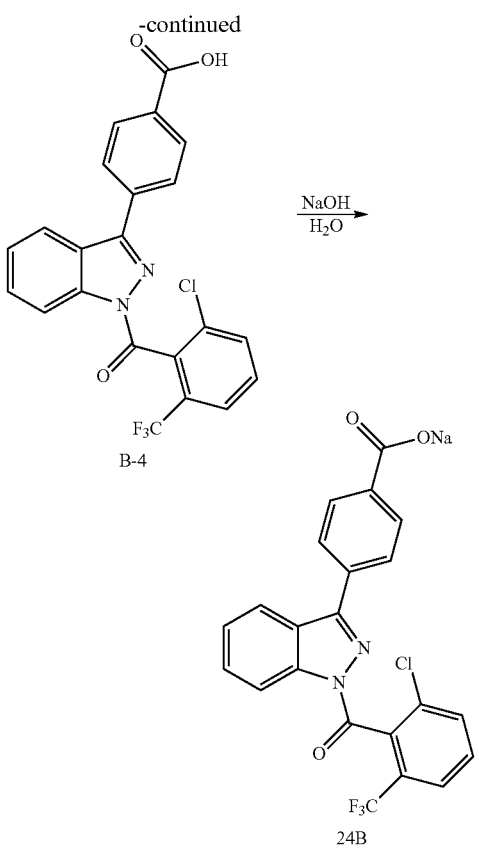

separated and washed with brine, dried over Na₂SO₄ and concentrated. The residue was purified by prep HPLC to give the title compound as a white solid. LCMS (ESI) calc'd for $C_{22}H_{13}ClF_3N_2O_3$ [M+H]⁺: 445. found: 445; ¹H NMR (400 MHz, CDCl₃) δ 8.68-8.71 (1H, d), 8.19-8.21 (2H, m), 8.03-8.05 (1H, d), 7.94-7.96 (2H, m), 7.70-7.75 (3H, m), 7.26-7.63 (2H, m).

iv) Preparation of sodium 4-(1-(2-chloro-6-(trifluoromethyl)benzoyl)-1H-indazol-3-yl)benzoate (24B)

To a suspension of compound B-4 (0.87 g, 2.0 mmol) in H₂O (10 mL) at 0° C. was added 0.1 M NaOH (2.0 ml, 2.0 mmol) and the mixture was kept stirring at 0° C. for 30 mins. The mixture was dried under lyophilization to give the title compound. ¹H NMR (400 MHz, DMSO) δ 8.54-8.56 (1H, d), 8.22-8.24 (1H, d), 8.03-8.05 (1H, d), 7.98-8.00 (3H, m), 7.82-7.88 (2H, m), 7.71-7.73 (2H, m), 7.63-7.67 (1H, t).

Example 24C

Preparation of sodium 4-(1-(2-chloro-6-(trifluoromethyl)benzoyl)-1H-pyrazolo[4,3-b]pyridin-3-yl)-3-fluorobenzoate (24C)

SCHEME C.

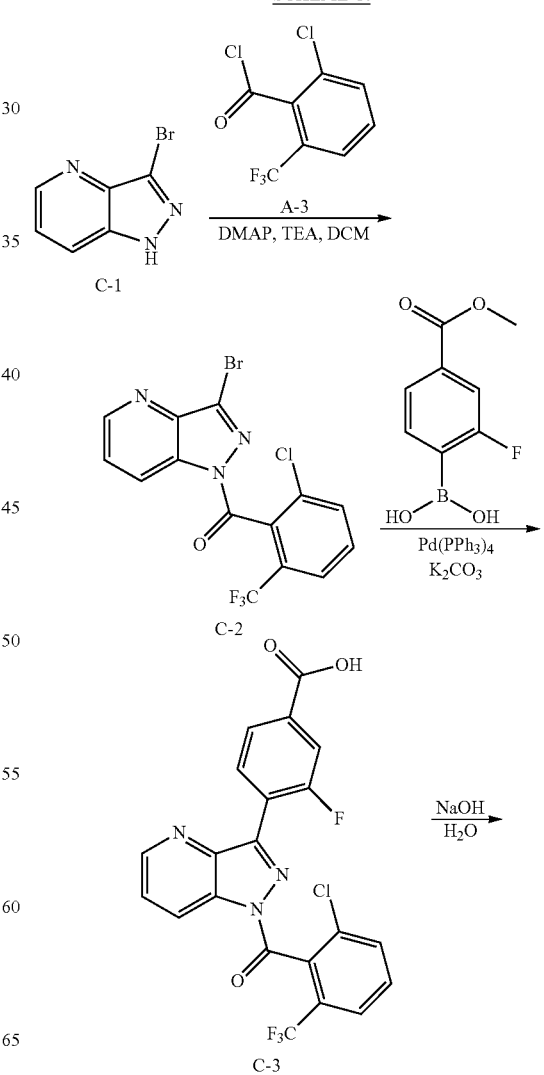

i) Preparation of (3-bromo-1H-indazol-1-yl)(2-chloro-6-(trifluoromethyl)phenyl)methanone (B-2)

To a solution of 3-bromo-1H-indazole (2 g, 0.75 mmol), DMAP (1 g, 8.5 mmol) and Et₃N (1.85 ml, 12.7 mmol) in CH₂Cl₂ (20 mL) at 0° C. was added a solution of compound A-3 (4 g, 20.4 mmol) in CH₂Cl₂ (5 mL). The mixture was stirred at rt for 24 h, diluted with CH₂Cl₂, washed with 1M HCl. The organic layer was washed with sat. NaHCO₃ and brine, dried over anhydrous Na₂SO₄ and concentrated. The residue was purified by flash chromatography (PE/EA=10/1) to give the title compound. LCMS (ESI) calc'd for $C_{15}H_8BrClF_3N_2O$ [M+H]: 404.9. Found: 404.9.

ii) Preparation of methyl 4-(1-(2-chloro-6-(trifluoromethyl)benzoyl)-1H-indazol-3-yl)benzoate (B-3)

A mixture of compound B-2 (3.0 g, 7.4 mmol), 4-(methoxycarbonyl)phenylboronic acid (1.6 g, 8.9 mmol), Pd(PPh₃)₄ (0.43 g, 0.37 mmol) and K₂CO₃ (2.04 g, 10.8 mmol) in dioxane (10 mL) and H₂O (2 mL) was heated at 140° C. for 2 h under microwave. The mixture was cooled down, diluted with CH₂Cl₂ and H₂O. The organic layer was washed with brine, dried over Na₂SO₄ and concentrated. The residue was purified by flash chromatography (PE/EA=10/1) to give the title compound as a yellow solid. LCMS (ESI) calc'd for $C_{23}H_{15}ClF_3N_2O_3$ [M+H]⁺: 459. found: 459.

iii) Preparation of 4-(1-(2-chloro-6-(trifluoromethyl)benzoyl)-1H-indazol-3-yl)benzoic acid (B-4)

A mixture of compound B-3 (1.3 g, 2.8 mmol) and LiOH (0.35 g, 8.4 mmol) in THF (5 mL) and H₂O (5 mL) was stirred at rt for 24 h. Then the mixture was neutralized with AcOH to PH<7, diluted with CH₂Cl₂ and H₂O. The organic layer was -continued

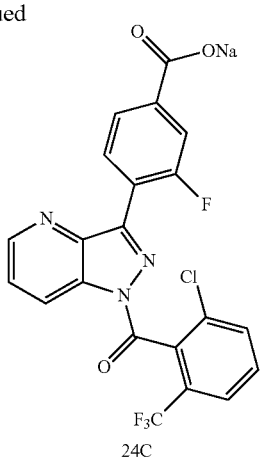

24C i) Preparation of (3-bromo-1H-pyrazolo[4,3-b]pyridin-1-yl)(2-chloro-6-(trifluoromethyl)phenyl)methanone (C-2)

To a mixture of compound A-3 (1.2 g, 5.0 mmol), compound C-1 (1.0 g, 5.0 mmol), and DMAP (0.61 g, 5.0 mmol) in CH$_2$Cl$_2$ (20 mL) was added TEA (0.55 g, 5.5 mmol) dropwise. The mixture was stirred at rt for 24 h., diluted with H$_2$O, and the organic layer was separated. The aqueous layer was extracted with CH$_2$Cl$_2$. The combined organics were washed with H$_2$O, brine, dried over Na$_2$SO$_4$, and concentrated. The residue was purified by column chromatography (PE/EA from 50/1 to 10/1) to give the title solid. LCMS (ESI) calc'd for C$_{14}$H$_7$BrClF$_3$N$_3$O [M+H]$^+$: 405.9. found: 405.9.

ii) Preparation of 4-(1-(2-chloro-6-(trifluoromethyl)benzoyl)-1H-pyrazolo[4,3-b]pyridin-3-yl)-3-fluorobenzoic acid (C-3)

A mixture of C-2 (120 mg, 0.3 mmol), 2-fluoro-4-(methoxycarbonyl)phenylboronic acid (89 mg, 0.45 mmol), Pd(PPh$_3$)$_4$ (18 mg, 0.015 mmol) and K$_2$CO$_3$ (128 mg, 0.75 mmol) in dioxane (3 mL) and H$_2$O (0.6 mL) was heated at 140° C. for 3 h under microwave. The mixture was cooled down and diluted with CH$_2$Cl$_2$ and H$_2$O. The organic layer was washed with brine, dried over Na$_2$SO$_4$ and concentrated. The residue was purified by flash chromatography (PE/EA=1/1) to give the title compound as a yellow solid. LCMS (ESI) calc'd for C$_{22}$H$_{13}$ClF$_4$N$_3$O$_3$ [M+H]$^+$: 464. found: 464; $^1$H NMR (400 MHz, DMSO) δ 13.51 (1H, s), 8.98-8.91 (2H, m), 8.42-8.38 (2H, t), 8.06-7.95 (3H, m), 7.90-7.87 (2H, m), 7.87-7.80 (1H, m).

iii) Preparation of sodium 4-(1-(2-chloro-6-(trifluoromethyl)benzoyl)-1H-pyrazolo[4,3-b]pyridin-3-yl)-3-fluorobenzoate (24C)

To a suspension of compound C-3 (135 mg, 0.29 mmol) in H$_2$O (20 mL) was added 0.1 M NaOH (2.9 ml, 0.29 mmol) at 0° C., and the mixture was kept stirring for 30 min at 0° C. The mixture was then dried under lyophilization to give the title compound. LCMS (ESI) calc'd for C$_{21}$H$_{11}$ClF$_4$N$_3$O$_3$ [M-Na+2H]$^+$: 464. found: 464, $^1$H NMR (400 MHz, CD$_3$OD) δ 8.95-8.93 (1H, m), 8.89-8.87 (1H, m), 8.13-8.09 (1H, t), 7.90-7.87 (3H, m), 7.81-7.75 (3H, m).

The following examples shown in TABLE 2 were prepared following similar procedures described for Examples #24A, B, C in Schemes A-C, which can be achieved by those of ordinary skill in the art.

TABLE 2

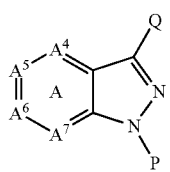

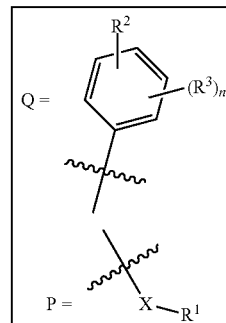

| Ex. | IUPAC name | A ring | P | Q | NMR or LCMS [M + H]$^+$ (found) |
|---|---|---|---|---|---|
| 24D | (2-chloro-6-(trifluoromethyl)phenyl)(4-fluoro-3-(4-(1,1,1,3,3,3-hexafluoro-2-hydroxypropan-2-yl)phenyl)-1H-indazol-1-yl)methanone | (2-fluorophenyl structure) | (2-chloro-6-(trifluoromethyl)benzoyl structure) | (4-(1,1,1,3,3,3-hexafluoro-2-hydroxypropan-2-yl)phenyl structure) | 585 |

TABLE 2-continued

| Ex. | IUPAC name | A ring | P | Q | NMR or LCMS [M + H]+ (found) |
|---|---|---|---|---|---|
| 24E | 3-(1-(2-chloro-6-(trifluoromethyl)benzoyl)-4-fluoro-1H-indazol-3-yl)benzoic acid | | | | 463 |
| 24F | 2-(3-(1-(2-chloro-6-(trifluoromethyl)benzoyl)-4-fluoro-1H-indazol-3-yl)phenyl)acetic acid | | | | 477 |
| 24G | 2-(4-(1-(2-chloro-6-(trifluoromethyl)benzoyl)-4-fluoro-1H-indazol-3-yl)phenyl)acetic acid | | | | 477 |
| 24H | 2-chloro-4-(1-(2-chloro-6-(trifluoromethyl)benzoyl)-4-fluoro-1H-indazol-3-yl)benzoic acid | | | | 497 |

TABLE 2-continued

| Ex. | IUPAC name | A ring | P | Q | NMR or LCMS [M + H]+ (found) |
|---|---|---|---|---|---|
| 24I | Sodium 3-chloro-4-(1-(2-chloro-6-(trifluoromethyl)benzoyl)-4-fluoro-1H-indazol-3-yl)benzoate | | | | 497 |
| 24J | 4-(1-(2-chloro-6-(trifluoromethyl)benzoyl)-4-fluoro-1H-indazol-3-yl)benzamide | | | | 462 |
| 24K | 4-(1-(2-chloro-6-(trifluoromethyl)benzoyl)-4-fluoro-1H-indazol-3-yl)-2-fluoro-5-methylbenzoic acid | | | | 495 |
| 24L | 4-(1-(2-chloro-6-(trifluoromethyl)benzoyl)-4-fluoro-1H-indazol-3-yl)-3-methylbenzoic acid | | | | 477 |

TABLE 2-continued

| Ex. | IUPAC name | A ring | P | Q | NMR or LCMS [M + H]+ (found) |
|---|---|---|---|---|---|
| 24M | 4-(1-(2-chloro-6-(trifluoromethyl)benzoyl)-4-fluoro-1H-indazol-3-yl)-2-methoxybenzoic acid | | | | 494 |
| 24N | 4-(1-(2-chloro-6-(trifluoromethyl)benzoyl)-4-fluoro-1H-indazol-3-yl)-2-fluorobenzoic acid | | | | 481 |
| 24O | sodium 4-(1-(2-chloro-6-(trifluoromethyl)benzoyl)-4-fluoro-1H-indazol-3-yl)-2-fluorobenzoate | | | | 481 [M − Na + 2H]+ |
| 24P | 4-(1-(2-chloro-6-(trifluoromethyl)benzoyl)-4-fluoro-1H-indazol-3-yl)-2-methylbenzoic acid | | | | 483 |

TABLE 2-continued

| Ex. | IUPAC name | A ring | P | Q | NMR or LCMS [M + H]+ (found) |
|---|---|---|---|---|---|
| 24Q | 4-(1-(2-chloro-6-(trifluoromethyl)benzoyl)-4-fluoro-1H-indazol-3-yl)-3-methoxybenzoic acid | | | | 493 |
| 24R | 4-(1-(2-chloro-6-(trifluoromethyl)benzoyl)-4-fluoro-1H-indazol-3-yl)-2,6-difluorobenzoic acid | | | | 499 |
| 24S | 4-(1-(2-chloro-6-(trifluoromethyl)benzoyl)-4-fluoro-1H-indazol-3-yl)-2-isopropylbenzoic acid | | | | 505 |
| 24T | 4-(1-(2-chloro-6-(trifluoromethyl)benzoyl)-4-fluoro-1H-indazol-3-yl)-3,5-dimethoxybenzoic acid | | | | 523 |

TABLE 2-continued

| Ex. | IUPAC name | A ring | P | Q | NMR or LCMS [M + H]+ (found) |
|---|---|---|---|---|---|
| 24U | 4-(1-(2-chloro-6-(trifluoromethyl)benzol)-4-fluoro-1H-indazol-3-yl)-2-cyano benzoic acid | | | | 488 |
| 24V | 4-(1-(2-chloro-6-(trifluoromethyl)benzoyl)-4-fluoro-1H-indazol-3-yl)-2,3-difluorobenzoic acid | | | | 499 |
| 24W | 4-(1-(2-chloro-6-(trifluoromethyl)benzoyl)-4-fluoro-1H-indazol-3-yl)-2,5-difluorobenzoic acid | | | | 499 |
| 24X | 2-chloro-4-(1-(2-chloro-6-(trifluoromethyl)benzoyl)-4-fluoro-1H-indazol-3-yl)-5-fluorobenzoic acid | | | | 515 |

TABLE 2-continued

| Ex. | IUPAC name | A ring | P | Q | NMR or LCMS [M + H]+ (found) |
|---|---|---|---|---|---|
| 24Y | 4-(1-(2-chloro-6-(trifluoromethyl)benzoyl)-4-fluoro-1H-indazol-3-yl)-5-fluoro-2-methoxybenzoic acid | | | | 511 |
| 24Z | 5-(1-(2-chloro-6-(trifluoromethyl)benzoyl)-4-fluoro-1H-indazol-3-yl)-2-hydroxybenzoic acid | | | | 479 |
| 24AA | 3-fluoro-4-(4-fluoro-1-(2-fluoro-6-methoxybenzoyl)-1H-indazol-3-yl)benzoic acid | | | | 427 |
| 24AB | 4-(4-fluoro-1-(2-fluoro-6-methoxybenzoyl)-1H-indazol-3-yl)benzoic acid | | | | 409 |
| 24AC | 3-(1-(2-chloro-6-(trifluoromethyl)benzoyl)-1H-pyrazolo[4,3-b]pyridin-3-yl)benzoic acid | | | | 446 |

TABLE 2-continued

| Ex. | IUPAC name | A ring | P | Q | NMR or LCMS [M + H]+ (found) |
|---|---|---|---|---|---|
| 24AD | 2-(4-(1-(2-chloro-6-(trifluoromethyl)benzoyl)-1H-pyrazolo[4,3-b]pyridin-3-yl)phenyl)acetic acid | | | | 460 |
| 24AE | (2-chloro-6-(trifluoromethyl)phenyl)(3-(4-(1,1,1,3,3,3-hexafluoro-2-hydroxypropan-2-yl)phenyl)-1H-pyrazolo[4,3-b]pyridin-1-yl)methanone | | | | 568 |
| 24AF | 4-(1-(2-chloro-6-(trifluoromethyl)benzoyl)-1H-pyrazolo[4,3-b]pyridin-3-yl)-3-methylbenzoic acid | | | | 460 |
| 24AG | 3-chloro-4-(1-(2-chloro-6-(trifluoromethyl)benzoyl)-1H-pyrazolo[4,3-b]pyridin-3-yl)benzoic acid | | | | 480 |

TABLE 2-continued

| Ex. | IUPAC name | A ring | P | Q | NMR or LCMS [M + H]+ (found) |
|---|---|---|---|---|---|
| 24AH | 4-(1-(2-chloro-6-(trifluoromethyl)benzoyl)-1H-pyrazolo[4,3-b]pyridin-3-yl)-2-fluorobenzoic acid | | | | 464 |
| 24AI | 4-(1-(2-chloro-6-(trifluoromethyl)benzoyl)-1H-pyrazolo[4,3-b]pyridin-3-yl)-2-methoxybenzoic acid | | | | 476 |
| 24AJ | 2-chloro-4-(1-(2-chloro-6-(trifluoromethyl)benzoyl)-1H-pyrazolo[4,3-b]pyridin-3-yl)-5-fluorobenzoic acid | | | | 498 |
| 24AK | 4-(1-(2-chloro-6-(trifluoromethyl)benzoyl)-1H-pyrazolo[4,3-b]pyridin-3-yl)-2,5-difluorobenzoic acid | | | | 482 |

TABLE 2-continued
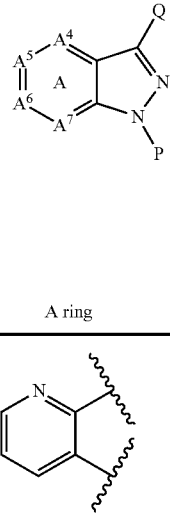
| Ex. | IUPAC name | A ring | P | Q | NMR or LCMS [M + H]+ (found) |
|---|---|---|---|---|---|
| 24AL | 5-(1-(2-chloro-6-(trifluoromethyl)benzoyl)-1H-pyrazolo[4,3-b]pyridin-3-yl)-2-hydroxybenzoic acid | 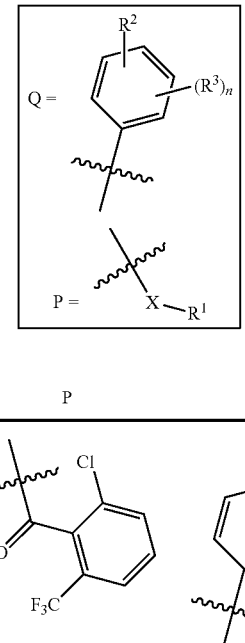 | 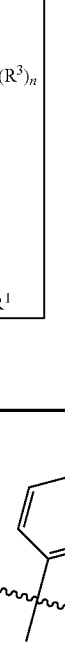 | 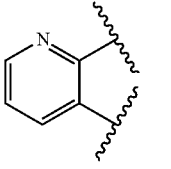 [SMILES: *c1cccnc1*] | 462 |
| 24AM | 4-(1-(2-fluoro-6-methoxybenzoyl)-1H-pyrazolo[4,3-b]pyridin-3-yl)benzoic acid | 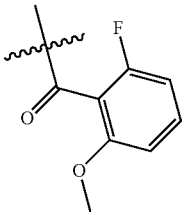 [SMILES: *C(=O)c1c(F)cccc1OC] | 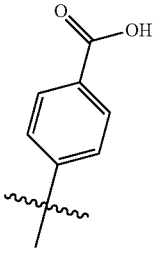 [SMILES: *c1ccc(C(=O)O)cc1] | 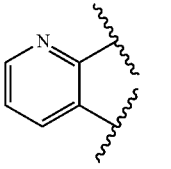 [SMILES: *c1cccnc1*] | 392 |
| 24AN | 3-fluoro-4-(1-(2-fluoro-6-methoxybenzoyl)-1H-pyrazolo[4,3-b]pyridin-3-yl)benzoic acid | 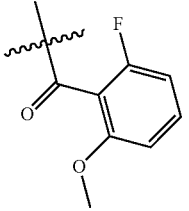 [SMILES: *C(=O)c1c(F)cccc1OC] | 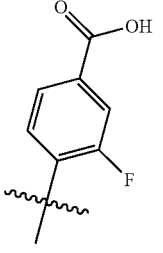 [SMILES: *c1ccc(C(=O)O)cc1F] | 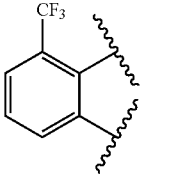 | 410 |
| 24AO | 4-(1-(2-chloro-6-(trifluoromethyl)benzoyl)-4-(trifluoromethyl)-1H-indazol-3-yl)benzoic acid | 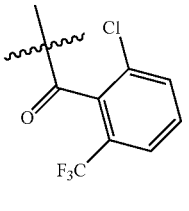 [SMILES: *C(=O)c1c(Cl)cccc1C(F)(F)F] | 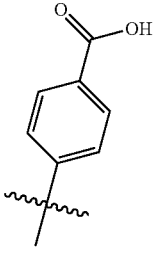 [SMILES: *c1ccc(C(=O)O)cc1] | | 513 |

TABLE 2-continued

| Ex. | IUPAC name | A ring | P | Q | NMR or LCMS [M + H]+ (found) |
|---|---|---|---|---|---|
| 24AP | 4-(1-(2-chloro-6-(trifluoromethyl)benzoyl)-1H-indazol-3-yl)-2-isopropylbenzoic acid | | | | 487 |
| 24AQ | sodium 4-(1-(2-chloro-6-(trifluoromethyl)benzoyl)-1H-indazol-3-yl)-2-fluoro benzoate | | | | 463 [M − Na + 2H]+ |
| 24AR | sodium 4-(1-(2-chloro-6-(trifluoromethyl)benzoyl)-1H-indazol-3-yl)-3-fluoro benzoate | | | | 463 [M − Na + 2H]+ |
| 24AS | 3-chloro-4-(1-(2-chloro-6-(trifluoromethyl)benzoyl)-1H-indazol-3-yl)benzoic acid | | | | 480 |

TABLE 2-continued
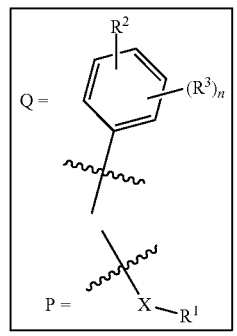
| Ex. | IUPAC name | A ring | P | Q | NMR or LCMS [M + H]+ (found) |
|---|---|---|---|---|---|
| 24AT | 3-fluoro-4-(1-(2-fluoro-6-methoxybenzoyl)-1H-indazol-3-yl)benzoic acid | | | | 409 |
| 24AU | sodium 3-fluoro-4-(1-(2-fluoro-6-methoxybenzoyl)-1H-indazol-3-yl)benzoate | | | | 409 [M − Na + 2H]+ |
| 24AV | 4-(7-fluoro-1-(2-fluoro-6-methoxybenzoyl)-1H-indazol-3-yl)benzoic acid | | | | 409 |
| 24AW | 3-fluoro-4-(7-fluoro-1-(2-fluoro-6-methoxybenzoyl)-1H-indazol-3-yl)benzoic acid | | | | 427 |

TABLE 2-continued

| Ex. | IUPAC name | A ring | P | Q | NMR or LCMS [M + H]+ (found) |
|---|---|---|---|---|---|
| 24AX | 4-(6-bromo-1-(2-chloro-6-(trifluoromethyl)benzoyl)-4-fluoro-1H-indazol-3-yl)benzoic acid | | | | 543 |
| 24AY | 4-(6-bromo-1-(2-chloro-6-(trifluoromethyl)benzoyl)-1H-indazol-3-yl)benzoic acid | | | | 1H NMR (400 MHz, DMSO) δ 13.25 (1H, s), 8.72 (1H, s), 8.23 (1H, d, J = 8.4 Hz), 8.01-8.11 (4H, m), 7.86-7.96 (4H, m) |
| 24AZ | 4-(1-(2-chloro-6-(trifluoromethyl)benzoyl)-4-fluoro-6-methoxy-1H-indazol-3-yl)benzoic acid | | | | 493 |
| 24BA | 4-(1-(2-chloro-6-(trifluoromethyl)benzoyl)-6-hydroxy-1H-indazol-3-yl)benzoic acid | | | | 461 |

TABLE 2-continued

| Ex. | IUPAC name | A ring | P | Q | NMR or LCMS [M + H]+ (found) |
|---|---|---|---|---|---|
| 24BB | 4-(1-(2-chloro-6-(trifluoromethyl)benzoyl)-6-hydroxy-1H-indazol-3-yl)-3-fluorobenzoic acid | | | | 479 |
| 24BC | 4-(1-(2-chloro-6-(trifluoromethyl)benzoyl)-4-fluoro-6-hydroxy-1H-indazol-3-yl)benzoic acid | | | | 479 |
| 24BD | 4-(1-(2-chloro-6-(trifluoromethyl)benzoyl)-4-fluoro-6-hydroxy-1H-indazol-3-yl)-3-fluorobenzoic acid | | | | 497 |
| 24BE | 4-(1-(2-chloro-6-(trifluoromethyl)benzoyl)-6-(hydroxymethyl)-1H-indazol-3-yl)benzoic acid | | | | 475 |

TABLE 2-continued
| Ex. | IUPAC name | A ring | P | Q | NMR or LCMS [M + H]+ (found) |
|---|---|---|---|---|---|
| 24BF | 4-(1-(2-chloro-6-(trifluoromethyl)benzoyl)-6-(hydroxymethyl)-1H-indazol-3-yl)-3-fluorobenzoic acid | | | | 493 |
| 24BG | 4-(1-(2-chloro-6-(trifluoromethyl)benzoyl)-6-(methoxymethyl)-1H-indazol-3-yl)benzoic acid | | | | 489 |
Example 25A
Preparation of sodium 4-(1-(2-chloro-6-(trifluoromethyl)benzoyl)-6-(2-hydroxy ethylcarbamoyl)-1H-indazol-3-yl)benzoate (25A)
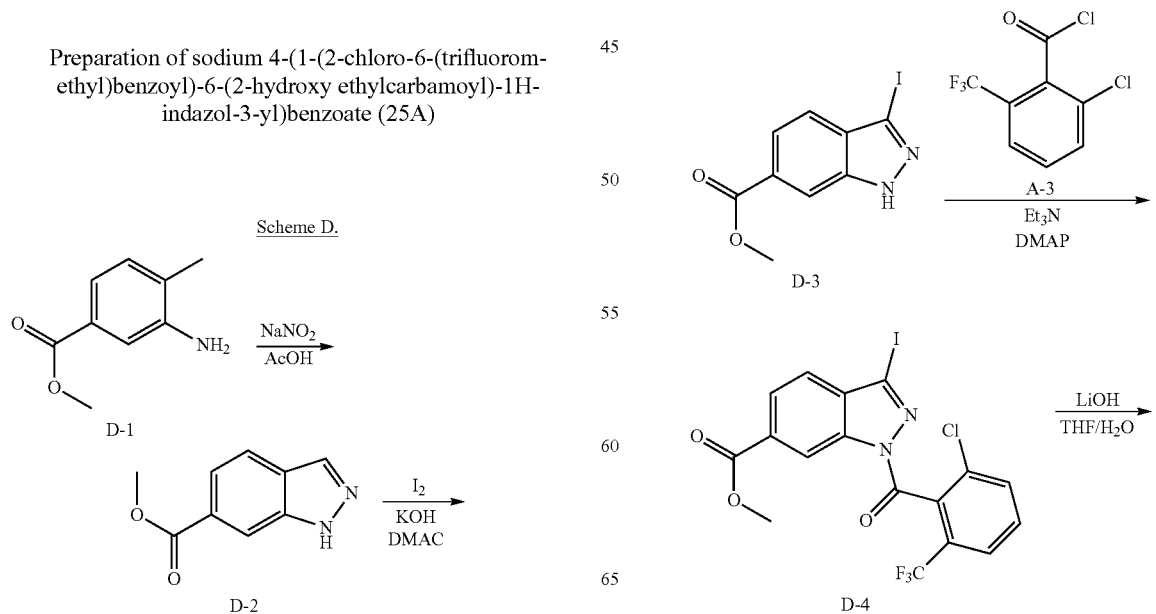

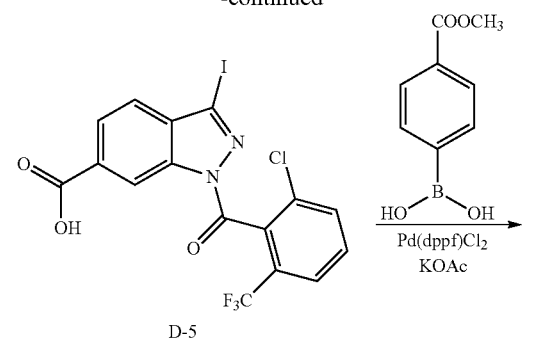

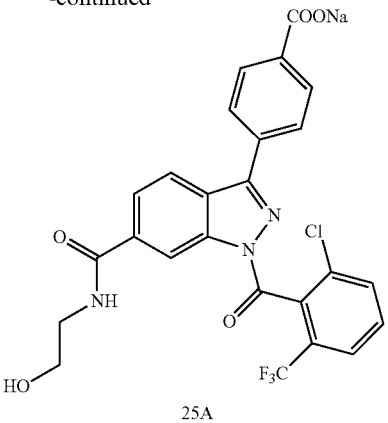

i) Preparation of methyl 1H-indazole-6-carboxylate (D-2)

To a solution of methyl 3-amino-4-methylbenzoate D-1 (5.0 g, 30 mmol) in AcOH (140 mL) at 0° C. was added a solution of sodium nitrite (2.1 g, 30 mmol) in H$_2$O (3.5 mL). After addition, the mixture was stirred at rt for 24 h. Then half of the solvent was removed under reduced pressure and the resulting mixture was diluted with H$_2$O, and extracted with EtOAc. The combined organics were washed H$_2$O and brine, and concentrated to give the title compound. LCMS (ESI) calc'd for C$_9$H$_9$N$_2$O$_2$ [M+H]$^+$: 177. found 177.

ii) Preparation of methyl 3-iodo-1H-indazole-6-carboxylate (D-3)

To a solution of methyl 1H-indazole-6-carboxylate D-2 (5.0 g, 28 mmol) in DMAC (50 mL) at 0° C. was added iodine (14.4 g, 56.7 mmol) and potassium hydroxide (6.3 g, 114 mmol) portionwise. After addition, the mixture was kept stirring for 1 h, then quenched with aq. Na$_2$S$_2$O$_3$ and extracted with EtOAc. The combined organics were concentrated and trituated with hexane. The precipitate was collected by filtration to afford the title compound as a brown solid. LCMS (ESI) calc'd for C$_9$H$_8$IN$_2$O$_2$ [M+H]$^+$: 302.9. found: 302.9.

iii): Preparation of methyl 1-(2-chloro-6-(trifluoromethyl)benzoyl)-3-iodo-1H-indazole-6-carboxylate (D-4)

To a solution of methyl 3-iodo-1H-indazole-6-carboxylate D-3 (11.7 g, 38.7 mmol), DMAP (4.72 g, 38.7 mmol) in CH$_2$Cl$_2$ (30 mL) was added Et$_3$N (11.2 mL, 77 mmol) dropwise. The reaction mixture was stirred at rt for 24 h, diluted with H$_2$O, and the organic layer was separated. The aqueous layer was extracted with CH$_2$Cl$_2$ twice. The combined organics were washed with H$_2$O, brine, dried over Na$_2$SO$_4$, concentrated. The residue was purified by column chromatography (PE/EtOAc from 50/1 to 10/1) to give the title compound. LCMS (ESI) calc'd for C$_{17}$H$_{10}$ClF$_3$IN$_2$O$_3$ [M+H]$^+$: 508.9. found: 508.9.

iv): Preparation of 1-(2-chloro-6-(trifluoromethyl)benzoyl)-3-iodo-1H-indazole-6-carboxylic acid (D-5)

To a solution of D-4 (16.5 g, 32.5 mmol) in THF (10 mL) and H$_2$O (50 ml) was added LiOH (3.40 g, 162 mmol), and the mixture was stirred at rt for 24 h. The solvent was removed under reduced pressure and the residue was taken up in H$_2$O, and neutralized with 5% aqueous HCl to PH=4~5. The white precipitate was collected by filtration, washed with H$_2$O and hexane to give the title compound as an off-white solid. LCMS (ESI) calc. C$_{16}$H$_8$ClF$_3$IN$_2$O$_3$ [M+H]$^+$: 494.9. found: 494.9.

v) Preparation of 1-(2-chloro-6-(trifluoromethyl) benzoyl)-3-(4-(methoxy carbonyl)phenyl)-1H-indazole-6-carboxylic acid (D-6)

A mixture of D-5 (300 mg, 0.61 mmol), 4-(methoxycarbonyl)phenylboronic acid (165 mg, 0.92 mmol), Pd(dppf)Cl$_2$ (50 mg, 0.061 mmol) and KOAc (181 mg, 1.83 mmol) in dioxane (10 mL) and H$_2$O (2 mL) was heated at 95° C. for 2 h under microwave. The mixture was then cooled to rt, diluted with EtOAc and H$_2$O. The organic layer was washed with brine, dried over Na$_2$SO$_4$ and concentrated. The residue was purified by flash chromatography (PE/EtOAc=20/1) to give the title compound as a white solid. LCMS (ESI) calc'd for C$_{24}$H$_{15}$ClF$_3$N$_2$O$_5$ [M+H]$^+$: 503.1. found: 503.1.

vi) Preparation of methyl 4-(1-(2-chloro-6-(trifluoromethyl)benzoyl)-6-(2-hydroxyethylcarbamoyl)-1H-indazol-3-yl)benzoate (D-7)

To a solution of compound D-6 (180 mg, 0.36 mmol) in CH$_2$Cl$_2$ (15 mL) was added PYAOP (374 mg, 0.72 mmol), followed by the addition of Et$_3$N (0.16 mL, 1.1 mmol). The mixture was stirred at rt for 2 h, diluted with EtOAc. The organic layer was separated, washed with brine, dried over Na$_2$SO$_4$, concentrated to give the title compound as a white solid. LCMS (ESI) calc'd for C$_{26}$H$_{20}$ClF$_3$N$_3$O$_5$ [M+H]$^+$: 546.1. Found: 546.1.

vii) Preparation of 4-(1-(2-chloro-6-(trifluoromethyl) benzoyl)-6-(2-hydroxy ethylcarbamoyl)-1H-indazol-3-yl)benzoic acid (D-8)

A mixture of D-7 (191 mg, 0.35 mmol) and LiOH (42 mg, 1.75 mmol) in THF (10 mL) and H$_2$O (5 mL) was stirred at rt for 2 h. The solvent was removed under reduced pressure, and the residue was dissolved in H$_2$O and neutralized with aqueous 5% HCl to PH=4-5. The precipitated was collected by filtration, washed with H$_2$O and hexane to the title compound as an off-white solid. LCMS (ESI) calc'd for C$_{25}$H$_{18}$ClF$_3$N$_3$O$_5$ [M+H]$^+$: 532.1. found: 532.1; $^1$H NMR (400 MHz, MeOD) δ 9.109 (1H, s), 8.29-8.31 (1H, d, J=8.4 Hz), 8.17-8.19 (2H, d, J=8.4 Hz), 8.07-8.10 (1H, m), 7.97-8.00 (2H, d, J=8.8 Hz), 7.88-7.99 (2H, m), 7.78-7.82 (1H, m), 3.79-3.82 (2H, m), 3.60-3.63 (2H, m).

viii) Preparation of sodium 4-(1-(2-chloro-6-(trifluoromethyl)benzoyl)-6-(2-hydroxyethylcarbamoyl)-1H-indazol-3-yl)benzoate (25A)

To a suspension of compound D-8 (185 mg, 0.35 mmol) in H$_2$O (10 mL) was added 0.1M NaOH (3.5 ml, 0.35 mmol) at 0° C., and the mixture was kept stirring for 30 mins. The mixture was then dried under lyophilizaiton to give the title compound. LCMS (ESI) calc. C$_{25}$H$_{18}$ClF$_3$N$_3$O$_5$ [M-Na+2H]$^+$: 532. found: 532; $^1$H NMR (400 MHz, MeOD) δ 9.09 (1H, s), 8.28-8.30 (1H, d, J=8.8 Hz), 8.05-8.09 (3H, m), 7.86-7.91 (4H, m), 7.77-7.86 (1H, m), 3.79-3.82 (2H, m), 3.60-3.63 (2H, m).

The following examples shown in TABLE 3 were prepared following similar procedures described for Example #25A in Scheme D, which can be achieved by those of ordinary skill in the art.

TABLE 3

| Ex. | IUPAC name | R$^9$R$^{10}$N- | P | Q | LCMS [M + H]$^+$ (found) |
|---|---|---|---|---|---|
| 25B | 4-(1-(2-chloro-6-(trifluoromethyl)benzoyl)-6-(dimethylcarbamoyl)-1H-indazol-3-yl)benzoic acid | dimethylamino | 2-chloro-6-(trifluoromethyl)benzoyl | 4-carboxyphenyl | 516 |

TABLE 3-continued

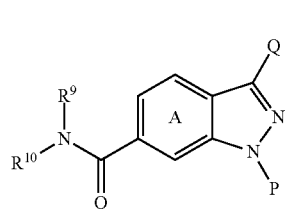

| Ex. | IUPAC name | 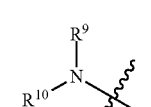 | P | Q | LCMS [M + H]+ (found) |
|---|---|---|---|---|---|
| 25C | 4-(1-(2-chloro-6-(trifluoro-methyl)benzoyl)-6-(2-hydroxyethylcarbamoyl)-1H-indazol-3-yl)benzoic acid | 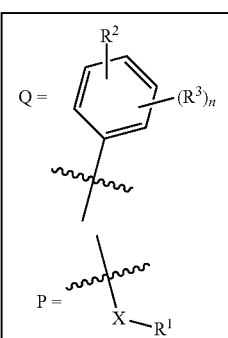 | 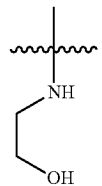 | 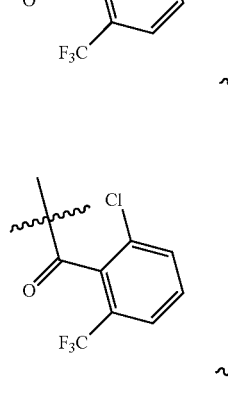 | 532 |
| 25D | sodium 4-(1-(2-chloro-6-(trifluoromethyl)benzoyl)-6-(2-hydroxyethylcarbamoyl)-1H-indazol-3-yl)benzoate | 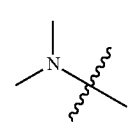 [SMILES: *N(C)C] | 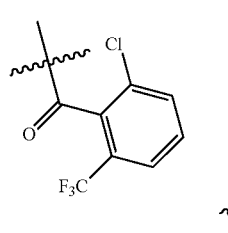 | 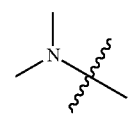 [SMILES: *N(C)C] | 554 |
| 25E | 4-(1-(2-chloro-6-(trifluoro-methyl)benzoyl)-6-(dimethylcarbamoyl)-1H-indazol-3-yl)-3-fluorobenzoic acid | 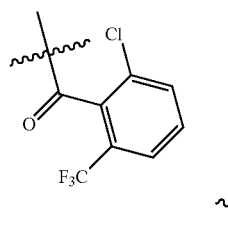 | | | 534 |
| 25F | sodium 4-(1-(2-chloro-6-(trifluoromethyl)benzoyl)-6-(dimethylcarbamoyl)-1H-indazol-3-yl)-3-fluorobenzoate | | | | 556 |

TABLE 3-continued

| Ex. | IUPAC name | R9R10N- | P | Q | LCMS [M + H]+ (found) |
|---|---|---|---|---|---|
| 25G | 4-(1-(2-chloro-6-(trifluoromethyl)benzoyl)-6-(2-hydroxyethylcarbamoyl)-1H-indazol-3-yl)-2-fluorobenzoic acid | -NH-CH2CH2OH | 2-chloro-6-(trifluoromethyl)benzoyl | 4-carboxy-3-fluorophenyl | 550 |
| 25H | 4-(1-(2-chloro-6-(trifluoromethyl)benzoyl)-6-(2-hydroxyethylcarbamoyl)-1H-indazol-3-yl)-3-fluorobenzoic acid | -NH-CH2CH2OH | 2-chloro-6-(trifluoromethyl)benzoyl | 4-carboxy-2-fluorophenyl | 550 |
| 25I | 4-(1-(2-chloro-6-(trifluoromethyl)benzoyl)-6-(dimethylcarbamoyl)-1H-indazol-3-yl)-2-fluorobenzoic acid | -N(CH3)2 | 2-chloro-6-(trifluoromethyl)benzoyl | 4-carboxy-3-fluorophenyl | 534 |
| 25J | 3-chloro-4-(1-(2-chloro-6-(trifluoromethyl)benzoyl)-6-(dimethylcarbamoyl)-1H-indazol-3-yl)benzoic acid | -N(CH3)2 | 2-chloro-6-(trifluoromethyl)benzoyl | 4-carboxy-2-chlorophenyl | 550 |

TABLE 3-continued

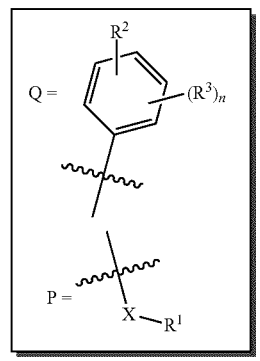

| Ex. | IUPAC name | R9R10N- | P | Q | LCMS [M + H]+ (found) |
|---|---|---|---|---|---|
| 25K | 3-chloro-4-(1-(2-chloro-6-(trifluoromethyl)benzoyl)-6-(2-hydroxyethylcarbamoyl)-1H-indazol-3-yl)benzoic acid | | | | 566 |
| 25L | 4-(1-(2-chloro-6-(trifluoromethyl)benzoyl)-6-(3-hydroxypropylcarbamoyl)-1H-indazol-3-yl)benzoic acid | | | | 546 |
| 25M | 4-(1-(2-chloro-6-(trifluoromethyl)benzoyl)-6-(3-hydroxypropylcarbamoyl)-1H-indazol-3-yl)-3-fluorobenzoic acid | | | | 564 |
| 25N | 4-(1-(2-chloro-6-(trifluoromethyl)benzoyl)-6-(3-methoxypropylcarbamoyl)-1H-indazol-3-yl)-3-fluorobenzoic acid | | | | 580 |

TABLE 3-continued

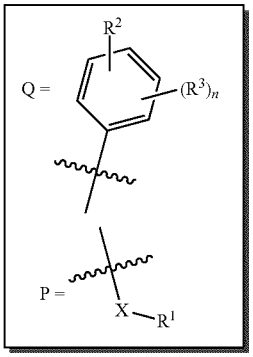

| Ex. | IUPAC name | R⁹R¹⁰N— | P | Q | LCMS [M + H]⁺ (found) |
|---|---|---|---|---|---|
| 25O | 4-(1-(2-chloro-6-(trifluoro-methyl)benzoyl)-6-(2-hydroxypropylcarbamoyl)-1H-indazol-3-yl)benzoic acid | | | | 546 |
| 25P | 4-(1-(2-chloro-6-(trifluoro-methyl)benzoyl)-6-(4-hydroxybutylcarbamoyl)-1H-indazol-3-yl)benzoic acid | | | | 560 |
| 25Q | 4-(1-(2-chloro-6-(trifluoro-methyl)benzoyl)-6-((2-hydroxy-ethyl)(methyl)carbamoyl)-1H-indazol-3-yl)benzoic acid | | | | 546 |
| 25R | 4-(1-(2-chloro-6-(trifluoro-methyl)benzoyl)-6-((2-hydroxy-ethyl)(methyl)carbamoyl)-1H-indazol-3-yl)-3-fluorobenzoic acid | | | | 564 |

TABLE 3-continued

| Ex. | IUPAC name | R9R10N- | P | Q | LCMS [M + H]+ (found) |
|---|---|---|---|---|---|
| 25S | 4-(1-(2-chloro-6-(trifluoro-methyl)benzoyl)-6-((2-methoxy-ethyl)(methyl)carbamoyl)-1H-indazol-3-yl)-3-fluorobenzoic acid | 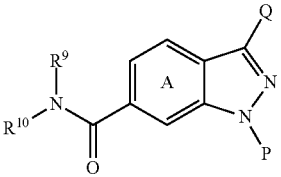 | 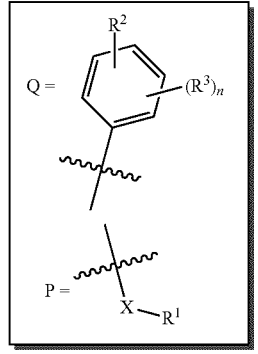 | 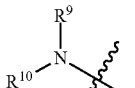 | 578 |
| 25T | 4-(1-(2-chloro-6-(trifluoro-methyl)benzoyl)-6-(3-fluoroazetidine-1-carbonyl)-1H-indazol-3-yl)benzoic acid | 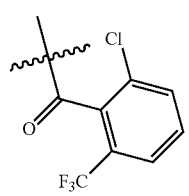 [SMILES: *C(=O)c1c(Cl)cccc1C(F)(F)F] | 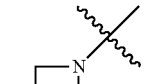 | 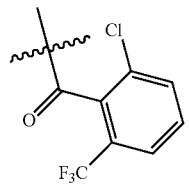 [SMILES: *C(=O)c1c(Cl)cccc1C(F)(F)F] | 546 |
| 25U | 4-(1-(2-chloro-6-(trifluoro-methyl)benzoyl)-6-(3,3-difluoroazetidine-1-carbonyl)-1H-indazol-3-yl)benzoic acid | 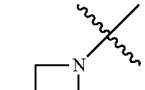 | 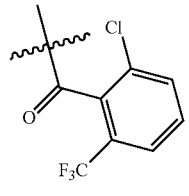 [SMILES: *C(=O)c1c(Cl)cccc1C(F)(F)F] | 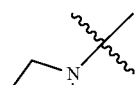 | 564 |
| 25V | 4-(1-(2-chloro-6-(trifluoro-methyl)benzoyl)-6-(pyrrolidine-1-carbonyl)-1H-indazol-3-yl)benzoic acid | 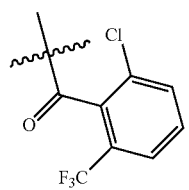 [SMILES: *C(=O)c1c(Cl)cccc1C(F)(F)F] | | | 542 |

TABLE 3-continued

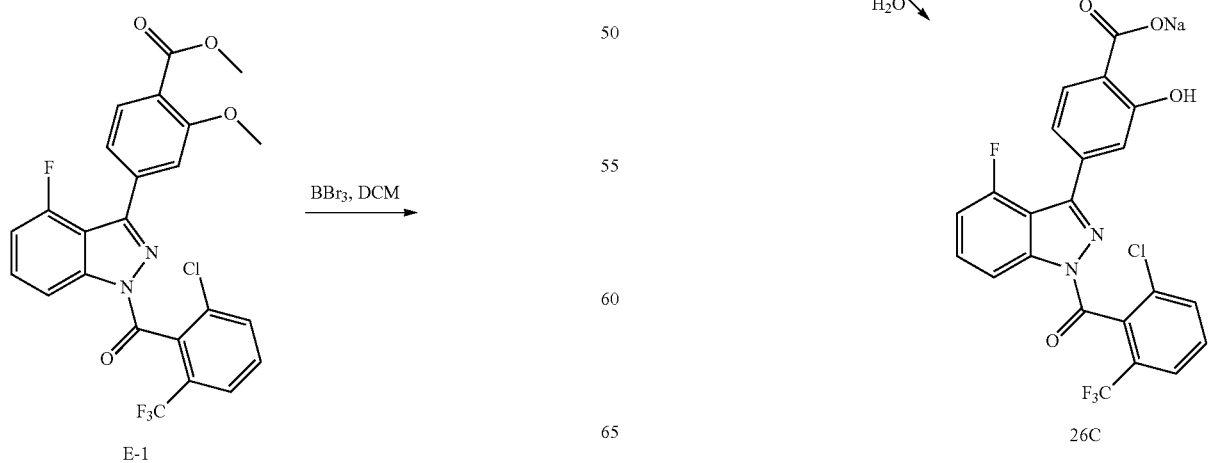

| Ex. | IUPAC name | P | Q | LCMS [M + H]+ (found) |
|---|---|---|---|---|
| 25W | 4-(6-(azetidine-1-carbonyl)-1-(2-chloro-6-(trifluoromethyl)benzoyl)-1H-indazol-3-yl)benzoic acid | | | 528 |

Example 26

Preparation of 4-(1-(2-chloro-6-(trifluoromethyl)benzoyl)-4-fluoro-1H-indazol-3-yl)-2-hydroxybenzoic acid (26A), 2-acetoxy-4-(1-(2-chloro-6-(trifluoromethyl)benzoyl)-4-fluoro-1H-indazol-3-yl)benzoic acid (26B) and sodium 4-(1-(2-chloro-6-(trifluoromethyl)benzoyl)-4-fluoro-1H-indazol-3-yl)-2-hydroxy benzoate (26C)

Scheme E.

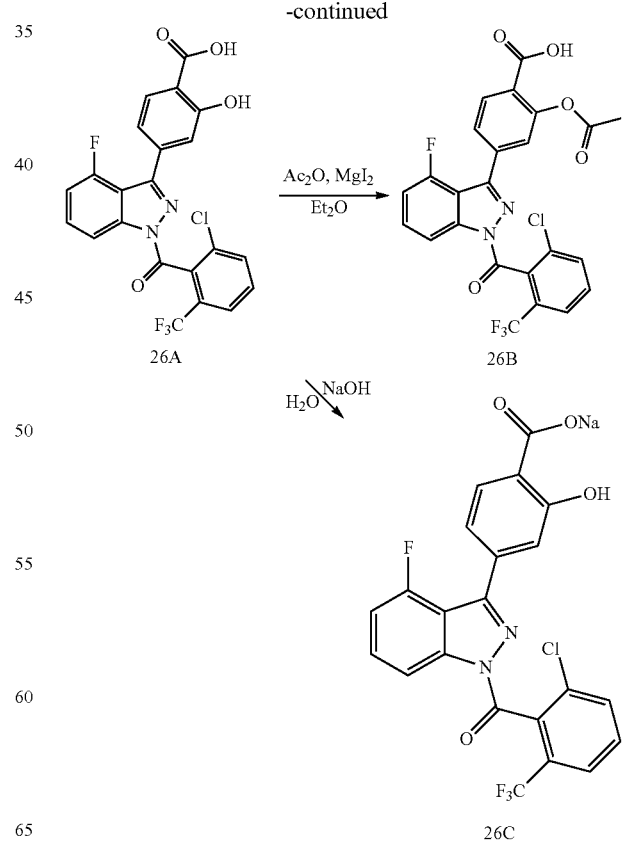

i) Preparation of 4-(1-(2-chloro-6-(trifluoromethyl) benzoyl)-4-fluoro-1H-indazol-3-yl)-2-hydroxybenzoic acid (26A)

To a solution of compound E-1 (prepared following a similar procedure in Scheme A) (100 mg, 0.19 mmol) in DCM (10 mL) was added $BBr_3$ (1M, 0.37 mL, 0.37 mmol) at rt, and the mixture was kept stirring for 48 h. Then MeOH (~10 mL) was added to quench excess $BBr_3$ and the mixture was concentrated under reduced pressure. The residue was purified by prep-HPLC to give the title compound as a yellow solid. LCMS (ESI) calc'd for $C_{22}H_{12}ClF_4N_2O_4$ [M+H]$^+$: 479. found: 479; $^1$H NMR (400 MHz, MeOD) δ 8.46 (1H, d, J=8.4 Hz), 7.95-7.76 (5H, m), 7.35-7.29 (3H, m).

ii) Preparation of 2-acetoxy-4-(1-(2-chloro-6-(trifluoromethyl)benzoyl)-4-fluoro-1H-indazol-3-yl) benzoic acid (26B)

A suspension of compound 26A (48 mg, 0.1 mmol), $Ac_2O$ (0.8 mL) and $MgI_2$ (28 mg, 0.1 mmol) in anhydrous ethyl ether (3 mL) was refluxed at 40° C. for 0.5 h. The reaction was cooled to rt, quenched with $H_2O$, extracted with ether, and concentrated. The crude product was dissolved in THF (10 mL)/$H_2O$ (10 mL) and refluxed at 80° C. for 1 h. The mixture was cooled to rt, diluted with $H_2O$, and extracted with EtOAc. The combined organic extracts were concentrated and purified by flash chromatography PE/EA (5/1) to give the title compound as a white solid. LCMS (ESI): calc'd for $C_{22}H_{12}ClF_4N_2O_4$ [M+H]$^+$: 521. found: 521, $^1$H NMR (400 MHz, MeOD) δ 8.47 (1H, d, J=8.0 Hz), 8.11 (1H, d, J=8.0 Hz), 7.90-7.76 (5H, m), 7.53 (1H, t, J=1.6 Hz), 3.34 (1H, q, J=8.0 Hz), 2.31 (3H, s).

iii) Preparation of sodium 4-(1-(2-chloro-6-(trifluoromethyl)benzoyl)-4-fluoro-1H-indazol-3-yl)-2-hydroxybenzoate (26C)

To a suspension of compound 26A (48 mg, 0.1 mmol) in $H_2O$ (20 mL) was added 0.1 M NaOH (1 mL), and the mixture was sonicated for ~10 mins. The mixture was then dried under lyophilizaiton to give the title compound. LCMS (ESI) calc'd for $C_{22}H_{11}ClF_4N_2NaO_4$ [M+H]$^+$: 501. found: 501; $^1$H NMR (400 MHz, MeOD) δ 8.45 (1H, d, J=8.0), 7.91-7.76 (5H, m), 7.31 (1H, q, J=8.0 Hz), 7.20-7.17 (2H, m).

The following examples shown in TABLE 4 were prepared following similar procedures described for Examples #26A, B, C in Scheme E, which can be achieved by those of ordinary skill in the art.

TABLE 4

| | IUPAC name | A ring | P | Q | LCMS [M + H]$^+$ (found) |
|---|---|---|---|---|---|
| 26D | 4-(1-(2-chloro-6-(trifluoromethyl)benzoyl)-4-fluoro-1H-indazol-3-yl)-2-fluoro-6-hydroxybenzoic acid | F-substituted benzene | 2-Cl, 6-CF$_3$ benzoyl | 2-F, 6-OH benzoic acid | 497 |
| 26E | 4-(1-(2-chloro-6-(trifluoromethyl)benzoyl)-4-fluoro-1H-indazol-3-yl)-3-hydroxybenzoic acid | F-substituted benzene | 2-Cl, 6-CF$_3$ benzoyl | 3-OH benzoic acid | 479 |

TABLE 4-continued

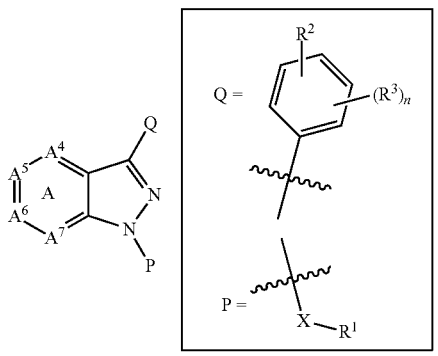

| | IUPAC name | A ring | P | Q | LCMS [M + H]+ (found) |
|---|---|---|---|---|---|
| 26F | 4-(1-(2-chloro-6-(trifluoro-methyl)benzoyl)-4-fluoro-1H-indazol-3-yl)-5-fluoro-2-hydroxybenzoic acid | | | | 497 |
| 26G | 4-(1-(2-chloro-6-(trifluoro-methyl)benzoyl)-4-fluoro-1H-indazol-3-yl)-3,6-difluoro-2-hydroxybenzoic acid | | | | 515 |
| 26H | 4-(1-(2-chloro-6-(trifluoro-methyl)benzoyl)-1H-pyrazolo[4,3-b]pyridin-3-yl)-2-hydroxybenzoic acid | | | | 462 |
| 26I | 2-acetoxy-4-(1-(2-chloro-6-(trifluoromethyl)benzoyl)-1H-pyrazolo[4,3-b]pyridin-3-yl)benzoic acid | | | | 504 |

TABLE 4-continued
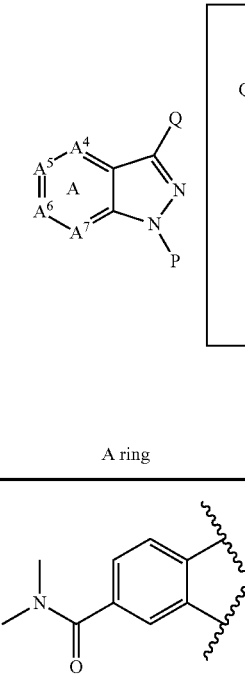
| | IUPAC name | A ring | P | Q | LCMS [M + H]+ (found) |
|---|---|---|---|---|---|
| 26J | 4-(1-(2-chloro-6-(trifluoro-methyl)benzoyl)-6-(dimethylcarbamoyl)-1H-indazol-3-yl)-2-hydroxybenzoic acid | 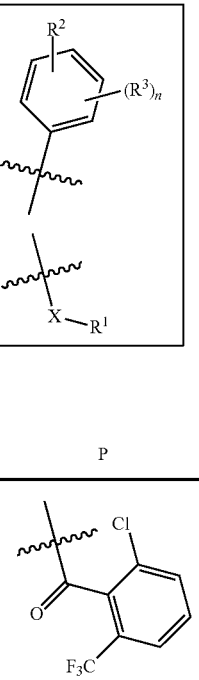 |  | 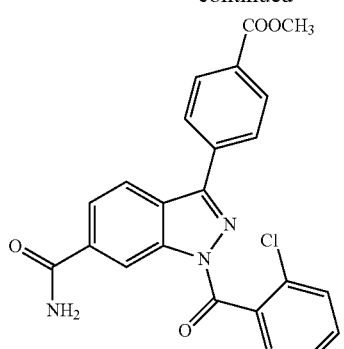 | 532 |
Example 27A
Preparation of 4-(6-(aminomethyl)-1-(2-chloro-6-(trifluoromethyl)benzoyl)-1H-indazol-3-yl)benzoic acid (27A)
Scheme F.
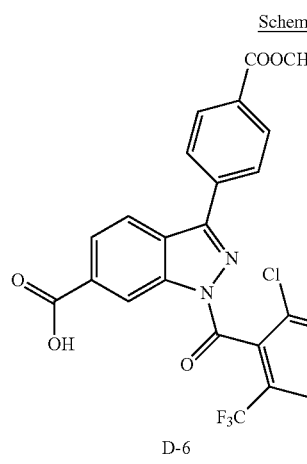

-continued

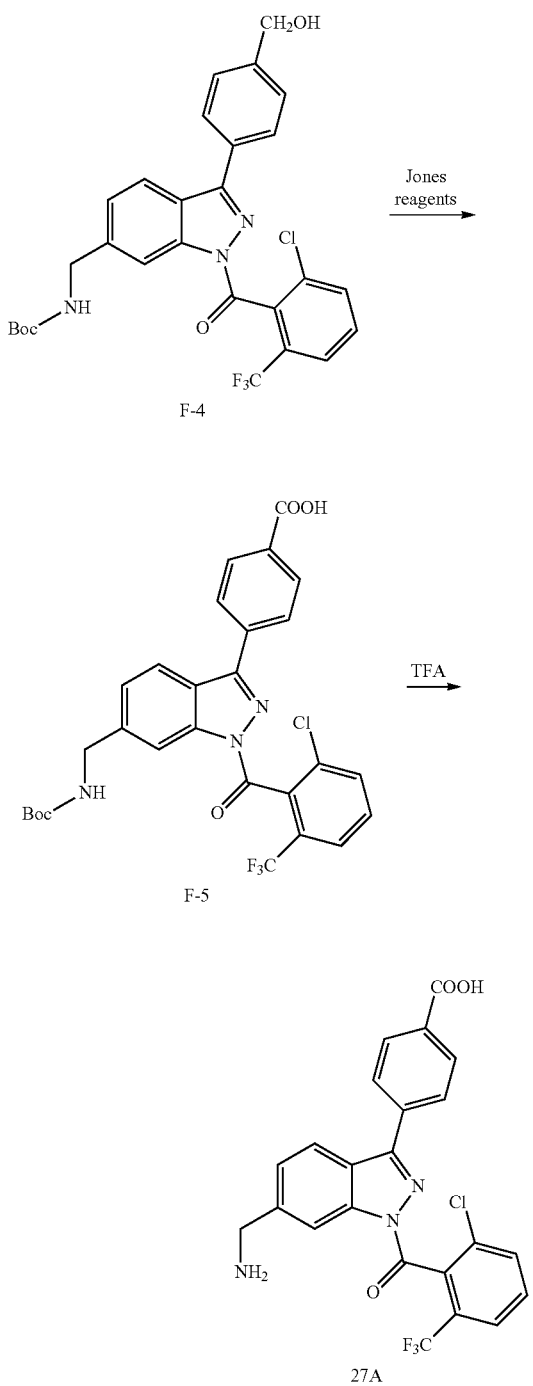

i) Preparation of methyl 4-(6-carbamoyl-1-(2-chloro-6-(trifluoromethyl)benzoyl)-1H-indazol-3-yl)benzoate (F-2)

To a solution of compound D-6 (180 mg, 0.36 mmol) in DCM (15 mL) was added PYAOP (374 mg, 0.72 mmol), followed by the addition of TEA (0.16 mL, 1.1 mmol). The mixture was stirred at rt for 2 h, diluted with EtOAc, washed with brine, dried over $Na_2SO_4$ and concentrated to give the title compound. LCMS (ESI) calc'd for $C_{24}H_{16}ClF_3N_3O_4$ [M+H]$^+$: 502. found: 502.1.

ii) Preparation of (6-(aminomethyl)-3-(4-(hydroxymethyl)phenyl)-1H-indazol-1-yl)(2-chloro-6-(trifluoromethyl)phenyl)methanone (F-3)

To solution of compound F-2 (175 mg, 0.35 mmol) in THF (20 mL) was added $BH_3$.THF (1.75 mL, 1.75 mmol) and the mixture was refluxed for 12 h. Then MeOH was added to quench the excess $BH_3$, and the mixture was concentrated under reduced pressure to give the title compound as a white solid. LCMS (ESI): calc'd for $C_{23}H_{18}ClF_3N_3O_2$ [M+H]$^+$: 460.1. found: 460.1.

iii) Preparation of tert-butyl (1-(2-chloro-6-(trifluoromethyl)benzoyl)-3-(4-(hydroxymethyl)phenyl)-1H-indazol-6-yl)methylcarbamate (F-4)

To a solution of compound F-3 (138 mg, 0.30 mmol) in $CH_2Cl_2$ (20 mL) was added (Boc)$_2$O (138 mg, 0.30 mmol), followed by the addition of excess. The mixture was stirred at rt for 2 h. The mixture was diluted with $H_2O$, extracted with EtOAc. The combined organics were washed with $H_2O$, brine, dried over $Na_2SO_4$, concentrated to give the title compound. LCMS (ESI) calc. $C_{28}H_{26}ClF_3N_3O_4$ [M+H]$^+$: 560.1. found: 560.1.

iv) Preparation of 4-(6-((tert-butoxycarbonylamino)methyl)-1-(2-chloro-6-(trifluoromethyl)benzoyl)-1H-indazol-3-yl)benzoic acid (F-5)

To a solution of compound F-4 (162 mg, 0.29 mmol) in acetone (10 mL) was added Jones reagent (2 mL), and the mixture was kept stirring at rt for 12 h. MeOH (20 mL) was added to quenched excess Jones reagent, and the mixture was filtered and rinsed with EtOAc. The organic layer was separated and concentrated to give the title compound. LCMS (ESI): calc'd for $C_{28}H_{24}ClF_3N_3O_5$ [M+H]$^+$: 574.1. Found: 574.1.

v) Preparation of 4-(6-(aminomethyl)-1-(2-chloro-6-(trifluoromethyl)benzoyl)-1H-indazol-3-yl)benzoic acid (27A)

To a solution of compound F-5 (100 mg, 0.17 mmol) in $CH_2Cl_2$ (10 mL) was added excess amount of TFA. The mixture was stirred at rt for 2 h. The mixture was concentrated, diluted with $H_2O$, and extracted with EtOAc. The combined organics were washed with $H_2O$, brine, dried over $Na_2SO_4$ and concentrated to give the title compound. LCMS (ESI): calc'd for $C_{23}H_{16}ClF_3N_3O_3$ [M+H]$^+$: 474.1. found: 474.1; $^1$H NMR (400 MHz, MeOD) δ 8.76 (1H, s), 8.23-8.25 (1H, m), 8.04-8.06 (2H, d, J=6.8 Hz), 7.88-7.91 (2H, m), 7.77-7.85 (3H, m), 7.66-7.68 (1H, d, J=8.8 Hz), 4.35 (2H, s).

The following examples shown in TABLE 5 were prepared following similar procedures described for Example #27A in Scheme F, which can be achieved by those of ordinary skill in the art.

TABLE 5
| Ex. | IUPAC name | R⁹R¹⁰N– | P | Q | LCMS [M + H]⁺ (found) |
|---|---|---|---|---|---|
| 27B | 4-(6-(aminomethyl)-1-(2-chloro-6-(trifluoromethyl)benzoyl)-1H-indazol-3-yl)-3-fluorobenzoic acid | H₂N– | 2-chloro-6-(trifluoromethyl)benzoyl | 4-carboxy-2-fluorophenyl | 492 |
Example 28
Preparation of 4-(1-(2-chloro-6-(trifluoromethyl)benzoyl)-1H-indazol-3-yl)-2-(difluoromethyl)benzoic acid
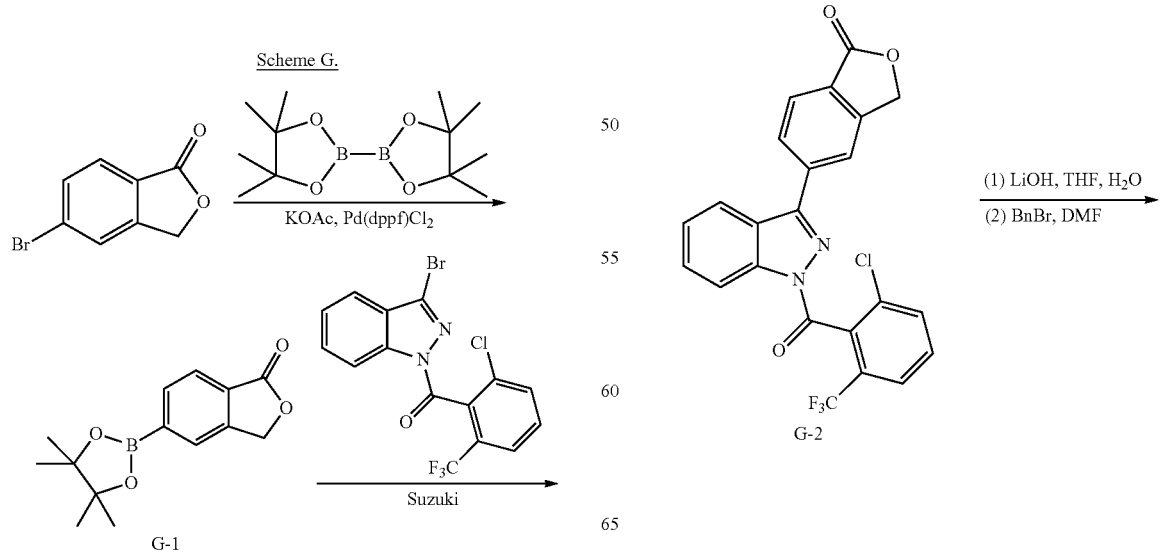

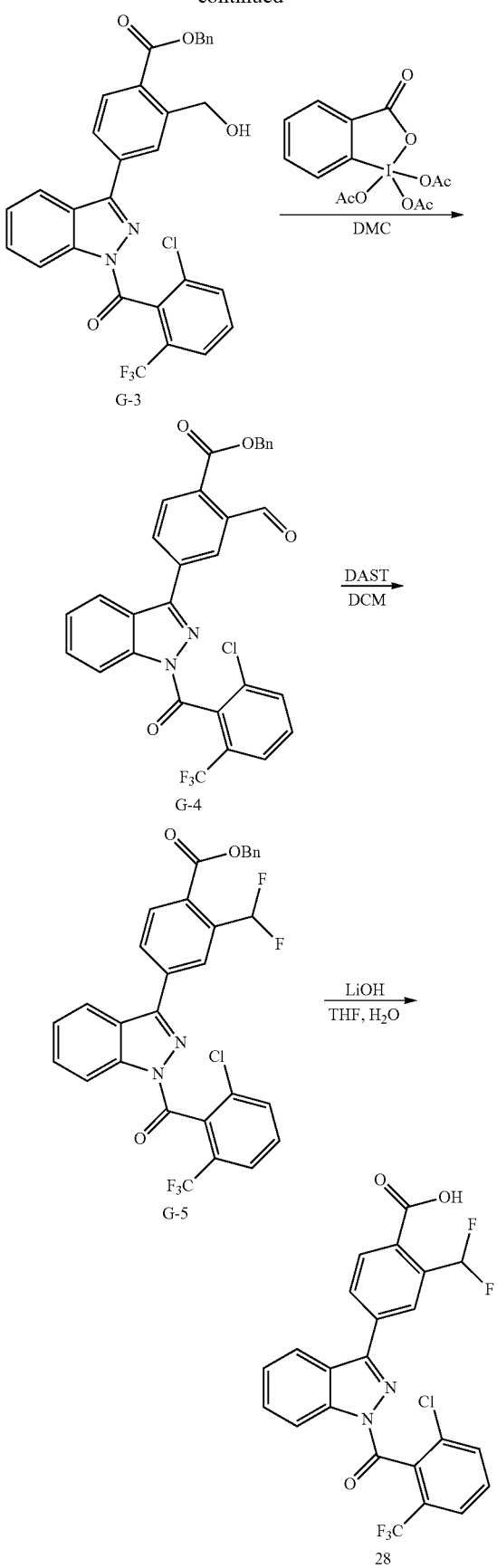

i) Preparation of 5-(4,4,5,5-tetramethyl-1,3,2-diox-aborolan-2-yl)isobenzo furan-1(3H)-one (G-1)

A mixture of 5-bromoisobenzofuran-1(3H)-one (1.5 g, 7.0 mmol), 4,4,4',4',5,5,5',5'-octamethyl-2,2'-bi(1,3,2-dioxaborolane) (2.1 g, 8.5 mmol), KOAc (2.1 g, 21 mmol), dppf (0.16 g, 0.28 mmol) and Pd(dppf)Cl$_2$ (0.26 g, 0.35 mmol) in dioxane (30 ml) was heated at 100° C. for 4 h. The mixture was cooled down and concentrated under reduced pressure. The residue was diluted with H$_2$O, and extracted with EtOAc. The combined organic layers were washed with brine, dried over Na$_2$SO$_4$, and concentrated. The residue was purified by flash chromatography (PE:EA=5:1) to give the title compound as a white solid. LCMS (ESI):calc. C$_{14}$H$_{18}$BO$_4$[M+H]$^+$: 261. found: 261.

ii) 5-(1-(2-chloro-6-(trifluoromethyl)benzoyl)-1H-indazol-3-yl)isobenzo furan-1 (3H)-one (G-2)

A mixture of 5-(4,4,5,5-tetramethyl-1,3,2-dioxaborolan-2-yl)isobenzofuran-1(3H)— one (G-1) (0.97 g, 2.48 mmol), (3-bromo-1H-indazol-1-yl)(2-chloro-6-(trifluoro methyl)phenyl)methanone (1.0 g, 2.48 mmol), K$_2$CO$_3$ (1.03 g, 7.44 mmol) and Pd(PPh$_3$)$_4$ (0.143 g, 0.12 mmol) were suspended in 1,4-dioxane (15 mL) and H$_2$O (3 mL). The reaction mixture was heated at 100° C. in a microwave reactor for 2 h. The reaction mixture was cooled to rt and diluted with H$_2$O. The aqueous layer was extracted with EtOAc. The combined organic layers were washed with brine, dried over Na$_2$SO$_4$ and concentrated. The residue was purified by flash chromatography (PE:EA=4:1) to afford the title compound as a pale yellow oil. LCMS (ESI) calc'd for C$_{23}$H$_{13}$ClF$_3$N$_2$O$_3$ [M+H]$^+$: 457. found: 457.

iii) Preparation of benzyl 4-(1-(2-chloro-6-(trifluoromethyl)benzoyl)-1H-indazol-3-yl)-2-(hydroxymethyl)benzoate (G-3)

A mixture of 5-(1-(2-chloro-6-(trifluoromethyl)benzoyl)-1H-indazol-3-yl)isobenzo furan-1(3H)-one (G-2) (0.6 g, 1.32 mmol) and LiOH (0.16 g, 6.58 mmol) in THF (6 mL) and H$_2$O (3 mL) was stirred at rt for 3 h. The solvent was removed under reduced pressure, and the residue was dissolved in DMF (10 mL), followed by the addition of BnBr (0.78 mL, 6.6 mmol). The resulting mixture was stirred at rt for 3 h. The mixture was diluted with H$_2$O, and EtOAc. The combined organic layers were washed with brine, dried over anhydrous Na$_2$SO$_4$ and concentrated. The residue was purified by flash chromatography (PE:EA=4:1) to give the title compound as a colorless oil. LCMS (ESI) calc'd for C$_{30}$H$_{19}$ClF$_5$N$_2$O$_3$ for [M+H]$^+$: 585. found: 585.

iv) Preparation of benzyl 4-(1-(2-chloro-6-(trifluoromethyl)benzoyl)-1H-indazol-3-yl)-2-formylbenzoate (G-4)

To a mixture of benzyl 4-(1-(2-chloro-6-(trifluoromethyl)benzoyl)-1H-indazol-3-yl)-2-(hydroxymethyl)benzoate (G-3) (0.4 g, 0.71 mmol) in DCM (10 mL) was added Dess-Martin periodinane (0.45 g, 1.07 mmol), and the mixture was stirred at rt for 24 h. The mixture was diluted with H$_2$O and extracted with DCM. The combined organic layers were washed with brine, dried over Na$_2$SO$_4$ and concentrated. The resulting crude oil was used in the next step without further purification. LCMS (ESI)' calc'd for C$_{30}$H$_{19}$ClF$_3$N$_2$O$_4$ [M+H]$^+$: 563. found: 563.

v) Preparation of benzyl 4-(1-(2-chloro-6-(trifluoromethyl)benzoyl)-1H-indazol-3-yl)-2-(difluoromethyl)benzoate (G-5)

To a solution of compound (G-4) (0.35 g, 0.62 mmol) in DCM (6 mL) at 0° C. was added a solution of DAST (0.42 mL, 3.1 mmol) in DCM (4 mL) dropwise. The mixture was warmed to rt and stirred for 2 h. The reaction mixture was then diluted with H$_2$O, and extracted with DCM. The combined organics were washed with brine, dried over Na$_2$SO$_4$, and concentrated. The residue was purified by flash chromatography (PE:EA=10:1) to give the title compound as a white solid. LCMS (ESI) calc'd for C$_{30}$H$_{19}$ClF$_5$N$_2$O$_3$ [M+H]$^+$: 585. found: 585.

vi) 4-(1-(2-chloro-6-(trifluoromethyl)benzoyl)-1H-indazol-3-yl)-2-(difluoromethyl)benzoic acid (28)

A mixture of compound (G-5) (0.17 mg, 0.30 mmol) and LiOH (63 mg, 1.5 mmol) in THF (6 mL) and H2O (3 mL) was stirred at rt for 24 h. The mixture was acidified with 2M HCl to PH=~3, and extracted with EtOAc. The combined organic layers were washed with brine, dried over Na$_2$SO$_4$ and concentrated. The residue was purified with prep-HPLC to give the title compound as a white solid. LCMS (ESI) calc'd for C$_{23}$H$_{13}$ClF$_5$N$_2$O$_3$ [M+H]$^+$: 495. found: 495; $^1$H NMR (400 MHz, CDCl$_3$) δ 8.70 (1H, d, J=8 Hz), 8.35 (1H, s), 8.25 (1H, d, J=8 Hz), 8.02-8.05 (2H, m), 7.71-7.77 (3H, m), 7.49-7.64 (3H, m).

Example 29

Preparation of 4-(1-(2-chloro-6-(trifluoromethyl) benzoyl)-6-cyano-1H-indazol-3-yl)benzoic acid Scheme H.

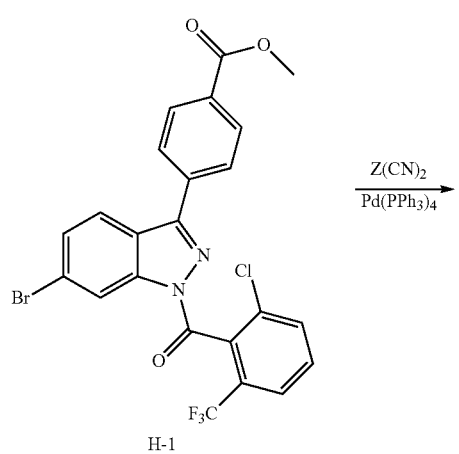

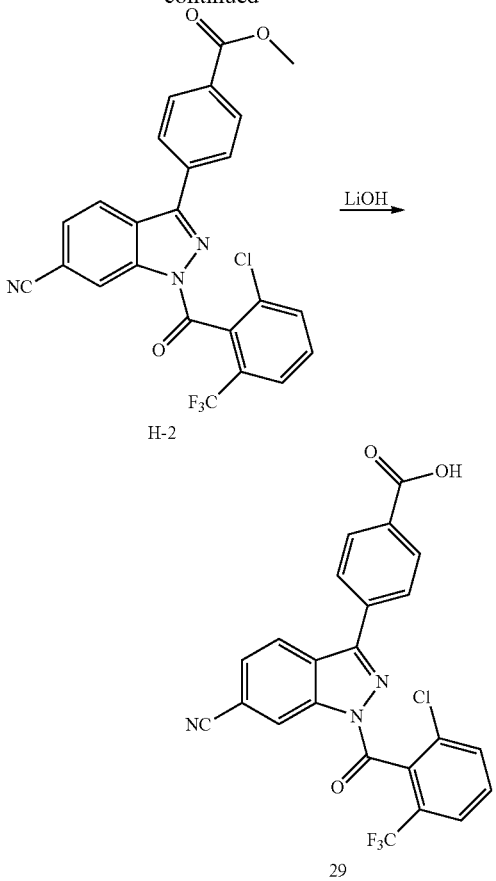

i) Preparation of methyl 4-(1-(2-chloro-6-(trifluoromethyl)benzoyl)-6-cyano-1H-indazol-3-yl)benzoate (H-2)

To a solution of compound H-1 (100 mg, 0.186 mmol) (prepared according to a similar procedure in Scheme A) in DMF (2 mL) was added Zn(CN)$_2$ (44 mg, 0.37 mmol) and Pd(PPh$_3$)$_4$ (22 mg, 0.019 mmol). The mixture was purged with N$_2$ and then stirred at 100° C. for 1 h under microwave. The reaction mixture was cooled down to rt and diluted with H$_2$O, and extracted with EtOAc. The combined organics were dried over anhydrous Na$_2$SO$_4$, filtered and concentrated. The crude solid was purified by Prep-TLC (20*20 cm)(PE/EA=3/1) to obtain the title compound as a brown solid. LCMS (ESI) calc'd for C$_{24}$H$_{14}$F$_3$N$_3$O$_3$Cl [M+H]$^+$: 484. Found: 484.

ii) Preparation of 4-(1-(2-chloro-6-(trifluoromethyl) benzoyl)-6-cyano-1H-indazol-3-yl)benzoic acid (29)

A mixture of compound H-2 (49 mg, 0.10 mmol), and LiOH (37 mg, 0.88 mmol) in dioxane (10 mL) and H$_2$O (2 mL) was stirred at rt for 24 h. The mixture was acidified with AcOH to PH=~4, and extracted with DCM. The combined organics were washed with brine, dried over anhydrous Na$_2$SO$_4$ and concentrated. The residue was purified by prep HPLC to give the title compound as a white solid. LCMS (ESI) calc'd for C$_{23}$H$_{12}$F$_4$N$_3$O$_3$Cl [M+H]$^+$: 470. found: 470; $^1$H NMR (400 MHz, DMSO) δ 13.23 (1H, s), 8.99 (1H, s), 8.49 (1H, d, J=8.4 Hz), 8.03-8.12 (5H, m), 7.89-7.98 (3H, m).

Biological Assays

The compounds of the invention inhibit RORgammaT activity. Activation of RORgammaT activity can be measured using e.g. biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (eg NR box) motifs (Xie et al., *J. Immunol.* 175: 3800-09, 2005; Kurebayashi et al., Biochem. Biophys. Res. Commun. 315: 919-27, 2004; Jin et al., *Mol. Endocrinology* 24:923-29, 2010). The assay was run following three slightly different protocols, i.e. Protocol A, Protocol B, and Protocol C, which are described below. The TR-FRET assay following Protocol A is described below and the results thereof shown in Table 1 below.

TR-FRET Assay (Protocol A)

In the current setting, a peptide from Steroid Receptor Co-factor 1 box 2 (SRC1_2) is aminoterminal biotinylated (biotinyl-CPSSHSSLTERHKILHRLLQEGSPS, NEOMPS, France) and the applied RORgamma-LBD contains a 6-His and GST tag. The 6His(GST)RORgamma-LBD was expressed and purified from baculovirus infected Sf-21 insect cells (Bac-to-BAC, Invitrogen) and purified using glutathione sepharose chromatography (GE healthcare). Biotin and H is function as anchoring points for streptavidin-allophycocyanin (Strep-APC, Perkin Elmer, C130-100) and anti-His-Europium Cryptate (Perkin Elmer, AD0111), respectively. Since energy transfer between the streptavidin and His-coupled labels APC and europium cryptate can only take place when these labels are in close proximity, measurement of energy transfer in a mixture of biotinylated peptide, His-GR-LBD, streptavidin-APC and anti-His-Europium Cryptate will be indicative for RORγ-LBD/peptide binding. Final assay conditions in 50 µl are: TR-FRET buffer [50 mM KCl, 50 mM TRIS, 1 mM Na-EDTA, 0.1 mM DTT, (pH 7.0)]; 6His(GST) RORgamma-LBD 10 nM, Anti-6His-Eu 1.25 nM, SRC1_2 peptide 0.1 µM, Strep-APC 8 nM. Changes in peptide binding caused by dose-curves of compounds added to the reaction mixture (DMSO concentration 0.1%), can likewise be monitored. Fluorescence emission at 665 nm (excitation wavelength 340 nm) was read in each well of 384 well plates (Perkin Elmer, 60007299) using an Envision fluorescence reader in Time Resolved mode (Perkin Elmer) after overnight incubation at 4° C. Dose-response data are curve-fitted (IBDS Software, ActivityBase) and pEC50 values calculated. pEC50 values for Examples 1-23 using Protocol A are provided in Table 6 below. All compounds of the invention have a pEC50 of 4 or higher. Preferred are compounds with a pEC50 of more than 5.

TABLE 6

| Example | pEC50 |
| --- | --- |
| 1 | 7.97 |
| 2 | 6.61 |
| 3 | 7.73 |
| 4 | 8.08 |
| 5 | 6.76 |
| 6A | 7.87 |
| 6B | 6.65 |

TABLE 6-continued

| Example | pEC50 |
| --- | --- |
| 7 | 7.85 |
| 8 | 5.31 |
| 9 | 5.03 |
| 10 | 7.64 |
| 11A | 6.47 |
| 11B | 7.35 |
| 11C | 6.29 |
| 11D | 6.28 |
| 11E | 7.57 |
| 11F | 7.4 |
| 11G | 7.22 |
| 11H | 7.15 |
| 11I | 7.14 |
| 11J | 5.72 |
| 11K | 7.67 |
| 11L | 7.58 |
| 11M | 7.98 |
| 11N | 7.59 |
| 12 | 7.17 |
| 13A | 6.81 |
| 13B | 7.1 |
| 13C | 7.12 |
| 13D | 7.28 |
| 13E | 7.58 |
| 13F | 6.78 |
| 14 | 5.71 |
| 15A | 6.56 |
| 15B | 6.74 |
| 15C | 7.85 |
| 15D | 5.35 |
| 15E | 6.29 |
| 17 | 5.91 |
| 18 | 5.48 |
| 16 | 6.02 |
| 20 | 5.45 |
| 21A | 6.41 |
| 21B | 6.24 |
| 21C | 6.21 |
| 21D | 6.13 |
| 22 | 5.3 |
| 23 | 5.99 |

TR-Fret Assay (Protocol B)

HIS-tagged RORγ-LBD was recombinantly expressed in SF9 cells using a baculovirus expression system. The protein was not purified. Cells were lysed and the lysate was used as a source for RORγ-LBD for the assay. A 1:80 dilution of RORγ-LBD lysate in assay buffer (25 mM HEPES pH 7.0, 100 mM NaCl, 0.01% Tween, 0.1% BSA) was prepared and 5 µL was added to each well (RORγ-LBD final concentration ~10 nM). Control wells received lysate from SF9 cells not expressing RORγ-LBD.

Compounds to be tested were diluted to 100× final test concentration in DMSO and further diluted to 4× final test concentration using assay buffer to provide the test compound mixture. An aliquot (5 µL) of the test compound mixture was added to each well.

A 4× stock of biotinylated-LXXLL peptide from SRC1-2 (Biotin-CPSSHSSLTERHKILHRLLQEGSPS) was prepared in assay buffer and a 5 µL aliquot added to each well (450 nM final concentration). A 4× solution of europium tagged anti-HIS antibody (2 nM final concentration) and APC conjugated streptavidin (60 nM final concentration) were prepared and a 5 µL aliquot added to each well.

The final assay mixture was incubated for 4 hours to overnight, and the fluorescence signal was measured on an Envision plate reader: (Excitation filter=340 nm; APC emission=665 nm; Europium emission=615 nm; dichroic mirror=D400/D630; delay time=100 µs, integration time=200 µs).

IC50 values for test compounds were calculated from the quotient of the fluorescence signal at 665 nm divided by the fluorescence signal at 615 nm using GraphPad Prism software.

TR-Fret Assay (Protocol C)

HIS-tagged RORγ-LBD protein was expressed in SF9 cells using a baculovirus expression system. The RORγ-LBD protein was purified by glutathione sepharose chromatography. Separately, SF9 cells not expressing any recombinant protein were lysed and the lysate was added to the purified RORγ-LBD at 0.25 μl lysate (from 10,000 SF9 cells)/nM purified protein. The mixture was then diluted in assay buffer (50 mM Tris pH 7.0, 50 mM KCl, 1 mM EDTA, 0.1 mM DTT) to obtain RORγ-LBD final concentration of 3 nM in 384-well assay plate.

Compounds to be tested were injected to the assay plate using Acoustic Droplet Ejection technology by Echo 550 liquid handler (Labcyte, Calif.).

A stock of biotinylated-LXXLL peptide from coactivator SRC1 (Biotin-CPSSHSSLTERHKILHRLLQEGSPS) was prepared in assay buffer and added to each well (100 nM final concentration). A solution of Europium tagged anti-HIS antibody (1.25 nM final concentration) and APC conjugated streptavidin (8 nM final concentration) were also added to each well.

The final assay mixture was incubated for overnight at 4° C., and the fluorescence signal was measured on an Envision plate reader: (Excitation filter=340 nm; APC emission=665 nm; Europium emission=615 nm; dichroic mirror=D400/D630; delay time=100 μs, integration time=200 μs). IC50 values for test compounds were calculated from the quotient of the fluorescence signal at 665 nm divided by the fluorescence signal at 615 nm.

Table 7 below tabulates the biological data disclosed for Examples 24A-29 as a range of Fret $IC_{50}$ values, which was reported as ranges according to the annotation delineated below:

* $IC_{50}$<50 nM
** $IC_{50}$>50 and <500 nM
*** $IC_{50}$>500 and <10000 nM
**** $IC_{50}$>10000 nM

TABLE 7

| Examples | Fret $IC_{50}$ | Assay protocol |
|---|---|---|
| 24A | * | B |
| 24B | * | B |
| 24C | * | B |
| 24D | *** | B |
| 24E | *** | B |
| 24F | *** | B |
| 24G | *** | B |
| 24H | * | B |
| 24I | * | B |
| 24J | ** | B |
| 24K | * | B |
| 24L | * | B |
| 24M | * | B |
| 24N | * | B |
| 24O | * | B |
| 24P | * | B |
| 24Q | ** | B |
| 24R | * | B |
| 24S | *** | B |
| 24T | **** | B |
| 24U | * | B |
| 24V | * | B |
| 24W | * | B |
| 24X | ** | B |
| 24Y | * | B |
| 24Z | **** | B |
| 24AA | * | B |
| 24AB | * | B |
| 24AC | *** | B |
| 24AD | *** | B |
| 24AE | *** | B |
| 24AF | * | B |
| 24AG | * | B |
| 24AH | * | B |
| 24AI | ** | B |
| 24AJ | ** | B |
| 24AK | * | B |
| 24AL | **** | C |
| 24AM | * | B |
| 24AN | * | B |
| 24AO | * | B |
| 24AP | *** | B |
| 24AQ | * | B |
| 24AR | * | B |
| 24AS | * | C |
| 24AT | * | B |
| 24AU | * | C |
| 24AV | ** | C |
| 24AW | ** | C |
| 24AX | * | B |
| 24AY | ** | B |
| 24AZ | ** | B |
| 24BA | * | B |
| 24BB | * | B |
| 24BC | *** | B |
| 24BD | *** | B |
| 24BE | * | B |
| 24BF | * | B |
| 24BG | ** | C |
| 25A | * | B |
| 25B | * | B |
| 25C | * | B |
| 25D | * | B |
| 25E | * | B |
| 25F | * | B |
| 25G | ** | B |
| 25H | * | B |
| 25I | ** | B |
| 25J | * | B |
| 25K | * | B |
| 25L | * | B |
| 25M | * | B |
| 25N | * | C |
| 25O | * | B |
| 25P | * | B |
| 25Q | * | B |
| 25R | * | B |
| 25S | * | C |
| 25T | * | C |
| 25U | * | C |
| 25V | * | C |
| 25W | * | C |
| 26A | * | B |
| 26B | * | B |
| 26C | * | B |
| 26D | * | B |
| 26E | * | B |
| 26F | * | C |
| 26G | * | C |
| 26H | * | B |
| 26I | * | B |
| 26J | * | B |
| 27A | * | B |
| 27B | * | B |
| 28 | * | B |
| 29 | ** | B |

The invention claimed is:

1. A compound according to Formula I

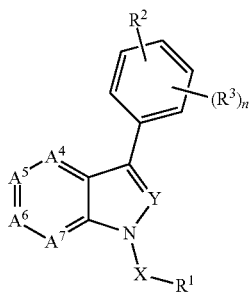

or a pharmaceutically acceptable salt or solvate thereof, wherein

X is C(O), SO or $SO_2$,

Y is CH or N;

n=0, 1, 2, 3 or 4;

$A^4$-$A^7$ are independently N or $CR^4$, $CR^5$, $CR^6$ or $CR^7$, respectively, with the proviso that no more than two of the four positions $A^4$-$A^7$ can be simultaneously N, wherein $A^4$ is N, $A^5$ is $CR^5$, $A^6$ is $CR^6$, and $A^7$ is $CR^7$;

$R^1$ is (i) ($C_{3-7}$)cycloalkyl or ($C_{3-5}$)heterocycloalkyl, both optionally substituted with one or more groups selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl and ($C_{1-3}$)alkoxy are optionally substituted with one or more halogens; (ii) ($C_{2-9}$)heteroaryl, optionally substituted with one or more groups selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl and ($C_{1-3}$)alkoxy are optionally substituted with one or more halogens; or (iii) ($C_{6-14}$)aryl, optionally substituted with one or more groups selected from halogen, amino, cyano, nitro, hydroxy, $H_2NC(O)$—, ($C_{1-3}$)alkoxycarbonyl, (di)($C_{1-6}$)alkylaminocarbonyl, ($C_{1-4}$)alkyl or ($C_{1-3}$)alkoxy, wherein ($C_{1-3}$)alkoxycarbonyl, (di)($C_{1-6}$)alkylaminocarbonyl, ($C_{1-4}$)alkyl or ($C_{1-3}$)alkoxy are optionally substituted with one or more halogens;

$R^2$ is C(O)OH, 5-tetrazoylyl, $HOC(CF_3)_2$, $C(O)OH(C_{1-10})$alkyl, ($C_{1-10}$)alkylsulfoxyaminocarbonyl; or carbamoyl;

$R^3$ is hydrogen, halogen, cyano, nitro, hydroxy, (C1-3)alkylC(O)O—, ($C_{1-4}$)alkyl, or ($C_{1-4}$)alkoxy, wherein ($C_{1-4}$)alkyl and ($C_{1-4}$)alkoxy are optionally substituted with one or more halogen;

$R^4$-$R^7$ independently are H, halogen, amino, cyano, hydroxy, ($C_{1-3}$)alkoxy, ($C_{1-4}$)alkyl, ($C_{0-10}$alkyl)aminocarbonyl, (di)($C_{1-6}$)alkylaminocarbonyl or amino($C_{1-4}$)alkyl, wherein ($C_{1-3}$)alkoxy, ($C_{1-4}$)alkyl, ($C_{0-10}$alkyl)aminocarbonyl, (di)($C_{1-6}$)alkylaminocarbonyl and amino($C_{1-4}$)alkyl are optionally substituted with one or more halogen, hydroxyl or ($C_{1-3}$)alkoxy; or a group having the formula

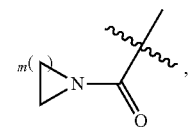

optionally substituted with one or more of the following: ($C_{1-10}$)alkyl, halogen, amino, cyano, hydroxy, ($C_{1-3}$)alkoxy, and wherein m is 1, 2, 3, or 4.

2. A compound according to Formula Ia

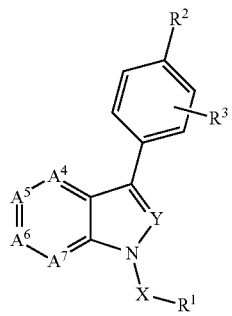

Ia or a pharmaceutically acceptable salt or solvate thereof, wherein
X represents C(O), SO or SO$_2$,
Y is CH or N;
A$^4$-A$^7$ are independently N or CR$^4$, CR$^5$, CR$^6$ or CR$^7$, respectively, with the proviso that no more than two of the four positions A$^4$-A$^7$ can be simultaneously N, wherein A$^4$ is N, A$^5$ is CR$^5$, A$^6$ is CR$^6$, and A$^7$ is CR$^7$;
R$^1$ is (C$_{3-7}$)cycloalkyl or (C$_{3-5}$)heterocycloalkyl, both optionally substituted with one or more groups selected from halogen, amino, cyano, hydroxy, H$_2$NC(O)—, or (C$_{1-3}$)alkoxycarbonyl, (di)(C$_{1-6}$)alkylaminocarbonyl, (C$_{1-4}$alkyl or (C$_{1-3}$)alkoxy, all optionally substituted with one or more halogens or;
R$^1$ is (C$_{2-9}$)heteroaryl, optionally substituted with one or more groups selected from halogen, amino, cyano, nitro, hydroxy, H$_2$NC(O)—, or (C$_{1-3}$)alkoxycarbonyl, (di)(C$_{1-6}$)alkylaminocarbonyl, (C$_{1-4}$)alkyl or (C$_{1-3}$)alkoxy, all optionally substituted with one or more halogens or;
R$^1$ is (C$_{6-14}$)aryl, optionally substituted with one or more groups selected from halogen, amino, cyano, nitro, hydroxy, H$_2$NC(O)—, or (C$_{1-3}$)alkoxycarbonyl, (di)(C$_{1-6}$)alkylaminocarbonyl, (C$_{1-4}$)alkyl or (C$_{1-3}$)alkoxy, all optionally substituted with one or more halogens;
R$^2$ is C(O)OH, 5-tetrazoylyl, or HOC(CF$_3$)$_2$;
R$^3$ is independently selected from hydrogen, halogen, cyano, nitro or (C$_{1-4}$)alkyl, optionally substituted with one or more halogens; and
R$^4$-R$^7$ independently are H, halogen, amino, cyano, hydroxy, (C$_{1-3}$)alkoxy, (C$_{1-4}$alkyl, optionally substituted with one or more halogens.

3. The compound of claim 1, wherein Y is N.
4. The compound of claim 3, wherein
X is C(O) or SO$_2$;
R$^1$ is (i) (C$_{3-7}$)cycloalkyl or (C$_{3-5}$)heterocycloalkyl, both optionally substituted with one or more groups selected from (C$_{1-4}$)alkyl or halogen; (ii) (C$_{2-9}$)heteroaryl, optionally substituted with one or more groups selected from halogen, amino or (C$_{1-4}$)alkyl; or (iii) (C$_{6-14}$)aryl, optionally substituted with one or more groups selected from halogen, amino, cyano, nitro, hydroxy, (C$_{1-3}$)alkoxycarbonyl, (C$_{1-4}$)alkyl, (C$_{1-3}$)alkoxy, wherein (C$_{1-3}$)alkoxycarbonyl, (C$_{1-4}$)alkyl and (C$_{1-3}$)alkoxy are optionally substituted with one or more halogens.
5. The compound of claim 4, wherein
R$^1$ is (C$_{2-9}$)heteroaryl or (C$_{6-14}$)aryl, both optionally substituted with one or more groups selected from halogen, amino, cyano, nitro, hydroxy, (C$_{1-3}$)alkoxycarbonyl, (C$_{1-4}$)alky or (C$_{1-3}$)alkoxy, wherein (C$_{1-3}$)alkoxycarbonyl, (C$_{1-4}$)alkyl and (C$_{1-3}$)alkoxy are optionally substituted with one or more halogens.

6. The compound of claim 5 wherein R$^1$ is phenyl, naphthyl, pyridinyl, quinolinyl, benzooxadiazolyl, thiophenyl, or isoxazolyl, each optionally substituted with one or more groups selected from halogen, amino, cyano, nitro, hydroxy, (C$_{1-3}$)alkoxycarbonyl, (C$_{1-4}$)alkyl or (C$_{1-3}$)alkoxy, wherein (C$_{1-3}$)alkoxycarbonyl, (C$_{1-4}$)alkyl and (C$_{1-3}$)alkoxy are optionally substituted with one or more halogens.

7. The compound of claim 6, wherein R$^1$ is phenyl, optionally substituted with one or more groups selected from halogen, amino, cyano, nitro, hydroxy, (C$_{1-3}$)alkoxycarbonyl, (C$_{1-4}$)alkyl or (C$_{1-3}$)alkoxy, wherein (C$_{1-3}$)alkoxycarbonyl, (C$_{1-4}$)alkyl and (C$_{1-3}$)alkoxy are optionally substituted with one or more halogens.

8. The compound of claim 7, wherein R$^2$ is C(O)OH.

9. The compound of claim 1 having Formula Ib

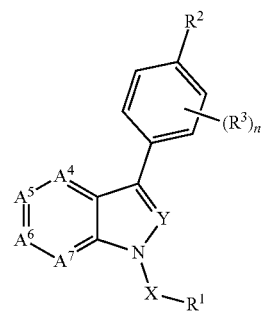

Ib or a pharmaceutically acceptable salt or solvate thereof.

10. The compound of claim 9 having Formula Ic

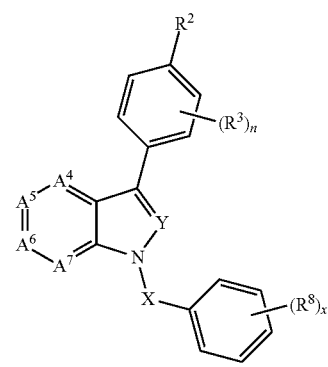

Ic or a pharmaceutically acceptable salt or solvate thereof, wherein,
X is C(O) or SO$_2$
R$^8$ is selected from halogen, amino, cyano, nitro, hydroxy, H$_2$NC(O)—, (C$_{1-3}$)alkoxycarbonyl, (di)(C$_{1-6}$)alkylaminocarbonyl, (C$_{1-4}$)alkyl or (C$_{1-3}$)alkoxy, wherein (C$_{1-3}$)alkoxycarbonyl, (di)(C$_{1-6}$)alkylaminocarbonyl, (C$_{1-4}$)alkyl or (C$_{1-3}$)alkoxy are optionally substituted with one or more halogens; and
x is 0, 1, 2, 3, 4 or 5.

11. The compound of claim 10 having Formula Id

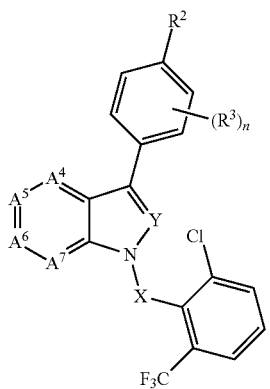

or a pharmaceutically acceptable salt or solvate thereof.

12. The compound of claim 11 having Formula Ie

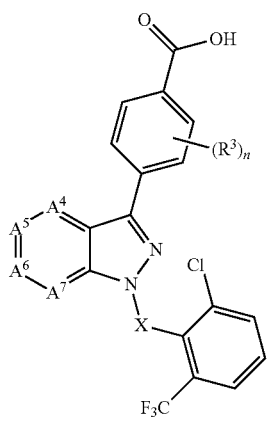

or a pharmaceutically acceptable salt or solvate thereof.

13. A compound according to claim 1 selected from:
4-(1-(2,6-dichlorbenzoyl)-1H-pyrazolo[4,3-b]pyridin-3-yl)benzoic acid;
4-(1-(2-(trifluoromethyl)benzoyl)-1H-pyrazolo[4,3-b]pyridin-3-yl)benzoic acid;
4-(1-(2,6-dichlorobenzoyl)-1H-pyrrolo[3,2-b]pyridin-3-yl)benzoic acid;
4-(1-(2,6-dichlorobenzoyl)-1H-pyrazolo[4,3-c]pyridin-3-yl)benzoic acid;
methyl4-(1-(2-chloro-6-(trifluoromethyl)benzoyl)-1H-pyrazolo[4,3-b]pyridin-3-yl)-3-fluorobenzoate;
sodium4-(1-(2-chloro-6-(trifluoromethyl)benzoyl)-1H-pyrazolo[4,3-b]pyridin-3-yl)-3-fluorobenzoate;
3-(1-(2-chloro-6-(trifluoromethyl)benzoyl)-1H-pyrazolo[4,3-b]pyridin-3-yl)benzoic acid;
2-(4-(1(2-chloro-6-(trifluoromethyl)benzoyl)-1H-pyrazolo[4,3-b]pyridin-3-yl)phenyl)acetic acid;
(2-chloro-6-(trifluoromethyl)phenyl)(3-(4-(1,1,1,3,3,3-hexafluoro-2-hydroxypropan-2-yl)phenyl)-1H-pyrazolo[4,3-b]pyridin-1-yl)methanone;
4-(1-(2-chloro-6-(trifluoromethyl)benzoyl)-1H-pyrazolo[4,3-b]pyridin-3-yl)-3-methylbenzoic acid;
3-chloro-4(1-(2-chloro6-(trifluoromethyl)benzoyl)-1H-pyrazolo[4,3-b]pyridin-3-yl)benzoic acid;
4-(1-(2-chloro-6-(trifluoromethyl)benzoyl)-1H-pyrazolo[4,3-b]pyridin3-yl)-2-fluorobenzoic acid;
4-(1-(2-chloro-6-(trifluoromethyl)benzoyl)-1H-pyrazolo[4,3-b]pyridin-3-yl)-2methoxybenzoic acid;
2-chloro-4-(1-(2-chloro-6-(trifluoromethyl)benzoyl)-1H-pyrazolo[4,3-b]pyridin-3-yl)-5-fluorobenzoic acid;
4-(1-(2-chloro-6-(trifluoromethyl)benzoyl)-1H-pyrazolo[4,3-b]pyridin-3-yl)-2,5-difluorobenzoic acid;
5-(1-(2-chloro-6-(trifluoromethyl)benzoyl)-1H-pyrazolo[4,3-b]pyridin-3-yl)-2-hydroxybenzoic acid;
4-(1-(2-fluoro-6-methoxybenzoyl)-1H-pyrazolo[4,3-b]pyridin-3-yl)benzoic acid;
3-fluoro-4-(1-(2-fluoro-6-methoxybenzoyl)-1H-pyrazolo[4,3-b]pyridin-3-yl)benzoic acid;
4-(1-(2-chloro-6-(trifluoromethyl)benzoyl)-1H-pyrazolo[4,3-b]pyridin-3-yl)-2-hydroxybenzoic acid;
2-acetoxy-4-(1-(2-chloro-6-(trifluoromethyl)benzoyl)-1H-pyrazolo[4,3-b]pyridin-3-yl)benzoic acid;
4-(1-(2-chloro-6-(trifluoromethyl)benzoyl)-1H-pyeazolo[4,3-b]pyridin-3-yl)-3-fluorobenzoic acid;
or a pharmaceutically acceptable salt thereof.

14. A pharmaceutical composition comprising a compound of claim 1 or a pharmaceutically acceptable salt or solvate thereof and one or more pharmaceutically acceptable excipients.

15. The pharmaceutical composition of claim 14, which further comprises at least one additional therapeutically active agent.

16. 4-(1-(2-chloro-6-(trifluoromethyl)benzoyl)-1H-pyrazolo[4,3-b]pyridin-3-yl)-3-fluorobenzoic acid, having the formula

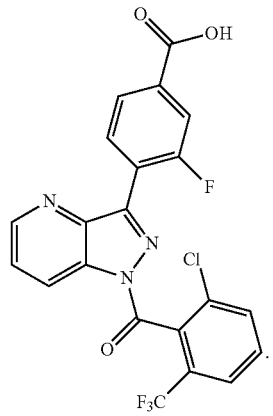 [SMILES: O=C(O)c1ccc(-c2nn(C(=O)c3c(Cl)cccc3C(F)(F)F)c3cccnc23)c(F)c1]

17. A pharmaceutically acceptable salt of the compound of claim 16.

18. A pharmaceutical composition comprising the compound of claim 16 or a pharmaceutically acceptable salt thereof and one or more pharmaceutically acceptable excipients.

19. The pharmaceutical composition of claim 18, which further comprises at least one additional therapeutically active agent.

* * * * *